US012275007B2

(12) United States Patent
Montgomery et al.

(10) Patent No.: US 12,275,007 B2
(45) Date of Patent: Apr. 15, 2025

(54) HANDHELD IMPEDANCE-BASED DIAGNOSTIC TEST SYSTEM FOR DETECTING ANALYTES

(71) Applicant: Alveo Technologies, Inc., Alameda, CA (US)

(72) Inventors: Kyle William Montgomery, Concord, CA (US); Daniel J. Wade, Bay Point, CA (US); Shad Pierson, Sacramento, CA (US); Yuh-Min Chiang, Sunnyvale, CA (US); Ronald Phillip Chiarello, Orinda, CA (US)

(73) Assignee: ALVEO Technologies, Inc., Alameda, CA (US)

( * ) Notice: Subject to any disclaimer, the term of this patent is extended or adjusted under 35 U.S.C. 154(b) by 902 days.

(21) Appl. No.: 17/416,095

(22) PCT Filed: Dec. 18, 2019

(86) PCT No.: PCT/US2019/067080
§ 371 (c)(1),
(2) Date: Jun. 18, 2021

(87) PCT Pub. No.: WO2020/132008
PCT Pub. Date: Jun. 25, 2020

(65) Prior Publication Data
US 2022/0072539 A1 Mar. 10, 2022

Related U.S. Application Data

(60) Provisional application No. 62/931,079, filed on Nov. 5, 2019, provisional application No. 62/831,387, filed (Continued)

(51) Int. Cl.
*B01L 3/00* (2006.01)
*G01N 27/14* (2006.01)

(52) U.S. Cl.
CPC ... *B01L 3/502715* (2013.01); *B01L 3/502707* (2013.01); *B01L 3/502723* (2013.01);
(Continued)

(58) Field of Classification Search
CPC ......... B01L 3/502715; B01L 3/502707; B01L 3/502723; B01L 2200/04;
(Continued)

(56) References Cited

U.S. PATENT DOCUMENTS 4,511,359 A * 4/1985 Vaillancourt ......... A61M 39/14
604/905
5,589,136 A 12/1996 Northrup et al.
(Continued)

FOREIGN PATENT DOCUMENTS

| CN | 101981445 | 2/2011 |
|---|---|---|
| CN | 102004126 | 4/2011 |

(Continued)

OTHER PUBLICATIONS

International Search Report and Written Opinion for PCT/US2019/067080 dated Feb. 28, 2020.
(Continued)

*Primary Examiner* — P. Kathryn Wright
*Assistant Examiner* — Curtis A Thompson
(74) *Attorney, Agent, or Firm* — Knobbe, Martens, Olson & Bear, LLP

(57) ABSTRACT

The present application is generally directed to systems, methods, and devices for diagnostics for sensing and/or identifying pathogens, genomic materials, proteins, and/or other small molecules or biomarkers. In some implementations, a small footprint low cost device provides rapid and robust sensing and identification. Such a device may utilize microfluidics, biochemistry, and electronics to detect one or more targets at once in the field and closer to or at the point
(Continued)

of care. In some implementations, the systems and methods herein implement a reader device, an assay cartridge, and a mobile or external device configured to receive a biological sample, test the biological sample, and provide test results to a patient or user associated with the patient. The test results may be packaged with additional information, including symptoms suffered by the patient, a diagnosis, and follow-up instructions. In some embodiments, the test results may also be provided with or aggregated with other test results to generate aggregate information.

3 Claims, 50 Drawing Sheets

Related U.S. Application Data on Apr. 9, 2019, provisional application No. 62/783,104, filed on Dec. 20, 2018.

(52) U.S. Cl.
CPC .......... *G01N 27/14* (2013.01); *B01L 2200/04* (2013.01); *B01L 2200/0684* (2013.01); *B01L 2200/12* (2013.01); *B01L 2200/16* (2013.01); *B01L 2300/042* (2013.01); *B01L 2300/0645* (2013.01); *B01L 2300/0681* (2013.01); *B01L 2300/0867* (2013.01); *B01L 2300/0887* (2013.01); *B01L 2400/0478* (2013.01); *B01L 2400/06* (2013.01)

(58) Field of Classification Search
CPC ......... B01L 2200/0684; B01L 2200/12; B01L 2200/16; B01L 2300/042; B01L 2300/0645; B01L 2300/0681; B01L 2300/0867; B01L 2300/0887; B01L 2400/0478; B01L 2400/06; B01L 2200/025; B01L 2200/0605; B01L 2200/10; B01L 2300/021; B01L 2300/047; B01L 2300/049; B01L 3/502738; B01L 7/52; B01L 2200/027; B01L 2300/046; B01L 2300/0816; B01L 2300/0838; B01L 2300/0864; B01L 2300/087; B01L 2300/123; B01L 2300/1827; B01L 2400/0406; B01L 2400/0481; B01L 2400/0487; B01L 2400/0655; B01L 3/50273; G01N 27/14; C12Q 1/68; Y02A 90/10
See application file for complete search history.

(56) References Cited

U.S. PATENT DOCUMENTS

| 5,833,630 | A * | 11/1998 | Kloth | A61B 5/150022 |
| | | | | 604/509 |
| 6,403,367 | B1 | 6/2002 | Cheng et al. |
| 6,524,532 | B1 | 2/2003 | Northrup |
| 6,576,459 | B2 | 6/2003 | Miles et al. |
| 6,602,473 | B1 | 8/2003 | Northrup |
| 6,699,713 | B2 | 3/2004 | Benett et al. |
| 6,875,602 | B2 | 4/2005 | Gutierrez |
| 7,062,385 | B2 | 6/2006 | White et al. |
| 7,135,294 | B2 | 11/2006 | Lee |
| 7,157,050 | B2 | 1/2007 | Yazawa et al. |
| 7,172,896 | B2 | 2/2007 | Cheng et al. |
| 7,483,805 | B2 | 1/2009 | Sparks et al. |
| 7,708,944 | B1 | 5/2010 | Sadik et al. |
| 7,915,030 | B2 | 3/2011 | Inoue et al. |
| 8,078,408 | B2 | 12/2011 | Albert et al. |
| 8,106,428 | B2 | 1/2012 | Koh et al. |
| 8,133,671 | B2 | 3/2012 | Williams et al. |
| 8,173,077 | B2 | 5/2012 | Korampally et al. |
| 8,283,155 | B2 | 10/2012 | Holmes et al. |
| 8,329,453 | B2 | 12/2012 | Battrell et al. |
| 8,354,074 | B2 | 1/2013 | Silverbrook et al. |
| 8,370,070 | B2 | 2/2013 | Fernandez |
| 8,383,064 | B2 | 2/2013 | Azimi et al. |
| 8,414,844 | B2 | 4/2013 | Sadik et al. |
| 8,431,389 | B2 | 4/2013 | Battrell et al. |
| 8,431,390 | B2 | 4/2013 | Jovanovich et al. |
| 8,480,980 | B2 | 7/2013 | Yoo |
| 8,524,490 | B2 | 9/2013 | Lipscomb et al. |
| 8,614,059 | B2 | 12/2013 | Young |
| 8,716,007 | B2 | 5/2014 | Battrell et al. |
| 8,841,076 | B2 | 9/2014 | Holmes et al. |
| 8,865,075 | B2 | 10/2014 | Guzman |
| 8,865,401 | B2 | 10/2014 | Young et al. |
| 8,883,487 | B2 | 11/2014 | Collier et al. |
| 8,951,472 | B2 | 2/2015 | Kellner et al. |
| 8,956,858 | B2 | 2/2015 | Dineen et al. |
| 9,029,168 | B2 | 5/2015 | McAlpine et al. |
| 9,376,713 | B2 | 6/2016 | Bashir et al. |
| 9,921,182 | B2 | 3/2018 | Pennathur et al. |
| 10,196,678 | B2 | 2/2019 | Pennathur et al. |
| 10,626,448 | B2 | 4/2020 | Pennathur et al. |
| 11,465,141 | B2 | 10/2022 | Pierson et al. |
| 11,473,128 | B2 | 10/2022 | Pennathur et al. |
| 2002/0067174 | A1 | 6/2002 | McAllister |
| 2004/0132059 | A1 | 7/2004 | Scurati et al. |
| 2004/0166504 | A1 | 8/2004 | Rossier et al. |
| 2004/0170530 | A1 | 9/2004 | Hefti |
| 2005/0274612 | A1 | 12/2005 | Segawa |
| 2006/0176179 | A1 | 8/2006 | Skorpik et al. |
| 2006/0177842 | A1 | 8/2006 | Wangh |
| 2007/0031283 | A1* | 2/2007 | Davis ................. A61B 5/15087 |
| | | | | 422/400 |
| 2007/0141605 | A1 | 6/2007 | Vann et al. |
| 2007/0243634 | A1 | 10/2007 | Pamula et al. |
| 2007/0298487 | A1 | 12/2007 | Bachur et al. |
| 2008/0308846 | A1 | 12/2008 | Shim et al. |
| 2009/0061450 | A1 | 3/2009 | Hunter |
| 2010/0041056 | A1 | 2/2010 | Kinnon et al. |
| 2010/0075311 | A1 | 3/2010 | Barrault et al. |
| 2010/0075312 | A1 | 3/2010 | Davies et al. |
| 2010/0105035 | A1 | 4/2010 | Hashsham et al. |
| 2010/0193378 | A1 | 8/2010 | Bratov et al. |
| 2010/0200400 | A1 | 8/2010 | Revol-Cavalier |
| 2010/0216225 | A1 | 8/2010 | Dyer et al. |
| 2010/0240044 | A1 | 9/2010 | Kumar et al. |
| 2010/0243449 | A1 | 9/2010 | Oliver |
| 2010/0261286 | A1 | 10/2010 | Kim et al. |
| 2011/0039261 | A1 | 2/2011 | Hillebrand et al. |
| 2011/0068015 | A1 | 3/2011 | Park |
| 2011/0086352 | A1 | 4/2011 | Bashir et al. |
| 2011/0091879 | A1 | 4/2011 | Hillebrand et al. |
| 2011/0136104 | A1 | 6/2011 | Pregibon et al. |
| 2011/0165572 | A1 | 7/2011 | O'Halloran |
| 2011/0244467 | A1 | 10/2011 | Haswell |
| 2011/0275162 | A1 | 11/2011 | Xie et al. |
| 2011/0312073 | A1 | 12/2011 | Silverbrook et al. |
| 2011/0312074 | A1 | 12/2011 | Azimi et al. |
| 2011/0312610 | A1 | 12/2011 | Azimi et al. |
| 2011/0312657 | A1 | 12/2011 | Azimi et al. |
| 2011/0312683 | A1 | 12/2011 | Silverbrook et al. |
| 2011/0312791 | A1 | 12/2011 | Silverbrook et al. |
| 2011/0312826 | A1 | 12/2011 | Silverbrook et al. |
| 2011/0312841 | A1 | 12/2011 | Silverbrook et al. |
| 2011/0318728 | A1 | 12/2011 | Phan et al. |
| 2012/0052562 | A1 | 3/2012 | Silverbrook et al. |
| 2012/0053088 | A1 | 3/2012 | Azimi et al. |
| 2012/0058547 | A1 | 3/2012 | Hsing et al. |
| 2012/0064523 | A1 | 3/2012 | Ecker et al. |
| 2012/0129709 | A1 | 5/2012 | Zhang |
| 2012/0150004 | A1 | 6/2012 | Currie et al. |
| 2012/0183965 | A1 | 6/2012 | Ward et al. |
| 2012/0168306 | A1 | 7/2012 | Hassibi et al. |
| 2012/0329144 | A1 | 12/2012 | Kwak |
| 2013/0011912 | A1 | 1/2013 | Battrell et al. |
| 2013/0029333 | A1 | 1/2013 | Son et al. |

(56) References Cited

U.S. PATENT DOCUMENTS

| | | |
|---|---|---|
| 2013/0079254 A1 | 3/2013 | Azimi et al. |
| 2013/0085680 A1 | 4/2013 | Arlen et al. |
| 2013/0101990 A1 | 4/2013 | Handique et al. |
| 2013/0109021 A1 | 5/2013 | Hwang |
| 2013/0109022 A1 | 5/2013 | Hwang |
| 2013/0115685 A1 | 5/2013 | Holmes et al. |
| 2013/0130369 A1 | 5/2013 | Wilson et al. |
| 2013/0137591 A1 | 5/2013 | Clemens et al. |
| 2013/0143775 A1 | 6/2013 | Lee |
| 2013/0154671 A1 | 6/2013 | Lee |
| 2013/0183750 A1 | 7/2013 | Sadik et al. |
| 2013/0244898 A1 | 9/2013 | Burd et al. |
| 2013/0252320 A1 | 9/2013 | Burd et al. |
| 2013/0267016 A1 | 10/2013 | Niemz et al. |
| 2013/0273528 A1 | 10/2013 | Ehrenkranz |
| 2013/0280725 A1 | 10/2013 | Ismagilov et al. |
| 2013/0309676 A1 | 11/2013 | Layne |
| 2013/0309679 A1 | 11/2013 | Ismagilov et al. |
| 2014/0050620 A1 | 2/2014 | Johnson et al. |
| 2014/0072962 A1 | 3/2014 | Kelley et al. |
| 2014/0099636 A1 | 4/2014 | Lee |
| 2014/0102915 A1 | 4/2014 | Hu |
| 2014/0170646 A1 | 6/2014 | Kelley et al. |
| 2014/0186935 A1 | 7/2014 | Yoo |
| 2014/0194305 A1 | 7/2014 | Kayyem et al. |
| 2014/0206562 A1 | 7/2014 | McCormack et al. |
| 2014/0272941 A1* | 9/2014 | Gunnerson ......... B01L 3/50273 435/7.1 |
| 2014/0287414 A1 | 9/2014 | Chung et al. |
| 2014/0329244 A1 | 11/2014 | Ding et al. |
| 2014/0335527 A1 | 11/2014 | Goel |
| 2014/0349298 A1 | 11/2014 | Stanchina et al. |
| 2014/0349381 A1 | 11/2014 | Battrell et al. |
| 2015/0041315 A1 | 2/2015 | Jack |
| 2015/0041317 A1 | 2/2015 | Chan |
| 2015/0041328 A1 | 2/2015 | Chan |
| 2015/0041336 A1 | 2/2015 | Chan |
| 2015/0044679 A1 | 2/2015 | Jack |
| 2015/0045254 A1 | 2/2015 | Jack |
| 2015/0064707 A1 | 3/2015 | Collier |
| 2015/0093304 A1 | 4/2015 | Guzman |
| 2015/0104792 A1 | 4/2015 | Mazumdar et al. |
| 2015/0111287 A1 | 4/2015 | Rawle |
| 2015/0141264 A1 | 5/2015 | Jung et al. |
| 2015/0141268 A1 | 5/2015 | Rothberg et al. |
| 2015/0330927 A1 | 11/2015 | Lee et al. |
| 2015/0346105 A1* | 12/2015 | Gutsell ..................... B01L 7/52 435/287.2 |
| 2016/0097739 A1 | 4/2016 | Pennathur |
| 2016/0097740 A1 | 4/2016 | Pennathur |
| 2016/0097741 A1 | 4/2016 | Pennathur |
| 2016/0097742 A1 | 4/2016 | Pennathur |
| 2016/0129437 A1 | 5/2016 | Kayyem et al. |
| 2016/0130639 A1 | 5/2016 | Pennathur |
| 2016/0362748 A1 | 12/2016 | Mongan et al. |
| 2017/0039339 A1 | 2/2017 | Bitran et al. |
| 2017/0113221 A1 | 4/2017 | Hoffman et al. |
| 2018/0135117 A1 | 5/2018 | Link |
| 2018/0169658 A1 | 6/2018 | Lei et al. |
| 2019/0228247 A1 | 7/2019 | Schueren et al. |
| 2019/0232282 A1* | 8/2019 | Pierson ................ C12Q 1/6825 |
| 2020/0277660 A1 | 9/2020 | Pennathur et al. |
| 2022/0048031 A1 | 2/2022 | Chiang et al. |
| 2022/0056511 A1 | 2/2022 | Gaiteri et al. |
| 2022/0073975 A1 | 3/2022 | Fang et al. |
| 2022/0250054 A1 | 8/2022 | Wade |

FOREIGN PATENT DOCUMENTS

| | | |
|---|---|---|
| CN | 205538786 U | 8/2016 |
| EP | 2003446 | 12/2008 |
| GB | 6197905 | 4/2022 |
| GB | 6197906 | 4/2022 |
| GB | 6197907 | 4/2022 |
| JP | S59-139624 | 8/1984 |
| JP | H11-241977 | 9/1999 |
| JP | 2001-527220 | 12/2001 |
| JP | 2008-532005 | 8/2008 |
| JP | 2011-517769 | 6/2011 |
| JP | 2012-501627 | 1/2012 |
| JP | 2012-177599 | 9/2012 |
| JP | 2016-527510 | 9/2016 |
| KR | 10-2005-0024340 | 3/2005 |
| KR | 10-2009-0101764 | 9/2009 |
| TW | 2007-45551 | 12/2007 |
| TW | 2013-33188 | 8/2013 |
| WO | WO 1999/033559 | 7/1999 |
| WO | WO 2009/018642 | 2/2009 |
| WO | WO 2009/119971 | 10/2009 |
| WO | WO 2010/111605 | 9/2010 |
| WO | WO 2012/142192 | 10/2012 |
| WO | WO 2015/015175 | 2/2015 |
| WO | WO 2015/058008 | 4/2015 |
| WO | WO 2016/064635 | 4/2016 |
| WO | WO 2016/100335 | 6/2016 |
| WO | WO 2016/129894 | 8/2016 |
| WO | WO 2017/106790 | 6/2017 |
| WO | WO 2017/147486 | 8/2017 |
| WO | WO 2018/017884 | 1/2018 |
| WO | WO-2018057647 A1 * | 3/2018 ........ B01L 3/502715 |
| WO | WO 2018/085151 A1 | 5/2018 |
| WO | WO 2020/132008 | 6/2020 |

OTHER PUBLICATIONS

Extended European Search Report dated Jan. 31, 2023 in European Application No. 19899952.6.

Abdelhalim et al., "Dielectric constant, electrical conductivity and relaxation time measurements of different gold nanoparticle sizes", International Journal of the Physical Sciences, 6 :5487-5491 (2011).

Andersen et al., "Surface-dependent chemical equilibrium constants and capacitances for bare and 3-10 cyanopropyldimethylchlorosilane coated silica nanochannels" J. Colloid Interface Sci. 353:301-310 (2011).

Angayarkanni et al., "Effect of nanoparticles aggregation on thermal and electrical conductivities of nanofluids", Journal of Nanofluids, 3: 17-25 (2014).

Arruebo et al., "Antibody-Conjugated Nanoparticles for Biomedical Applications", Journal of Nanomaterials 2009:Article ID 439389.

Backer et al., "Planar and 3D interdigitated electrodes for biosensing applications: The impact of a dielectric barrier on the sensor properties" Phys. Status Solidi A, 1-7 (2014).

Bhat, "Salinity (conductivity) sensor based on parallel plate capacitors" Thesis, 2005, Univ. South Florida.

Brito-Neto et al., "Understanding Capacitively Coupled Contactless Conductivity Detection in Capillary and Microchip Electrophoresis. Part 1. Fundamentals" Electroanalysis 2005, 17, No. 13.

Coltro et al., "Capacitively coupled contactless conductivity detection on microfluidic systems—ten years of development" Anal. Methods, 2012, 4, 25.

Coltro et al., "Microfluidic devices with integrated dual-capacitively coupled contactless conductivity detection to monitor binding events in realtime" Sensors and Actuators B 192 (2014) 239-246.

"Conductivity Theory and Practice" Radiometer analytical SAS, 2004.

Credo et al., "Label-free electrical detection of pyrophosphate generated from DNA polymerase reactions on field-effect devices", Analyst 137:1351-1362 (2011).

Damen et al., "Characterization of the quantitative HCV NASBA assay", J. Virol. Methods, 82, 45-54 (1999).

Fang et al., "Integrated biochip for label-free and real-time detection of NDA amplification by contactless impedance measurements based on interdigitated electrodes", 2013, 44, 241-247.

Felhofer et al., "Recent developments in instrumentation for capillary electrophoresis and microchip-capillary electrophoresis", Eletrophoresis, 31(15): 2469-2486 (2010).

(56) References Cited

OTHER PUBLICATIONS

Fox et al., "Development and evaluation of nucleic acid sequence based amplification (NASBA) for diagnosis of enterovirus infections using the NucliSens Basic Kit", J. Clin. Virol., 24:117-130 (2002).

Ghaith, "Development of a reverse transcription loop-mediated isothermal amplification assay for rapid detection of foot-and-mouth disease virus", Master of Science Thesis, Aug. 2018.

Haldar, "Pyrophosphato-Complexes of Nickel and Cobalt in Solution" Nature 4226:744-745 (1950).

Hilland, "Simple sensor system for measuring the dielectric properties of saline solutions" Meas. Sci. Technol. 8 (1997) 901-910.

Hsieh et al., "Rapid, Sensitive and Quantitative Detection of Pathogenic DNA at the Point of Care via Microfluidic Electrochemical Quantitative Loop-Mediated Isothermal Amplification (MEQ-LAMP)" Angew Chem Intl Ed Engl 51(20):4896-4900 (2012).

Imai et al., "Rapid diagnosis of H5N1 avian influenza virus infection by newly developed influenza H5 hemagglutinin gene-specific loop mediated isothermal amplification method", J. Virol. Methods 141:173-180 (2007).

International Search Report for PCT/US2019/067134 dated Apr. 1, 2020, in 4 pages.

International Search Report for PCT/US2019/067077 dated Apr. 21, 2020, in 4 pages.

International Search Report for PCT/US2019/067082 dated May 11, 2020, in 5 pages.

Jensen et al., "Hydronium-domination ion transport in carbon-dioxide-saturated electrolytes at low salt concentrations in nanochannels" Phys. Review E. 83:5 (2011), 056307.

Kim et al., "Chemosensors for pyrophosphate", Accounts of Chemical Research 42: 23-31 (2009).

Kuban et al., "A review of the recent achievements in capacitively coupled contactless conductivity detection" Analytica Chimica Acta 607 (2008) 15-29.

Kuban et al., "Contactless conductivity detection for analytical techniques: Developments from 2010 to 2012" Electrophoresis 2013, 34, 55-69.

Kuban et al., "Effects of the cell geometry and operating parameters on the performance of an external contactless conductivity detector for microchip electrophoresis" Lab Chip, 2005, 5, 407-415.

Lasia, "Electrochemical Impedance Spectroscopy and Its Applications", Modern Aspects of Electrochemistry, B. E. Conway, J. Bockris, and R.E. White, Edts., Kluwer Academic/Plenum Publishers, New York, 1999, vol. 32, p. 143-248.

Lee et al., "A fluorescent confirmation method for DNA amplification in PCR through a fluorescent pyrophosphate sensor", Bull. Korean Chem. Soc. 29: 497-498 (2007).

Lima et al., "Contactless conductivity biosensor in microchip containing folic acid as bioreceptor" Lab Chip, 2012, 12, 1963-1966.

Lima et al., "Highly sensitive contactless conductivity microchips based on concentric electrodes for flow analysis" Chem. Commun., 2013, 49, 11382.

Liu et al., "Fluorescence Turn on Chemosensors for Ag+ and Hg2+ based on tetraphenylethylene Motif Featuring Adenine and Thymine Moieties", Organic Letters 10(20):4581-4584 (2008).

Lu et al., "Plasmonic-based electrochemical impedance spectroscopy: application to molecular binding", Anal Chem. 84: 327-333 (2012).

Macdonald et al., "Fundamentals of impedance spectroscopy" Chapter1, Impedance Spectroscopy, Second Edition, edited by Evgenij Barsoukov and J. Ross Macdonald (2005).

Mahabadi et al., "Capacitively coupled contactless conductivity detection with dual top-bottom cell configuration for microchip electrophoresis". Electrophoresis 2010, 31, 1063-1070.

Maier et al, "An impedimetric sensor for real-time detection of antibiotic resistance genes employing rolling circle amplification", Int. J. Electrochem. Sci International Journal, 2015, 2026-2034.

Mori et al, "Detection of Loop-Mediated Isothermal Amplification Reaction by Turbidity Derived from Magnesium Pyrophosphate Formation" Biochemical and Biophysical Research Communications 289:150-154 (2001).

Mori et al, "Real-time turbidimetry of LAMP reaction for quantifying template DNA" J. Biochem Biphys Methods 59:145-157 (2004).

Morre et al., "Monitoring of chlamydia trachomatis infections after antibiotic treatment using rnA detection by nucleic acid sequence based amplification", J. Clin. Pathol.: Clin. Mol. Pathol. 51:149-154 (1998).

Murphy et al., "Multicenter comparison of Roche COBAS AMPLICOR MONITOR Version 1.5, Organon Teknika NucliSens QT with Extractor, and Bayer Quantiplex Version 3.0 for Quantification of Human Immunodeficiency Virus Type 1 RNA in Plasma", J. Clin. Microbiol., 38: 4034-4041 (2000).

Nagamine et al, "Accelerated reaction by loop-mediated isothermal amplification using loop primers" Molecular and Cellular Probes 16:223-229 (2002).

Nakamura et al, "Detection of Six Single-Nucleotide Polymorphisms Associated with Rheumatoid Arthritis by a Loop-Mediated Isothermal Amplification Method and an Electrochemical DNA Chip" Anal Chem 79:9484-9493 (2007).

Notomi et al, "Loop-mediated isothermal amplification of DNA" Nucleic Acids Res 25(12): i-vii (2000).

Opekar et al., "Contactless Impedance Sensors and Their Application to Flow Measurements" Sensors 2013, 13, 2786-2801.

Parida et al., et al., "Development and evaluation of reverse transcription-loop-mediated isothermal amplification assay for rapid and real-time detection of Japanese encephalitis virus", J. Clin. Microbiol., 44:4172-4178 (2006).

Parida et al., "Rapid and real-time detection of chikungunya virus by reverse transcription loop-mediated isothermal amplification assay", J. Clin. Microbiol., 45: 351-357 (2007).

Parida et al., "Real-time reverse transcription loop-mediated isothermal amplification for rapid detection of West Nile Virus", J. Clin. Microbiol., 42: 257-263 (2004).

Parida et al., "Rapid detection and differentiation of dengue virus serotypes by a real-time reverse transcription-loop-mediated isothermal amplification assay", J. Clin. Microbiol., 43: 2895-2903 (2005).

Pennathur et al, "Low Temperature Fabrication and Surface Modification Methods for Fused Silica Micro- and Nanochannels," MRS Proceedings, 1659:15-26 (2014). doi: 10.1557/opl.2014.32.

Pourhassan-Moghaddam et al., "Protein detection through different platforms of immune-loop-mediated isothermal amplification", Nanoscale Research Letters, 8:485-496 (2013).

Pumera et al., "Contactless Conductivity Detector for Microchip Capillary Electrophoresis" Anal. Chem. 2002, 74, 1968-1971.

Pumera, "Contactless conductivity detection for microfluidics: Designs and applications" Talanta 74 (2007) 358-364.

Raistrick et al., "Theory" Chapter2, Impedance Spectroscopy, Second Edition, edited by Evgenij Barsoukov and J. Ross Macdonald (2005).

Ramos et al., "A Four-Terminal Water-Quality-Monitoring Conductivity Sensor". IEEE Transactions on Instrumentation and Measurement, vol. 57, No. 3, Mar. 2008.

Rana et al., "Comparison of Planar and 3-D Interdigitated Electrodes as Electrochemical Impedance Biosensors" Electroanalysis 2011, 23, No. 10, 2485-2490.

Rana et al., "Impedance spectra analysis to characterize interdigitated electrodes as electrochemical sensors" Electrochimica Acta 56 (2011) 8559-8563.

Rosenfeld et al., Lab on a Chip: 100-fold sample on paper-based microfluidic devices, Lab Chip http:pubs.rsc.org/en/content/articlelanding/2014/lc/c41c00734d (2014).

Schwartz et at, "Microfluidic Assay for Continuous Bacteria Detection Using Antimicrobial Peptides and Isotachophoresis" Anal Chem 86:10106-10113 (2014).

Simon et al., "Label-Free Detection of DNA Amplification in Droplets Using Electrical Impedance" 15th International Conference on Miniaturized Systems for Chemistry and Life Sciences Oct. 2-6, 2011, Seattle, Washington, USA, pp. 1683-1685.

(56) References Cited

OTHER PUBLICATIONS

Tanyanyiwa et al., "High-Voltage Capacitively Coupled Contactless Conductivity Detection for Microchip Capillary Electrophoresis" Anal. Chem. 2002, 74, 6378-6382.

Thai et al, "Development and evaluation of a novel loop-mediated isothermal amplification method for rapid detection of severe acute respiratory syndrome coronavirus", J. Clin. Microbiol., 42:1956-1961 (2004).

Tomita et al, "Loop-mediated isothermal amplification (LAMP) of gene sequences and simple visual detection of products" Nature Protocols 3(5):877-822 (2008).

Tomsic et al., "Conductivity of Magnesium Sulfate in Water from 5 to 35° C. and from Infinite Dilution to Saturation" Journal of Solution Chemistry, vol. 31, No. 1, Jan. 2002.

Vincent et al., "Helicase-dependent isothermal DNA amplification", EMBO Rep., 5: 795-800 (2004).

Wang et al., "Microchip enzymatic assay of organophosphate nerve agents" Analytica Chimica Acta 505 (2004) 183-187.

Wang et al., "Recombinase Polymerase Amplification Assay—A Simple, Fast and Cost-Effective Alternative to Real Time PCR for Specific Detection of Feline Herpesvirus-1" PLOS ONE, Jan. 2017, pp. 1-8, vol. 12, No. 1.

Xie et al, "Development of an electrochemical method for Ochratoxin A detection based on aptamer and loop-mediated isothermal amplification" Biosensors and Bioelectronics 55:324-329 (2014).

Yan et al., "Isothermal amplified detection of DNA and RNA", Mol. BioSyst., 10: 970-1003 (2014).

Zawrah et al., "Stability and electrical conductivity of water-base Al2O3 nanofluids for different amplifications", HBRC Journal 12:227-234 (2016).

Zhang et al., "Detection of human cytomegalovirus pp67 late gene transcripts in cerebrospinal fluid of human immunodeficiency virus type 1-infected patients by nucleic acid sequence-based amplification", J. Clin. Microbiol., 38: 1920-1925 (2000).

Zhang et al, "Quantitative determination of target gene with electrical sensor", Scientific Reports, 5(1):12539 (2015).

Extended European Search Report for Application No. EP 19899953. 4, dated Sep. 9, 2022, in 9 pages.

Partial European Search Report in Application No. 19900777.4, dated Oct. 21, 2022, in 16 pages.

Wang et al., "Two methods for increased specificity and sensitivity in loop-mediated isothermal amplification", Molecules, vol. 20(4):6048-6059, retrieved from internet https://www.ncbi.nlm.nih.gov/pmc/articles/PMC627222/pdf/molecules-20-06048.pdf (2015).

Xinxin et al., "Integrated biochip for label-free and real-time detection of DNA amplification by contactless impedance measurements based on interdigitated electrodes", Biosensors and Bioelectronics, vol. 44:241-247 (2013).

International Search Report and Written Opinion for PCT/US2021/45610 mailed on Feb. 4, 2022, in 19 pages.

International Search Report and Written Opinion for PCT/US2021/45608 mailed on Feb. 4, 2022, in 19 pages.

International Search Report and Written Opinion for PCT/US2021/45596, mailed on Nov. 15, 2021, in 14 pages.

International Search Report and Written Opinion for PCT/US2021/45600, mailed on Feb. 17, 2022, in 16 pages.

Phillips et al., "Strand displacement probes combined with isothermal nucleic acid amplification for instrument-free detection from complex samples", Anal. Chem. vol. 90(11):6580-6586 (Apr. 18, 2018).

Wang et al., "Towards disposable lab-on-a-chip: Poly(methylmethacrylate) microchip electrophoresis device with electrochemical detection", Electrophoresis vol. 23:596-601 (2002).

Zhang et al., "Monitoring the progression of loop-mediated isothermal amplification using conductivity", Analytical Biochemistry, vol. 466:16-18 (2014).

\* cited by examiner

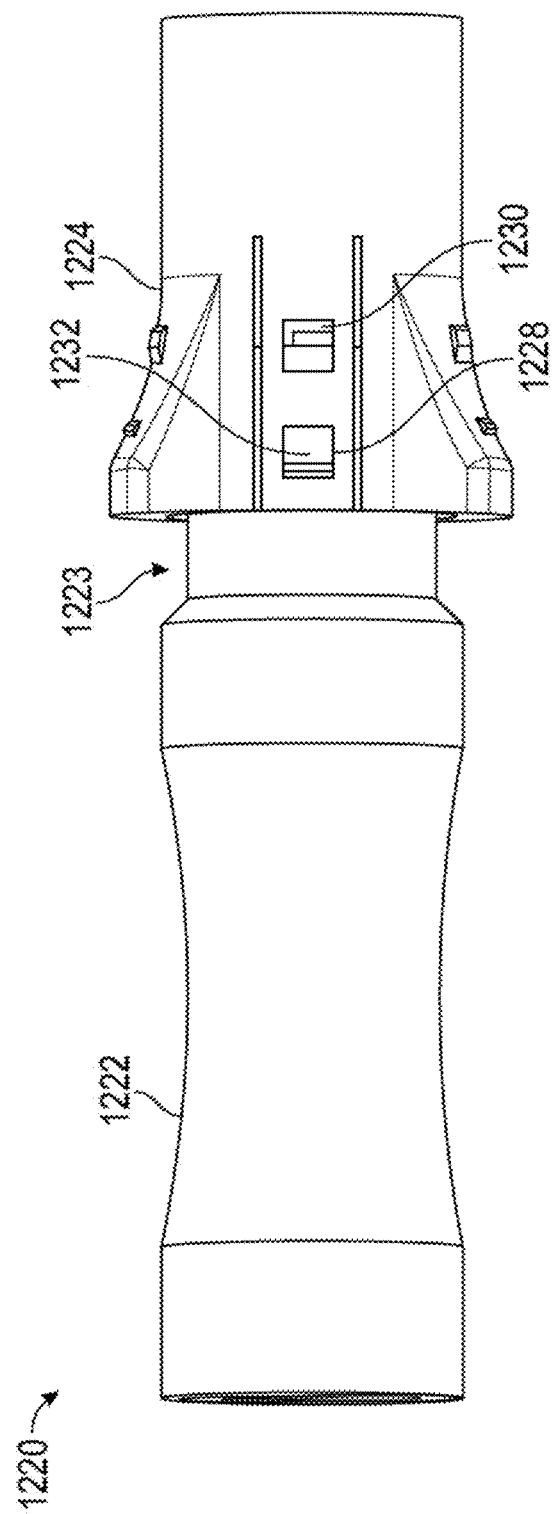

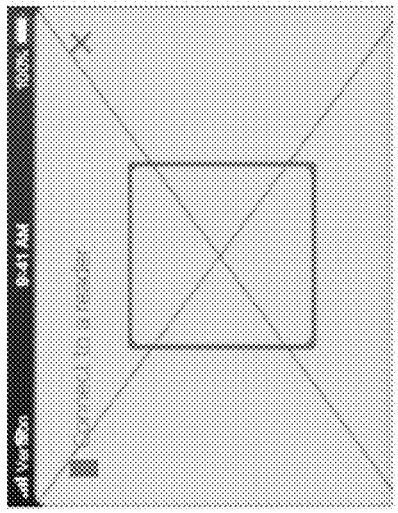
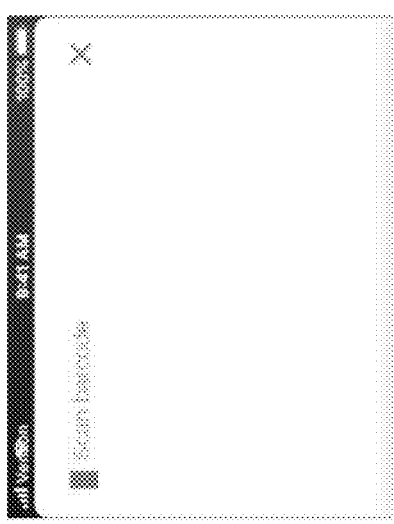
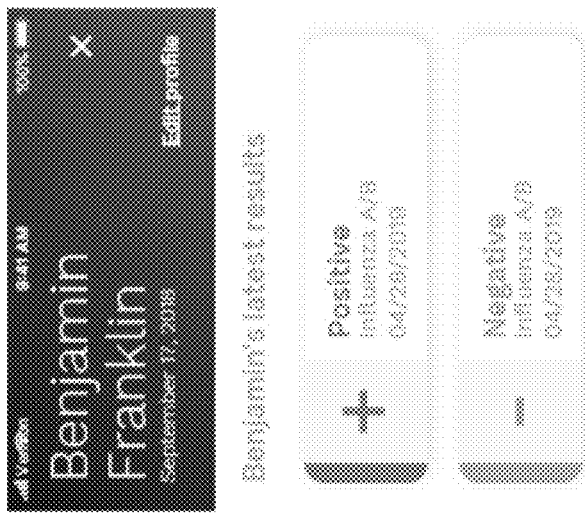
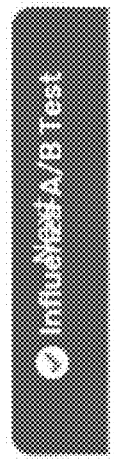
FIG. 15E   FIG. 15F   FIG. 15G

HANDHELD IMPEDANCE-BASED DIAGNOSTIC TEST SYSTEM FOR DETECTING ANALYTES

CROSS REFERENCE TO RELATED APPLICATIONS

This application is a U.S. National Phase Application of PCT International Application Number PCT/US2019/067080, filed on Dec. 18, 2019, designating the United States of America and published in the English language, which is an International Application of and claims the benefit of priority to U.S. Provisional Application No. 62/783,104, filed on Dec. 20, 2018, U.S. provisional Application No. 62/831,387, filed Apr. 9, 2019, and U.S. provisional Application No. 62/931,079, filed Nov. 5, 2019. The disclosures of the above-referenced applications are hereby expressly incorporated by reference in their entireties.

Some embodiments provided herein include embodiments disclosed in Int. App. Pub. No. WO 2016/057422, U.S. 2016/0097740, 2016/0097741, U.S. 2016/0097739, U.S. 2016/0097742, U.S. 2016/0130639; and Int. App. Pub. No. WO 2018/057647 which claims priority to U.S. App No. 62/398,959, U.S. App No. 62/399,047, U.S. App No. 62/398,925, U.S. App No. 62/398,913, U.S. App No. 62/398,955, and U.S. App No. 62/398,965, which are each expressly incorporated by reference in its entirety.

This application is related to U.S. App No. 62/782,610, filed on Dec. 20, 2018 and entitled METHODS AND COMPOSITIONS TO REDUCE NONSPECIFIC AMPLIFICATION IN ISOTHERMAL AMPLIFICATION REACTIONS; U.S. App No. 62/783,117, filed on Dec. 20, 2018 and entitled ISOTHERMAL AMPLIFICATION WITH ELECTRICAL DETECTION; U.S. App No. 62/783,051, filed on Dec. 20, 2018 and entitled METHODS AND COMPOSITIONS FOR DETECTION OF AMPLIFICATION PRODUCTS; U.S. App No. 62/783,104, filed December 2018 and entitled HANDHELD IMPEDANCE-BASED DIAGNOSTIC TEST SYSTEM FOR DETECTING ANALYTES; and U.S. App No. 62/831,387, filed on Apr. 9, 2019 and entitled HANDHELD IMPEDANCE-BASED DIAGNOSTIC TEST SYSTEM FOR DETECTING ANALYTES. The entirety of each of these related applications is hereby expressly incorporated by reference for all purposes.

FIELD

The present application is generally directed to systems, methods, and devices for diagnostics for sensing and/or identifying pathogens, genomic materials, proteins, and/or other small molecules or biomarkers. In some implementations, a small, portable, low-power device provides rapid and robust sensing and identification. Such a device may utilize microfluidics, biochemistry, and electronics to detect one or more targets in the field and closer to or at the point of care.

BACKGROUND

Pathogens in a sample may be identified by detecting specific genomic material (DNA or RNA). Beyond pathogen detection, many other biomarkers are available for testing, including molecules that provide early detection of cancer, vital prenatal information, or a greater understanding of a patient's microbiome. In conventional nucleic acid testing ("NAT"), genomic material in a sample may first be exponentially copied using a molecular amplification process known as the polymerase chain reaction ("PCR") until the quantity of DNA present is great enough to be measurable. In the case of RNA, the genomic material of many viruses, an additional step can be included to first transcribe the RNA into DNA before amplifying by PCR.

SUMMARY

In a first embodiment, an assay cartridge for containing a sample comprising a target agent for detection by a reader device comprises a cartridge body configured to be received by the reader device, and a cap configured to hold the sample carrier containing the sample. The cartridge body includes a test well containing an excitation electrode and a sensing electrode, wherein the test well is configured to contain at least a portion of the sample comprising the target agent undergoing an amplification process; a sample introduction area configured to receive a sample carrier containing the sample; and a fluid path fluidically coupling the sample introduction area to the test well. The cap is further configured to mechanically couple to the cartridge body, wherein mechanically coupling the cap to the cartridge body causes compression of a trapped volume of a fluid to drive at least a portion of the sample through the fluid path into the test well.

In some embodiments, the sample carrier comprises a capillary tube, and the cap comprises a retaining well having an interior diameter larger than an exterior diameter of the capillary tube; and a retaining structure disposed within the retaining well and configured to retain the capillary tube at a position spaced from a side interior wall and a rear interior wall of the retaining well to form at least one air channel fluidically coupled to an inner end of the capillary tube. In some embodiments, the cap further comprises a plunger disposed about at least a portion of the retaining well, and the sample introduction area of the cartridge body comprises a capillary tube receiving well configured to sealingly receive an outer end of the capillary tube to fluidically couple an inner lumen of the capillary tube to the fluid path when the cap is mechanically coupled to the cartridge body; and a plunger receiving well configured to sealingly receive the plunger when the cap is mechanically coupled to the cartridge body, wherein, as the cap is mechanically coupled to the cartridge body, the plunger compresses a volume of air within the plunger receiving well, such that the air flows through the air channel and forces the sample to travel into the fluid path of the cartridge body. In some embodiments, the cartridge body comprises a base and a translucent cover, the translucent cover comprising a planar surface defining one side of at least one of the test well and the fluid path. In some embodiments, the cartridge body further comprise a hollow plunger comprising an interior space fluidically coupled to the fluid path of the cartridge body, wherein the cap comprises a plunger receiving well configured to sealingly receive the hollow plunger, and, as the cap is mechanically coupled to the cartridge body, the plunger compresses a volume of air within the plunger receiving well, such that the air flows through the hollow plunger and forces the sample to travel into the fluid path of the cartridge body. In some embodiments, the cartridge body comprises at least a second test well containing an excitation electrode and a sensing electrode, and a second fluid path fluidically coupling the sample introduction area to the second test well, wherein the second test well is configured to contain at least a portion of the sample comprising the target agent undergoing an amplification process. In some embodiments, the cartridge body comprises a base and a printed circuit board (PCB), the PCB comprising a planar surface defining one side of at least one of the test well and the fluid path. In some embodiments, the PCB comprises a heating element configured to heat the test well. In some embodiments, the PCB comprises the excitation electrode and the sensing electrode. In some embodiments, the test well is configured to mix a reagent and the sample into a substantially evenly mixed test fluid. In some embodiments, the reagent comprises one or more dried reagents stored within the test well. In some embodiments, the cartridge body comprises a plurality of test wells, and at least a first test well of the plurality of test wells stores a reagent different from a reagent stored in a second test well of the plurality of test wells. In some embodiments, the cartridge body comprises a plurality of test wells, and at least two test wells of the plurality of test wells store the same reagent. In some embodiments, the cartridge body further comprises a mixing chamber positioned between the sample introduction area and the test well along the fluid path, the mixing chamber configured to mix a reagent and the sample into a substantially evenly mixed test fluid. In some embodiments, the reagent comprises one or more dried reagents stored within the mixing chamber. In some embodiments, the assay cartridge further comprises a first electrode interface including a first contact pad leading to the excitation electrode and a second contact pad leading to the sensing electrode. In some embodiments, the assay cartridge further comprises a gas-permeable, liquid-impermeable vent fluidically coupled to the test well. In some embodiments, the assay cartridge further comprises a machine-readable cartridge identifier printed thereon, the cartridge identifier associated with one or more test protocols. In some embodiments, the assay cartridge is a disposable single-use assay cartridge. In some embodiments, the trapped volume of a fluid comprises air.

In a second embodiment, a detection system for detecting a target agent comprises a reader device, an assay cartridge, and a power cartridge. The reader device includes a cavity configured to receive cartridges; a memory storing at least computer-readable instructions; a processor in communication with the memory; and an electrode interface in communication with the processor. The assay cartridge includes an external portion; an internal portion configured to fit within the cavity of the reader device, the internal portion including an electrode interface configured to establish an electrical connection with the electrode interface of the reader device when the assay cartridge is inserted into the reader device; and a flow path configured to sealingly enclose a fluid sample within the assay cartridge. The power cartridge includes an internal portion configured to fit within the cavity; and circuitry disposed at least partially on the internal portion and configured to establish an electrical connection with the electrode interface when the power cartridge is inserted into the reader device. Inserting the power cartridge into the cavity causes the reader device to power off, and removing the power cartridge from the cavity causes the reader device to power on.

In some embodiments, the reader device further includes a communication module configured to connect to a remote computing device executing a user interface application. In some embodiments, the remote computing device is wirelessly connected to the reader device. In some embodiments, the remote computing device is connected to the reader device by at least one of WiFi or Bluetooth. In some embodiments, the reader device does not include a user interface. In some embodiments, the reader device includes a visual status indicator on an exterior portion of the reader device. In some embodiments, the visual status indicator comprises one or more light emitting diodes. In some embodiments, the visual status indicator comprises a plurality of differently colored light emitting diodes. In some embodiments, the visual status indicator comprises a plurality of individually controllable light emitting diodes. In some embodiments, the visual status indicator comprises a ring of lights at least partially surrounding the cavity of the reader device. In some embodiments, the visual status indicator is configured to indicate at least one of a ready status, a testing status, a completed testing status, an error status, and a wireless pairing status.

In some embodiments, the assay cartridge or system is for use in detecting a target agent. In some embodiments, the target agent is a nucleic acid, preferably a nucleic acid of a pathogen. In some embodiments, the sample is a biological sample obtained from a subject, such as a human.

In some embodiments, a method of using the assay cartridge or system for detecting a target agent comprises contacting a biological sample from a subject, preferably a human, with the assay cartridge or system; and detecting the presence of the target agent. In some embodiments, the target agent is a nucleic acid, preferably a nucleic acid of a pathogen. In some embodiments, the target agent is a nucleic acid and the assay cartridge or system or method further comprises amplifying the nucleic acid, such as by Loop-Mediated Isothermal Amplification (LAMP) and measuring or analyzing a modulation of an electrical signal, such as impedance or capacitance, which is desirably compared to a control.

In some embodiments of the assay cartridge, system, or method, the assay cartridge is configured to be used in determining an impedance or a capacitance using three-terminal sensing or four-terminal sensing. In some embodiments of the assay cartridge, the test well further contains a third electrode. In some embodiments, the third electrode is disposed between the excitation electrode and the sensing electrode. In some embodiments, the test well further contains a fourth electrode. In some embodiments, the third electrode and the fourth electrode are disposed between the excitation electrode and the sensing electrode.

In another embodiment, an assay cartridge for analyzing a sample comprising a target agent is described. The assay cartridge comprises a cartridge body and a reagent blister. The cartridge body is configured to be received by a reader device. The cartridge body includes at least one test well containing an excitation electrode and a sensing electrode, wherein the at least one test well is configured to contain at least a portion of the sample comprising the target agent undergoing an amplification process, a sample introduction area configured to receive a sample carrier containing the sample, and a fluid path fluidically coupling the sample introduction area to the test well. The reagent blister is configured to hold a reagent to be mixed with the sample prior to the amplification process. The reagent blister is further configured to be ruptured when the cartridge body is inserted into the reader device. The rupturing of the reagent blister produces a force that mixes the reagent with the sample and drives at least a portion of the reagent and at least the portion of the sample through the fluid path to the at least one test well.

In another embodiment, a detection system for detecting a target agent is disclosed. The detection system comprises a reader device, an assay cartridge, and a mobile device. The reader devices includes a cavity configured to receive cartridges, a memory storing at least computer-readable instructions, a processor in communication with the memory, a communication interface, and an electrode interface in communication with the processor and electrodes of the cartridges. The assay cartridge includes an external portion, an internal portion configured to fit within the cavity of the reader device, the internal portion including electrodes configured to establish an electrical connection with the electrode interface of the reader device when the assay cartridge is inserted into the reader device, a flow path configured to fluidically couple a sample introduction area of the assay cartridge to at least one test well of the assay cartridge, and a reagent store configured to store a reagent for mixing with a sample prior to conveying at least a portion of a mixture of the reagent and the sample to the at least one test well. The mobile device includes a data store storing at least computer-readable instructions for the mobile device, a hardware processor in communication with the memory, an interface for identifying a type of assay cartridge, and a wireless communication interface in communication with the processor. The mobile device is configured to identify the type of the assay cartridge and communicate parameters for an analysis of the sample by the reader device to the reader device via the wireless communication interface.

In another embodiment, a method for identifying a target in a sample is described. The method comprises depositing the sample into a sample receptacle of a disposable cartridge, inserting the disposable cartridge into a cartridge receptacle of an analyzer device, and rupturing a reagent blister containing at least one reagent. The method further comprises generating a mixture by mixing the at least one reagent with the sample, conveying at least a portion of the mixture to at least one testing well comprising at least one dried enzyme and/or a detection agent, such as a set of, primers, antibody or binding fragment thereof, increasing a temperature of the at least one testing well, and measuring an electrical characteristic of at least the portion of the mixture in the at least on testing well. Insertion of the disposable cartridge into the cartridge receptacle causes the rupturing of the reagent blister, the generating of the mixture, and the conveying of at least the portion of the mixture to the at least one testing well. Preferred additional alternatives are set forth below.

1. An additional alternative comprises an assay cartridge for containing a sample comprising a target agent for detection by a reader device, the assay cartridge comprising: a cartridge body configured to be received by the reader device, the cartridge body including: a test well containing an excitation electrode and a sensing electrode, wherein the test well is configured to contain at least a portion of the sample comprising the target agent undergoing an amplification process; a sample introduction area configured to receive a sample carrier containing the sample; and a fluid path fluidically coupling the sample introduction area to the test well; and a cap configured to hold the sample carrier containing the sample, the cap further configured to mechanically couple to the cartridge body, wherein mechanically coupling the cap to the cartridge body causes compression of a trapped volume of a fluid to drive at least a portion of the sample through the fluid path into the test well.

2. The assay cartridge of alternative 1, wherein the sample carrier comprises a capillary tube, and wherein the cap comprises: a retaining well having an interior diameter larger than an exterior diameter of the capillary tube; and a retaining structure disposed within the retaining well and configured to retain the capillary tube at a position spaced from a side interior wall and a rear interior wall of the retaining well to form at least one air channel fluidically coupled to an inner end of the capillary tube.

3. The assay cartridge of alternative 2, wherein the cap further comprises a plunger disposed about at least a portion of the retaining well, and wherein the sample introduction area of the cartridge body comprises: a capillary tube receiving well configured to sealingly receive an outer end of the capillary tube to fluidically couple an inner lumen of the capillary tube to the fluid path when the cap is mechanically coupled to the cartridge body; and a plunger receiving well configured to sealingly receive the plunger when the cap is mechanically coupled to the cartridge body, wherein, as the cap is mechanically coupled to the cartridge body, the plunger compresses a volume of air within the plunger receiving well, such that the air flows through the air channel and forces the sample to travel into the fluid path of the cartridge body.

4. The assay cartridge of any one of alternatives 1-3, wherein the cartridge body comprises a base and a translucent cover, the translucent cover comprising a planar surface defining one side of at least one of the test well and the fluid path.

5. The assay cartridge of alternative 1, wherein the cartridge body further comprise a hollow plunger comprising an interior space fluidically coupled to the fluid path of the cartridge body, wherein the cap comprises a plunger receiving well configured to sealingly receive the hollow plunger, and wherein, as the cap is mechanically coupled to the cartridge body, the plunger compresses a volume of air within the plunger receiving well, such that the air flows through the hollow plunger and forces the sample to travel into the fluid path of the cartridge body.

6. The assay cartridge of alternative 5, wherein the cartridge body comprises at least a second test well containing an excitation electrode and a sensing electrode, and a second fluid path fluidically coupling the sample introduction area to the second test well, wherein the second test well is configured to contain at least a portion of the sample comprising the target agent undergoing an amplification process.

7. The assay cartridge of any one of alternatives 5 and 6, wherein the cartridge body comprises a base and a printed circuit board (PCB), the PCB comprising a planar surface defining one side of at least one of the test well and the fluid path.

8. The assay cartridge of alternative 7, wherein the PCB comprises a heating element configured to heat the test well.

9. The assay cartridge of any one of alternatives 7 and 8, wherein the PCB comprises the excitation electrode and the sensing electrode.

10. The assay cartridge of any one of alternatives 5-9, wherein the test well is configured to mix a reagent and the sample into a substantially evenly mixed test fluid.

11. The assay cartridge of alternative 10, wherein the reagent comprises one or more dried reagents stored within the test well.

12. The assay cartridge of alternative 11, wherein the cartridge body comprises a plurality of test wells, and wherein at least a first test well of the plurality of test wells stores a reagent different from a reagent stored in a second test well of the plurality of test wells.

13. The assay cartridge of any one of alternatives 11 and 12, wherein the cartridge body comprises a plurality of test wells, and wherein at least two test wells of the plurality of test wells store the same reagent.

14. The assay cartridge of any one of alternatives 1-13, wherein the cartridge body further comprises a mixing chamber positioned between the sample introduction area and the test well along the fluid path, the mixing chamber configured to mix a reagent and the sample into a substantially evenly mixed test fluid.

15. The assay cartridge of alternative 14, wherein the reagent comprises one or more dried reagents stored within the mixing chamber.

16. The assay cartridge of any one of alternatives 1-15, further comprising a first electrode interface including a first contact pad leading to the excitation electrode and a second contact pad leading to the sensing electrode.

17. The assay cartridge of any one of alternatives 1-16, further comprising a gas-permeable, liquid-impermeable vent fluidically coupled to the test well.

18. The assay cartridge of any one of alternatives 1-17, further comprising a machine-readable cartridge identifier printed thereon, the cartridge identifier associated with one or more test protocols.

19. The assay cartridge of any one of alternatives 1-18, wherein the assay cartridge is a disposable single-use assay cartridge.

20. The assay cartridge of any one of alternatives 1-19, wherein the trapped volume of a fluid comprises air.

21. A detection system for detecting a target agent, the system comprising: a reader device including: a cavity configured to receive cartridges; a memory storing at least computer-readable instructions; a processor in communication with the memory; and an electrode interface in communication with the processor; an assay cartridge including: an external portion; an internal portion configured to fit within the cavity of the reader device, the internal portion including an electrode interface configured to establish an electrical connection with the electrode interface of the reader device when the assay cartridge is inserted into the reader device; and a flow path configured to sealingly enclose a fluid sample within the assay cartridge; and a power cartridge including: an internal portion configured to fit within the cavity; and circuitry disposed at least partially on the internal portion and configured to establish an electrical connection with the electrode interface when the power cartridge is inserted into the reader device, wherein inserting the power cartridge into the cavity causes the reader device to power off, and wherein removing the power cartridge from the cavity causes the reader device to power on.

22. The system of alternative 21, wherein the reader device further includes a communication module configured to connect to a remote computing device executing a user interface application.

23. The system of alternative 22, wherein the remote computing device is wirelessly connected to the reader device.

24. The system of any one of alternatives 22 and 23, wherein the remote computing device is connected to the reader device by at least one of WiFi or Bluetooth.

25. The system of any one of alternatives 21-24, wherein the reader device does not include a user interface.

26. The system of any one of alternatives 21-25, wherein the reader device includes a visual status indicator on an exterior portion of the reader device.

27. The system of alternative 26, wherein the visual status indicator comprises one or more light emitting diodes.

28. The system of alternative 27, wherein the visual status indicator comprises a plurality of differently colored light emitting diodes.

29. The system of any one of alternatives 26-28, wherein the visual status indicator comprises a plurality of individually controllable light emitting diodes.

30. The system of any one of alternatives 26-29, wherein the visual status indicator comprises a ring of lights at least partially surrounding the cavity of the reader device.

31. The system of any one of alternatives 26-30, wherein the visual status indicator is configured to indicate at least one of a ready status, a testing status, a completed testing status, an error status, and a wireless pairing status.

32. The assay cartridge or system of any one of alternatives claims 1-31 for use in detecting a target agent.

33. The assay cartridge or system of alternative 32, wherein the target agent is a nucleic acid, preferably a nucleic acid of a pathogen.

34. The assay cartridge or system of anyone of alternatives 32 or 33, wherein the sample is a biological sample obtained from a subject, such as a human.

35. A method of using the assay cartridge or system of any one of alternatives 1-31 for detecting a target agent comprising: contacting a biological sample from a subject, preferably a human, with the assay cartridge or system of any one of claims 1-30; and detecting the presence of the target agent.

36. The method of alternative 35, wherein the target agent is a nucleic acid, preferably a nucleic acid of a pathogen.

37. The assay cartridge or system of anyone of alternatives 32-34 or the method of any one of alternatives 35 or 36, wherein the target agent is a nucleic acid and the assay cartridge or system or method further comprises amplifying the nucleic acid, such as by Loop-Mediated Isothermal Amplification (LAMP) and measuring or analyzing a modulation of an electrical signal, such as impedance or capacitance, which is desirably compared to a control.

38. The assay cartridge, system, or method of any one of alternatives 1-37, wherein the assay cartridge is configured to be used in determining an impedance or a capacitance using three-terminal sensing or four-terminal sensing.

39. The assay cartridge of any one of alternatives 1-20, wherein the test well further contains a third electrode.

40. The assay cartridge of alternative 39, wherein the third electrode is disposed between the excitation electrode and the sensing electrode.

41. The assay cartridge of alternative 39, wherein the test well further contains a fourth electrode.

42. The assay cartridge of alternative 41, wherein the third electrode and the fourth electrode are disposed between the excitation electrode and the sensing electrode.

43. An assay cartridge for analyzing a sample comprising a target agent, the assay cartridge comprising: a cartridge body configured to be received by a reader device, the cartridge body including: at least one test well containing an excitation electrode and a sensing electrode, wherein the at least one test well is configured to contain at least a portion of the sample comprising the target agent undergoing an amplification process; a sample introduction area configured to receive a sample carrier containing the sample; and a fluid path fluidically coupling the sample introduction area to the test well; and a reagent blister configured to hold a reagent to be mixed with the sample prior to the amplification process, the reagent blister further configured to be ruptured when the cartridge body is inserted into the reader device, wherein the rupturing of the reagent blister produces a force that mixes the reagent with the sample and drives at least a portion of the reagent and at least the portion of the sample through the fluid path to the at least one test well.

44. A detection system for detecting a target agent, the system comprising: a reader device including: a cavity configured to receive cartridges; a memory storing at least computer-readable instructions; a processor in communication with the memory; a communication interface; and an electrode interface in communication with the processor and electrodes of the cartridges; an assay cartridge including: an external portion; an internal portion configured to fit within the cavity of the reader device, the internal portion including electrodes configured to establish an electrical connection with the electrode interface of the reader device when the assay cartridge is inserted into the reader device; a flow path configured to fluidically couple a sample introduction area of the assay cartridge to at least one test well of the assay cartridge; and a reagent store configured to store a reagent for mixing with a sample prior to conveying at least a portion of a mixture of the reagent and the sample to the at least one test well; and a mobile device including: a data store storing at least computer-readable instructions for the mobile device; a hardware processor in communication with the memory; an interface for identifying a type of assay cartridge; and a wireless communication interface in communication with the processor, wherein the mobile device is configured to identify the type of the assay cartridge and communicate parameters for an analysis of the sample by the reader device to the reader device via the wireless communication interface.

45. The system of alternative 44, wherein the reader device is further configured to generate test results comprising a determination whether the target agent is present in the sample.

46. The system of any one of alternatives 44 and 45, wherein the mobile device is further configured to display a prompt for one or more symptoms experienced by a patient that provides the sample and receive the one or more symptoms experienced by the patient.

47. The system of alternative 46, wherein the mobile device comprises a user interface configured to prompt for and receive the one or more symptoms.

48. The system of any one of alternatives 46 and 47, wherein the one or more symptoms are selected from a list or entered by the user.

49. The system of any one of alternatives 46-48, wherein the user interface is further configured to provide instructions for collecting the sample for testing, loading the sample into the assay cartridge, and inserting the assay cartridge into the reader device.

50. The system of any one of alternatives 46-49, wherein the mobile device is further configured to receive the one or more symptoms before, while, or after the reader device determines whether the target agent is present in the sample.

51. The system of any one of alternatives 46-50, wherein the reader device is further configured to analyze the test results and the one or more symptoms to diagnose whether the patient is suffering from an ailment.

52. The system of any one of alternatives 46-51, wherein each of the one or more symptoms has associated therewith a sliding scale value representative of a severity of the symptom.

53. The system of any one of alternatives 46-52, wherein the mobile device is further configured to allow the user to compare previous test results for the patient with current test results.

54. The system of any one of alternatives 46-53, wherein the mobile device is further configured to display, to the user, information from the reader device, the information comprising a time remaining before the test results are generated, an identifier of the reader device, and an identifier of the assay cartridge.

55. The system of any one of alternatives 44-54, wherein the mobile device is further configured to display, to the user, test results for the sample, any symptoms associated with the sample, an indication of the diagnosed ailment, and one or more of a recommended follow-up steps for the diagnosed ailment.

56. The system of any one of alternatives 51-55, wherein the mobile device is further configured to share electronically the test results, the one or more symptoms, or the diagnosed ailment with another entity.

57. The system of any one of alternatives 46-56, wherein the mobile device is further configured to determine that the patient is a carrier for a disease based on test results positive for the target agent and no reported symptoms.

58. The system of any one of alternatives 46-57, wherein at least one of the one or more symptoms is weighted higher than one or more other symptoms of the one or more symptoms.

59. The system of any one of alternatives 46-58, wherein a threshold number of the one or more symptoms, weighting of each of the one or more symptoms, and specific symptoms of the one or more symptoms used to diagnose the ailment is determined based on one or more metrics.

60. The system of alternative 59, wherein the one or more metrics is received from one or more of the Center for Disease Control (CDC) or a national organization that monitors illnesses.

61. The system of any one of alternatives 46-60, wherein the mobile device is further configured to generate a score indicator representative of a probability that the patient is ill.

62. The system of any one of alternatives 46-61, wherein the score indicator falls within a range of 0 to 100, where 0 is a low probability that the patient is ill and 100 is a high probability that the patient is ill 63. The system of any one of alternatives 46-62, wherein the mobile device is further configured to identify an illness that the patient is suffering from based on negative test results for the target agent and the one or more symptoms of the patient.

64. The system of any one of alternatives 46-63, further comprising an aggregating device that aggregates information from multiple mobile devices, the multiple mobile devices comprising the mobile device, and wherein the mobile device is further configured to determine that the patient is ill based on the test results, symptoms, and the aggregated information from the multiple mobile devices.

65. The system of any one of alternatives 46-64, wherein the mobile device is further configured to automatically perform one or more actions based on a determination that the patient is ill.

66. The system of alternative 65, wherein the one or more actions comprises generating and sending an alert to one or more of the patient, to the user, to attending medical staff, to the CDC, and to family of the patient.

67. The system of alternative 66, wherein the alert comprises one or more of a phone call, a text message, an e-mail message, a push message, an audio message, a flashing indicator, or audible indicator.

68. The system of alternative 64, wherein the aggregating device is further configured to track illnesses over a geographic area based on information received from the multiple mobile devices.

69. The system of alternative 68, wherein the aggregating device is further configured to generate a heat map of the illnesses over the geographic area.

70. The system of any one of alternatives 68 and 69, wherein the aggregating device is further configured to track quantities of available vaccines or medications and to compare a quantity of available vaccines or medications with a quantity of illnesses to determine whether sufficient vaccines or medications are available to treat or prevent the spread of the illnesses.

71. The system of alternative 70, wherein the aggregating device is further configured to automatically generate a request to vaccine and/or medication suppliers to increase the quantity of available vaccines or medications when insufficient vaccines or medications are available.

72. The system of any one of alternatives 64-71, wherein the mobile device is further configured to display any information tracked or generated by the aggregating device.

73. The system of any one of alternatives 44-72, wherein the samples comprises a biological secretion.

74. The system of alternative 73, wherein the biological secretion comprises blood, mucus, or saliva.

75. A method for identifying a target in a sample, the method comprising: depositing the sample into a sample receptacle of a disposable cartridge; inserting the disposable cartridge into a cartridge receptacle of an analyzer device; rupturing a reagent blister containing at least one reagent; generating a mixture by mixing the at least one reagent with the sample; conveying at least a portion of the mixture to at least one testing well comprising at least one dried enzyme and/or a detection agent, such as a set of, primers, antibody or binding fragment thereof; increasing a temperature of the at least one testing well; and measuring an electrical characteristic of at least the portion of the mixture in the at least on testing well, wherein insertion of the disposable cartridge into the cartridge receptacle causes the rupturing of the reagent blister, the generating of the mixture, and the conveying of at least the portion of the mixture to the at least one testing well.

BRIEF DESCRIPTION OF THE DRAWINGS

FIGS. 11A-111D depict a mechanical fluid transfer mechanism of the example cartridge of FIGS. 10A-10K.

FIGS. 12A-12I depict an example cartridge for detection of a target that can be used in conjunction with the handheld systems disclosed herein.

DETAILED DESCRIPTION

Figure 1A:
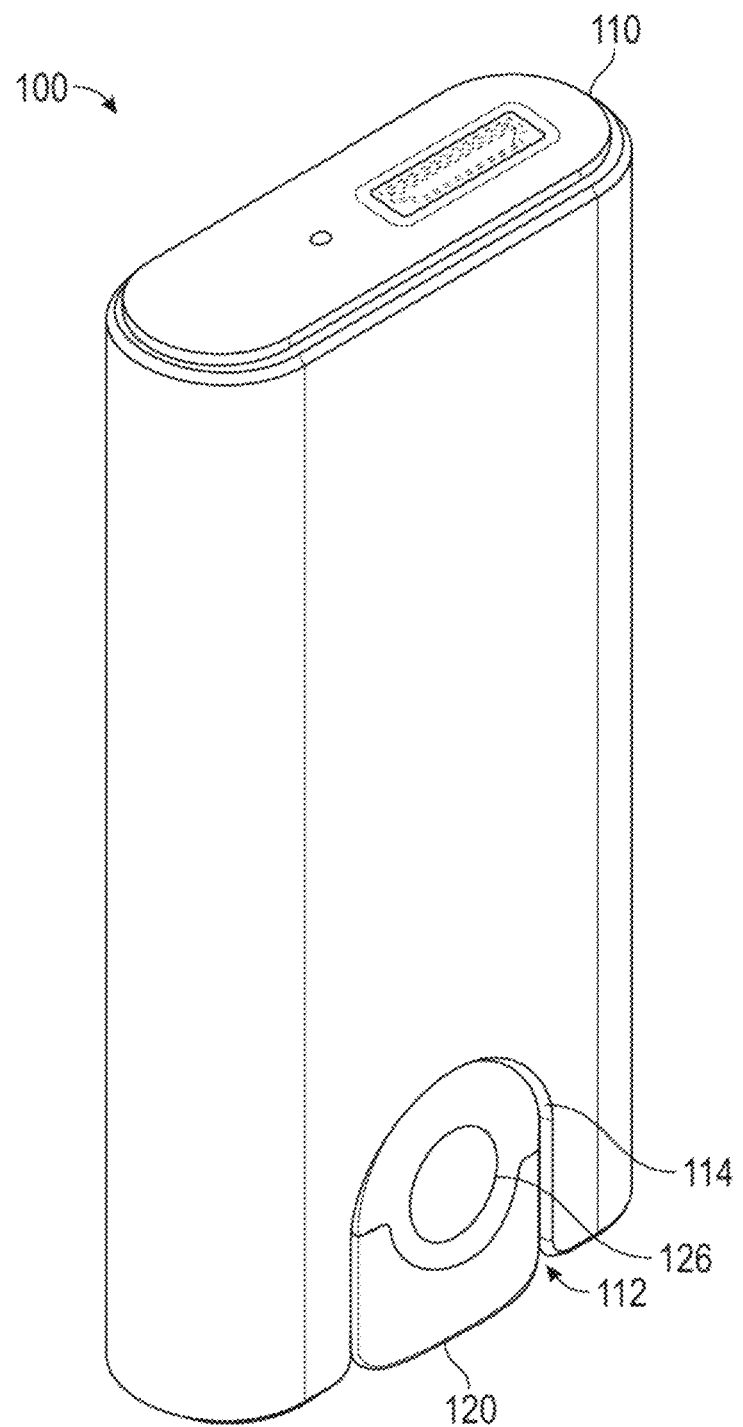
FIGS. 1A-1C depict an example handheld system for detection of a target.

Aspects of the disclosure herein concern the use of amplification and contactless electrical sensing to detect the presence of a target in a sample. Such a diagnostic platform may replace the complex optical systems and expensive fluorescent labels used for optical detection and the electrodes and electroactive agents used in existing electrochemical and FET techniques with common electronic components. In some aspects, the amplification can be isothermal. The platform described herein is inexpensive, robust, portable, and consumes less power than traditional diagnostic systems. In some aspects, the diagnostic platform is small enough to fit in the palm of a consumer's hand and capable of performing in the field, for example, a diagnosis in a doctor's office, in the home, in a location remote from a medical facility.

Many commercially available nucleic acid detection platforms utilize traditional PCR, thereby requiring temperature cycling, fluorescent labels and optical detection instrumentation. These factors result in expensive, lab-based instrumentation which employ delicate, vibration sensitive detectors, costly fluorescent markers, and have a large footprint. The equipment requires operation, and frequent calibration, by highly trained personnel.

These large, unwieldy platforms make routine use of conventional NAT challenging to use in the clinic, much less in the home. NAT remains a costly and slow strategy closely tied to centralized laboratory facilities. The presently disclosed technology, in contrast, avoids these challenges.

A hurdle to point of care ("POC") testing is the potential inhibition of amplification by interferents often encountered in crude, unprocessed clinical samples such as whole blood, saliva, mucus, or any other bodily fluid or biological component. The mitigation of amplification inhibitors may challenge the direct detection of target nucleic acids from clinically relevant biologic samples. As described herein, a sample may comprise one or more of blood, saliva, mucus, or any other bodily fluid or biological secretion or component.

Traditional detection strategies commonly rely on fluorescence detection techniques. Such techniques may be complex, more expensive, and require precision optical systems. The present disclosure however, generally relies on electrical detection systems. Such electrical detection systems may leverage microelectronics that consume relatively low power and can be manufactured at a reduced cost due to high volume manufacturing. Thus, electrical detection of genomic material may transfer the advances of the computer industry to bioassay sensing.

Existing electronic methods for monitoring amplification may require the binding of an electrochemically active label or the selective binding of the amplified material to a surface. However, when used in real world clinical applications, these techniques often suffer from slow response times, biofouling of the electrode or binding surfaces resulting in poor signal to noise ratios, and limitations on the lifetime and reliability of the device. While potentially enabling great sensitivity, the use of electrochemical or field effect transistor "FET" detection adds a layer of complexity to the detection. This can result in more expensive and less robust strategies than POC and other consumer applications typically dictate. Accordingly, the need for additional diagnostic devices is manifest.

The platform disclosed herein relies on measurement of the change in electrical conductivity that occurs during nucleic acid amplification. In sum, during biochemical synthesis of DNA from nucleotide triphosphates, the number and the mobility of electrically charged molecules are altered. This, in turn, results in a change in the solution conductivity as amplification progresses. This change in solution electrical conductivity may be sensed using frequency-dependent capacitively coupled contactless conductivity detection ("fC$^4$D").

In some implementations, fC$^4$D uses a pair of electrodes in close proximity to, but not in contact with, a fluid disposed in an amplification chamber to measure the solution's electrical properties. The ability to measure the properties of the solution in this way, without direct contact, avoids the challenges of surface fouling common to other electrical measurement methods.

In some implementations, utilizing fC$^4$D, a high-frequency alternating current ("AC") signal is applied to the excitation electrode. This signal is capacitively coupled through the solution where it is detected at the signal electrode. By comparing the excitation signal with the signal at the signal electrode, the solution's conductivity can be determined.

Informed by high-resolution finite element models and empirical studies, specific tolerances of fC$^4$D based technology may achieve the optimal detection sensitivity and dynamic sensing range for particular implementations of the platform. Such calculated and empirically determined parameters of microfluidic dimensions, capacitive coupling characteristics, and the applied frequency can enable the determination of the effective parameters for detecting solution conductivity changes. In some embodiments, the parameters corresponding to optimal detection can be interdependent variables. According to the following equation, the measured impedance is a function of the solution resistance, capacitance and the applied frequency:

$$Z=R-(1/pi*f*C)*j$$

As the thickness of the electrode passivation layer increases, a parasitic capacitance due to this layer consequently increases. The optimal AC frequency with which to measure solution conductivity by fC$^4$D therefore can be chosen with respect to the capacitance of the passivation layer.

Overview of Example Cartridges, Readers, and Signal Processing

In some aspects, a system for detecting a target in a sample includes a removable fluidics cartridge that is couplable to a companion reader device. A user can apply a sample to the cartridge and then insert it into the reader device. The reader device is configured for performing the testing procedures using the cartridge and analyzing the test data to determine the presence, absence, or quantity of a target in the sample. For example, the cartridge can be provided with the desired agents, proteins, or other chemical matter for an amplification process by which a target initially present in the sample is amplified. Specifically, some cartridges can be provided with the desired chemical matter for nucleic acid testing, wherein genomic material in the sample is exponentially copied using a molecular amplification process, as described herein. The cartridge can also include a test well for containing the amplification process, where a test well refers to a well, chamber, channel, or other geometry configured for containing (or substantially containing) test fluid and constituents of the amplification process. The reader device may maintain a desired temperature or other test environment parameters for the cartridge to facilitate the amplification process, and can electronically monitor a test well of the cartridge throughout some or all of the amplification process. The reader device can thus gather signal data representing the impedance of the test well over time during the amplification process, and can analyze the impedance as described herein to ascertain the presence, absence, or quantity of the target in the sample. As an example, the amplification process can range from five minutes to sixty minutes, with some examples ranging from ten minutes to thirty minutes. Preferably, in some embodiments, the amplification products are detected while being suspended in the fluid within the wells such that the amplification products are not attached or sequestered to the wells or fixed or bound to probes, which are bound to the wells. In other embodiments, the amplification products are detected as they are attached or sequestered to the wells e.g., fixed or bound to probes, which are bound to the wells.

Such systems can beneficially provide target detection performable in a clinical setting or even the home of a user, rather than requiring the sample to be sent to a laboratory for amplification and analysis. In the clinical setting, this can avoid the delays of conventional nucleic acid testing thereby enabling clinicians to determine diagnoses within the typical timeframe of a patient's office visit. As such, the disclosed systems enable clinicians to develop treatment plans for patients during their initial office visit, rather than requiring the clinician to wait for hours or even days to receive test results back from a laboratory. For example, when a patient visits a clinic a nurse or other healthcare practitioner can collect a sample from the patient and begin testing using the described system. The system can provide the test result by the time the patient consults with their doctor or clinician to determine a treatment plan. Particularly when used to diagnose pathologies that progress quickly, the disclosed systems can avoid the delays associated with laboratory testing that can negatively impact the treatment and outcome of the patient.

As another benefit, the disclosed systems can be used outside of the clinical setting (e.g., in the field, in rural settings without easy access to an established healthcare clinic) to detect health conditions such as contagious diseases (e.g., Ebola), thus enabling the appropriate personnel to take immediate action to prevent or mitigate the spread of a contagious disease. Similarly, the disclosed systems can be used in the field or at the site of a suspected hazardous contaminant (e.g., anthrax) to quickly determine whether a sample contains the hazardous contaminant, thus enabling the appropriate personnel to take immediate action to prevent or mitigate human exposure to the contaminant. Additionally, the disclosed systems can be used to detect contaminants in the blood or plasma supply or in the food industry. It will be appreciated that the disclosed systems can provide similar benefits in other scenarios in which real-time detection of a target enables more effective action than delayed detection through sending a sample to an off-site laboratory.

Another benefit of such systems is their use of low-cost, disposable single use cartridges together with a reusable reader device that can be used many times with different cartridges and/or for tests with different targets. In some embodiments disclosed herein, a single use cartridge includes a cartridge body and a cap which, when mechanically coupled together, create pressurized air that propels a collected sample from the cap into a mixing well and a test well of the cartridge body, reducing a necessary level of skill required to operate the reader device and reducing the complexity of both the cartridge and the reader device.

Figure 1B:
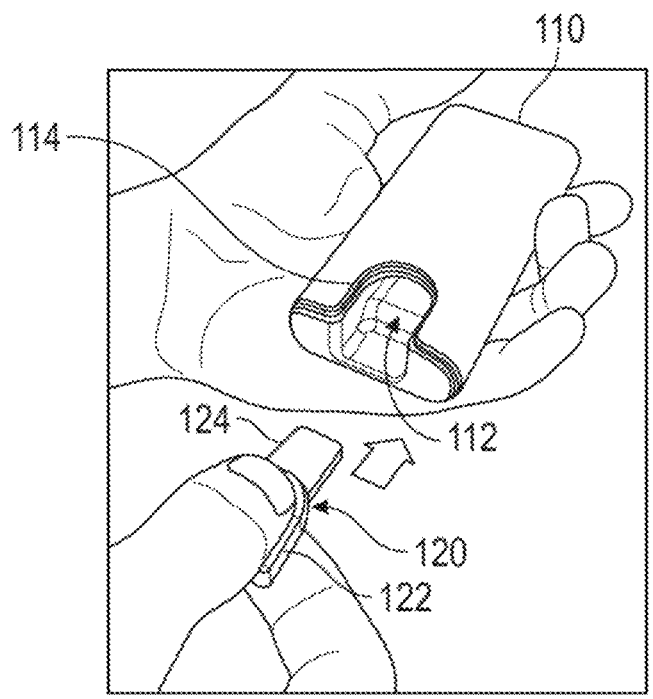
Figure 1C:
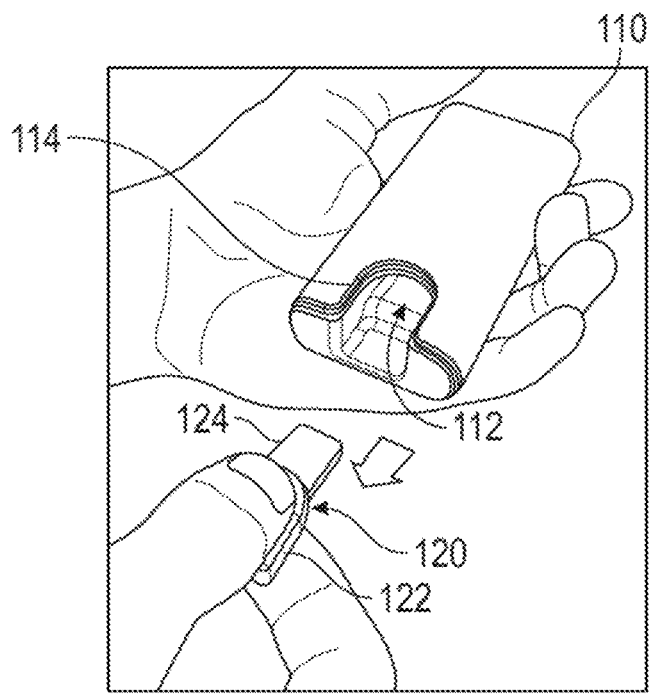

FIGS. 1A-1C depict an example handheld detection system 100 for detection of a target. The system 100 includes a reader device 110 and a cartridge 120 configured to fit within a cavity 112 of the reader device 110. The cartridge 120 generally includes an external section 122 and an internal section 124. When the cartridge 120 is inserted within the reader device 110, some or all of the internal section 124 is contained within the reader device 110. The external section 122 is sized and shaped to be gripped by a user and may include one or more three-dimensional surface features such as an indentation 126 to facilitate insertion and/or removal of the cartridge 120 from the reader device 110.

As shown in FIGS. 1B and 1C, the reader device 110 and the cartridge 120 are sized and shaped such that one or more interchangeable cartridges 120 can be inserted and/or removed by hand at the cavity 112. As will be described in greater detail, the reader device 110 can include one or more heating components configured to heat at least a portion of the internal section 124 of the cartridge 120. The reader device 110 can further include circuitry configured to connect with circuitry of the cartridge 120 to detect one or more electrical properties of a sample contained within the cartridge.

In some embodiments, some of the cartridges 120 can be power cartridges. The reader device 110 can be powered on and powered off by a power cartridge 120, instead of or in addition to a conventional power switch or button on the exterior of the reader device 110. A power cartridge 120 may have a size and shape similar to other cartridges for use with the reader device 110. In operation, the power cartridge 120 may be kept engaged within the cavity 112 when the reader device 110 is powered off. Circuitry of the power cartridge 120 can be in contact with internal circuitry of the reader device 110 such that removal of the power cartridge 120 from the reader device 110 causes the reader device 110 to power on for testing. After completion of one or more tests, or at any other time when the reader device 110 is to be powered off, the power cartridge 120 is inserted into the cavity 112. As the power cartridge 120 is inserted, the circuitry of the power cartridge 120 again comes into contact with the internal circuitry of the reader device 110 such that insertion of the power cartridge 120 causes the reader device 110 to power off. Power cartridge applications are discussed in greater detail with reference to FIG. 6.

In some embodiments, one or more external status indicators can be provided on an exterior portion of the reader device 110 to provide status indications to a user. For example, in one particular implementation the status indicator may include a light ring 114 disposed about the cavity 112. In other implementations, the optional status indicators may be located at any suitable location on the reader device 110. The light ring 114 or other status indicator may include one or more light sources, such as light emitting diodes (LEDs) or the like. The light ring may also be configured to indicate e.g., when the device is in use or not in use, or when different stages of the detection method using the device have been reached, completed, or are being performed, such as sample being received by the device or in the well(s), amplification being performed, detection of aggregates in the well(s), or transmission of the results to a receiver. Different colored lights can be used to indicate different stages of the detection method using the device such as those mentioned above.

In some embodiments, a plurality of differently colored LEDs may be provided within the light ring 114 or other status indicator in order to display a variety of status indications. For example, light ring 114 may include a combination of two or more colors (e.g., white, blue, and red), each of which may be independently activated. Each light source may be operated in a number of modes, such as a "solid" mode characterized by continuous activation of the light source (e.g., a steady "on" state), a "blinking" mode characterized by repeated activation and deactivation of the light source, a "flash" mode characterized by a single activation and deactivation of the light source, a "breathing" mode characterized by repeated gradual brightening and dimming of the light source, etc.

Combinations of colors and activation modes may be used to indicate the status of the reader device 100. For example, in some embodiments, the light ring 114 or other status indicator may display a first indication such as a solid white light when the reader device 100 is powered up and ready to receive an assay cartridge 120 (e.g., when a power cartridge is removed). Other examples of device status that may be indicated by the status indicator include, for example, a cartridge 120 is inserted into the reader device 110, a test has been started and is running, a test is complete, a cartridge is removed after completion of a test, an error (e.g., a test malfunction, premature removal of the cartridge 120, etc.), Bluetooth pairing, or any other status of the reader device 110. In one non-limiting example, a solid white light ring 114 indicates that a power cartridge has been removed and the device is powered up or that a test cartridge has been removed after completion of a test, a solid blue light ring 114 indicates that a test cartridge has been inserted into the reader device 110, a breathing blue light ring 114 indicates that a test has been started and is running, a breathing white light ring 114 indicates that a test is completed and the cartridge may be removed, a solid, breathing, or blinking red light ring indicates an error, a flash of blue and red at the light ring 114 indicates Bluetooth pairing in progress, and a steady, flashing, or blinking blue light ring 114 indicates Bluetooth pairing complete. It will be understood that other implementations may include any combination or subcombination of the status indicator modes listed above, and/or may include further status indications, light colors, operation modes, or the like.

FIGS. 2A-2F depict an example cartridge 200 configured for detection of a target. As described herein, the target may be a viral target, bacterial target, antigen target, parasite target, microRNA target, or agricultural analyte. Some embodiments of the cartridge 200 can be configured for testing for a single target, while some embodiments of the cartridge 200 can be configured for testing for multiple targets. The cartridge 200 includes a cartridge body 210 and a cap 240 configured to be mechanically coupled to the cartridge body 210. When the cartridge body 210 and the cap 240 are coupled together, the cartridge body 210 forms the internal section 204 of the cartridge 200 and a portion of the external section 202. The cap 240 forms a remaining portion of the external section 202.

Figure 2A:
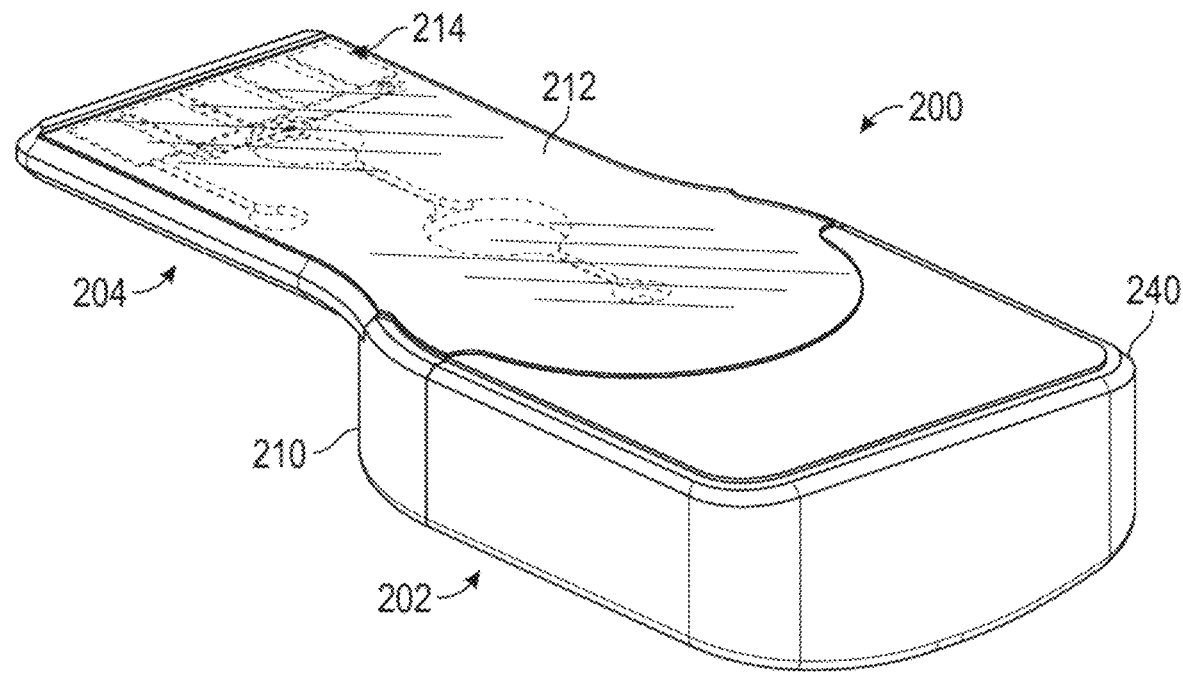
FIGS. 2A-2F depict an example cartridge for detection of a target that can be used in the handheld system of FIGS. 1A-1C.
Figure 2B:
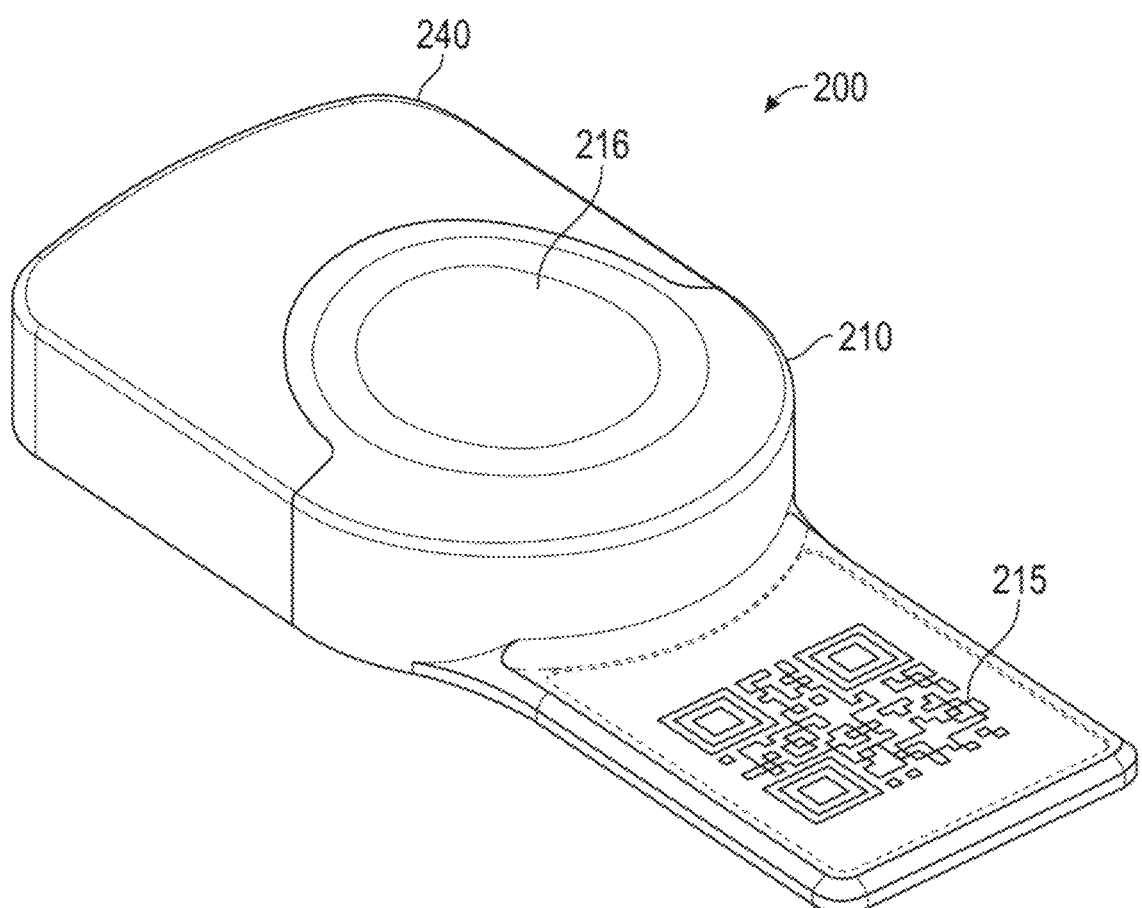

FIGS. 2A and 2B depict a complete cartridge 200 including the cartridge body 210 and the cap 240 coupled together. In use, the cap 240 and cartridge body 210 can operate to seal a provided sample within the cartridge 200, thereby preventing exposure of test operators to the sample and preventing any liquid from escaping into the electronics of an associated reader device. The cartridge body 210 and the cap 240 may be coupled by a friction fit, a snap fit, and/or one or more mechanical or chemical securing means. Coupling of the cartridge body 210 and the cap 240 is discussed in greater detail with reference to FIGS. 3A-3E.

The cartridge body 210 and the cap 240 can be formed from suitable fluid-impermeable materials such as plastic, metals, or the like, and may be opaque, translucent, or transparent. The cartridge body 210 can also include a translucent or transparent cover 212 partially defining a fluid path within the cartridge body 210, and one or more electrode interfaces 214. The cover 212, fluid paths, and electrode interfaces 214 are discussed in greater detail with reference to FIGS. 2C and 2D. The cartridge body 210 and/or the cap 240 can further include a cartridge identifier 215. The cartridge identifier 215 may include human-readable and/or machine-readable information, such as text, a barcode, a QR code, or the like. The cartridge identifier 215 can include any suitable information associated with the cartridge, such as information specifying a type of test, a target agent, a sample type, a cartridge serial number or other individual cartridge identifier, etc. In addition to serving as an identifier for a user of the type of test associated with the cartridge 200, the cartridge identifier 215 may also be scanned by a user (e.g., using a user interface device in communication with a reader device) to communicate one or more test protocols to the reader device. The cartridge body 210 and/or the cap 240 can include ergonomic features such as an indentation 216 to facilitate handling of the cartridge 200.

Figure 2C:
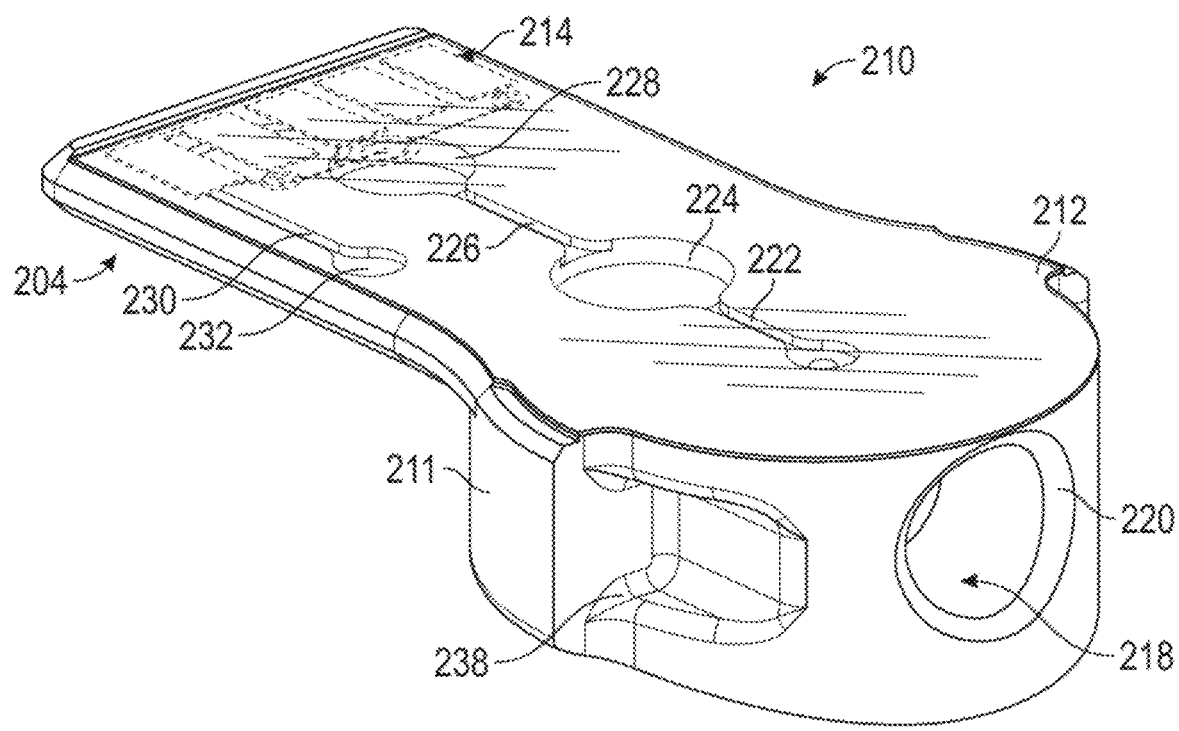
Figure 2D:
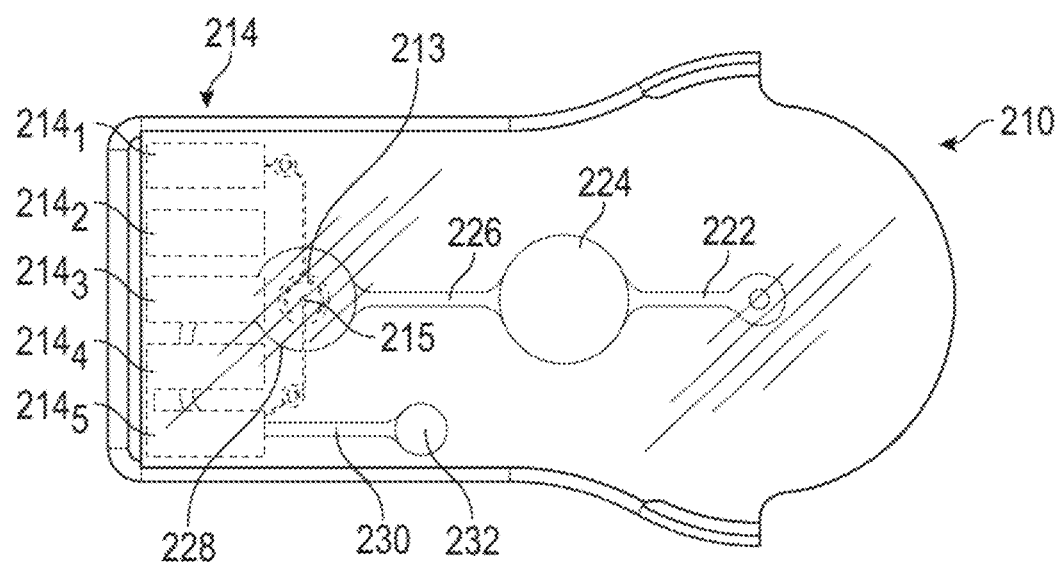

FIGS. 2C and 2D depict the cartridge body 210 component of the cartridge 200 of FIGS. 2A and 2B. The cartridge body 210 includes a base 211 and a cover 212. The base 211 can be formed from a fluid-impermeable material, for example injection molded or milled acrylic or plastic. The base 211 includes a receiving well 218 and components of a cartridge body flow path, including a first segment 222, a mixing well 224, a second segment 226, a test well 228, a third segment 230, and a vent 232. It will be appreciated that the particular geometric configurations or relative arrangements of these features may be varied in other embodiments. As used herein, fluidic communication refers to the capability to transfer fluids (e.g., liquid or gas). The cover 212 can be formed from a fluid-impermeable material. In some embodiments, the cover 212 is a translucent or transparent material, such as glass, plastic, or the like. The cover 212 is sealed to the base 211 to form the cartridge body 210 and to serve as a boundary confining fluids within the cartridge body flow path components described above. In some embodiments, a translucent or transparent cover 212 advantageously allows for visual inspection of a fluid within the cartridge body flow path (e.g., to verify that the test well is full prior to testing, etc.). One or more conductive components of an electrode interface 214 are disposed on the cover 212. Mating features 238 are sized and shaped to receive corresponding mating features of the cap 240. The receiving well 218 optionally includes a chamfer 220 to facilitate coupling of the cap 240 to the cartridge body 210.

The cartridge body flow path includes segments 222, 226, and 230, as well as an inlet (FIG. 3C) fluidically coupling the receiving well 218 to the first segment 222, the mixing well 224, and the test well 228. The first segment 222 of the cartridge body flow path leads from the inlet to the mixing well 224. The second segment 226 of the cartridge body flow path leads from the mixing well 224 to the test well 228. The third segment 230 is a test well outlet path leading from the test well 228 to a vent 232 that allows gas to escape from the test well 228 and out of the cartridge 200.

The mixing well 224 may include one or more reagents in a dry form (e.g., a powder). Powdered reagents and/or other dry reagents may be hydrated by a fluid sample when the fluid sample enters the mixing well 224. The reagents provided in the mixing well 224 can be selected based on one or more protocols of the intended test associated with the cartridge 200. Even or homogenous mixing of the reagents with the fluid sample can yield more accurate test results in some embodiments. As such, the mixing well 224 is configured to promote even mixing of the reagent with the fluid sample, for example by including curved regions and/or a cross-sectional shape that promote turbulent flow rather than laminar flow of the liquids within the mixing well 224. Turbulent flow is a flow regime in fluid dynamics characterized by chaotic changes in pressure and flow velocity of a fluid. Turbulent flow is in contrast to laminar flow, which occurs when fluid flows in parallel layers, with no disruption between those layers.

The segments 222, 226, and 230 of the cartridge body flow path, the mixing well 224, and/or the test well 228 can be entirely encased within the material of the base 211, or can have three surfaces formed from the material of the base 211 with the cover 212 forming an upper surface that seals these channels.

The internal section 204 or test region of the cartridge body 210 includes the segments 226, 230 of the cartridge body flow path, the test well 228, the valve 232, electrodes 213, 215, and an electrode interface 214. The electrode interface 214 includes a plurality of contact pads $214_1$-$214_5$. Although five contact pads $214_1$-$214_5$ are depicted, the cartridge body 210 may equally include more or fewer than five contact pads. A first contact pad $214_1$ is electrically connected to a first electrode 213 of the test well 228, and a second contact pad 214₅ is electrically connected to a second electrode 215 of the test well 228. One of the contact pads 214₁, 214₅ is configured for coupling an excitation electrode of a test well with a voltage or current source of a reader device and the other of the contact pads 214₁, 214₅ is configured for electrically coupling a signal electrode of the test well with a signal reading conductor of the test device. Additional ones of the contact pads 214₁-214₅ may serve other purposes in conjunction with the reader device. For example, one or more of the contact pads 214₁-214₅ may couple to circuitry of the electrode interface of the reader device to indicate one or more test protocols to the reader. In another example, a power cartridge, as described above with reference to FIGS. 1A-1C, may include a similar set of contact pads 214₁-214₅ configured to connect to circuitry of the reader device's electrode interface to activate a power circuit of the reader device.

The mixing well 224 can be provided with solid dried or lyophilized constituents for the testing process, for example primers and proteins. The particular selection and chemistry of these dried or lyophilized constituents can be tailored to a particular target or targets for which the cartridge 200 is designed to test. These dried or lyophilized constituents can be hydrated with the liquid e.g., a buffer or liquid sample that flows into the test well (e.g., the fluid sample within the cartridge 200) and thus activated for the test procedure. Beneficially, providing the dried or lyophilized solid constituents in the mixing well 224 enables the cartridge 200 to be stored before use containing the components needed for the amplification process, while also delaying initiation of amplification until after the sample has been applied.

The test well 224 is depicted as a generally cylindrical well formed as a circular opening in the material of the base 211 and bounded by the planar surface of the cover 212. The test well 224 contains two electrodes 213, 215, with one electrode being an excitation electrode configured to apply current to the sample in the test well 224 and the other electrode being a signal electrode configured to detect current flowing from the excitation electrode through the liquid sample. In some embodiments, one or more test wells can be provided with a thermistor in place of the electrodes in order to provide for monitoring of the temperature of the fluid within the cartridge 100.

In some embodiments, gas bubbles within the test well 224, particularly if positioned along the current path between the electrodes 213, 215, can create noise in the signal picked up by the signal electrode. This noise can reduce the accuracy of test results determined based on the signal from the signal electrode. A desired high-quality signal may be obtained when only liquid is present along the current path or when minimal gas bubbles are present along the current path. As described above, any air initially present in the fluid flowing along the cartridge body flow path can be pushed out through the vent 232. In addition, the electrodes 213, 215 and/or test well 224 can be shaped to mitigate or prevent nucleation of the liquid sample in which air or gas bubbles form in the fluid sample and collect along the electrodes 213, 215.

For example, the electrodes 213, 215 may be positioned at the bottom of the test well 224 in some embodiments. This can allow any air or gas to rise to the top of the fluid in the test well and away from the path between the electrodes. As used herein, the bottom of the test well 224 refers to the portion of the test well in which heavier liquid settles due to gravity, and the top of the test well refers to the portion of the test well in which lighter gas rises above the heavier liquids. Further, the electrodes 213, 215 are positioned away from the perimeter or edges of the test well 224 which is a location at which bubble nucleation typically occurs.

Further, the electrodes 213, 215 can be formed from a thin, flat layer of material that has minimal height relative to the underlying circuit board layer that forms the bottom of the test well 224. In some embodiments, the electrodes 213, 215 can be formed using electrodeposition and patterning to form a thin layer of metal film, for example around 300 nm in height. This minimal height can help prevent or mitigate air bubbles from becoming trapped along the interface between the electrode and the underlying layer. In some embodiments, a layer of conductive material can be deposited on top of each electrodes to create a smoother transition between the edge of the electrode and the bottom of the test well. For example, a thin polymid layer (e.g., around 5 microns in height) can be deposited on top of the electrode or the circuit board can be butter coated. Additionally or alternatively, the electrodes can be positioned in grooves in the underlying layer with the grooves having a depth approximately equal to the height of the electrode. These and other suitable methods can achieve an electrode that is approximately flat or flush with the bottom surface of the well.

Beneficially, the above-described features can help to keep the electrodes 213, 215 surrounded by liquid and prevent or reduce gas bubbles from becoming positioned along the current path between the electrodes 213, 215.

Figure 2E:
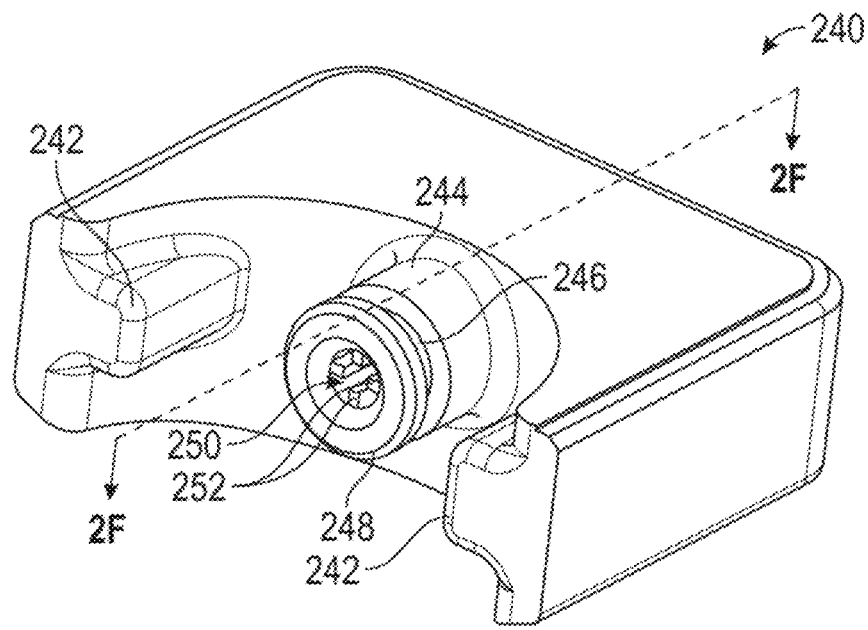
Figure 2F:
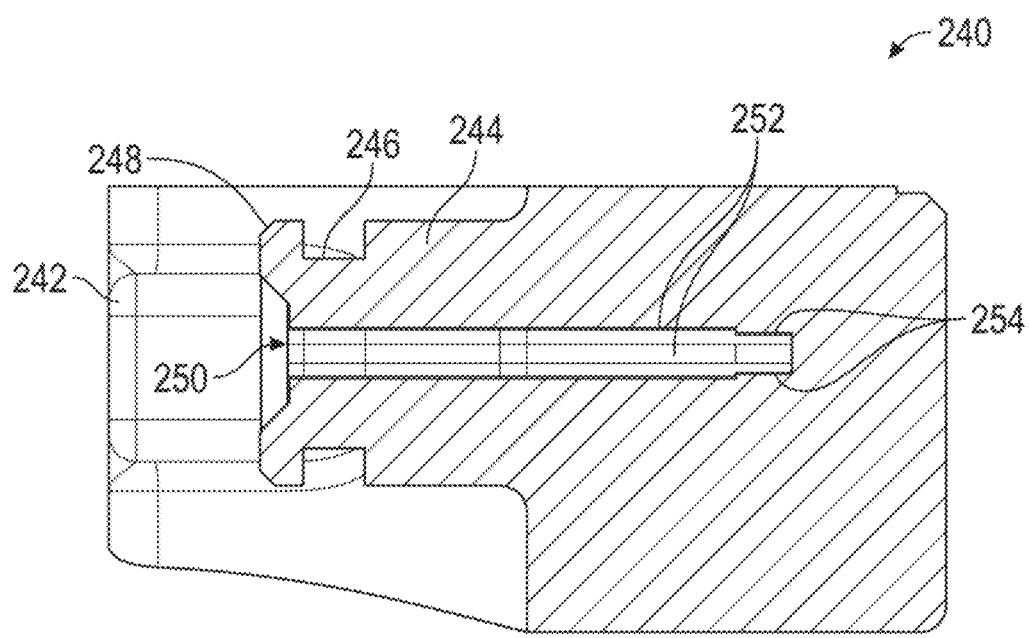

FIGS. 2E and 2F depict the cap 240 component of the cartridge 200. FIG. 2F is a cross-sectional view taken about the line 2F-2F in FIG. 2E to illustrate internal structures of the cap 240. The cap 240 is sized and shaped to mate with or otherwise mechanically couple to the cartridge body 210 to form a complete cartridge 200. The cap 240 includes mating features 242 configured to interlock with corresponding mating features 238 of the cartridge body when the cartridge 200 is assembled. The cap further includes a plunger 244 disposed about a retaining well 250 for retaining a capillary tube therein.

The plunger 244 is sized and shaped to sealingly engage with the receiving well 218 of the cartridge body 210 (FIGS. 2C-2D). The plunger 244 optionally includes a groove 246 configured to receive an O-ring or other gasket to eve and/or enhance the seal between the plunger 244 and the receiving well 218. An optional chamfer 248 at a distal end of the plunger 244 may facilitate the engagement of the plunger 244 with the receiving well 218, alone or in combination with the chamfer 200 of the receiving well 218 (FIGS. 2C-2D). As will be described in greater detail with reference to FIGS. 3A-3E, the plunger 244 thus sealingly engages with the receiving well 218 to propel a fluid sample into the cartridge body 210.

The retaining well 250 is configured to partially surround a capillary tube containing a fluid sample for testing. The retaining well 250 preferably has an interior diameter larger than the exterior diameter of the capillary tube to be inserted. A plurality of retaining structures 252 extend inward from the interior walls of the retaining well 250 to hold the capillary tube at a central location within the retaining well 250. Preferably, the distance between opposing retaining structures 252 is approximately equal to or slightly larger than the exterior diameter of the capillary tube. As shown in FIG. 2F, a rear portion 254 of each retaining structure 252 extends further inward relative to the remaining portion of the retaining structure 252. The distance between opposing rear portions 254 is small enough that the capillary tube cannot fit between the rear portions 254. Accordingly, the rear portions 254 of the retaining structures 252 block the movement of the capillary tube along the retaining well 250 and maintain a space between the capillary tube and the rear wall of the retaining well 250. As will be described in greater detail with reference to FIGS. 3A-3E, this spaced location of the capillary tube within the cap 240 allows air or other fluid to flow into the retaining well 250 around the sides of a capillary tube between the retaining structures and into the rear of the capillary tube.

The cartridge 200 of FIGS. 2A-2F provides a self-contained, easy to use device for performing an amplification-based test for a target, for example nucleic acid testing wherein genomic material in the sample is exponentially copied using a molecular amplification process. Beneficially, the user only needs to apply the sample and insert the cartridge 200 into a reader device in order to ascertain the result of the test in some embodiments, as the solid constituents of the amplification process are pre-provided within the cartridge and automatically mixed with the sample. In some embodiments, one or both of the cartridge or reader may include a heater and a controller configured to operate the heater to maintain the cartridge at the desired temperature for amplification. In some embodiments, one or both of the cartridge or reader may include a motor to impart vibrations to or otherwise agitate the cartridge to cause any trapped gas to rise to the top of the liquid and vent from the test wells.

FIGS. 3A-3E illustrate mechanical fluid transfer aspects of the cartridges 120, 200 described herein. As will be described in greater detail, the cartridge body 210 and cap 240 are configured to create air pressure when coupled together, such that the air pressure propels a fluid sample through the fluid path of the cartridge body 210. In some embodiments, the fluid sample may be driven through the fluid path of the cartridge body 210 by capillary action or wicking, instead of or in addition to fluid pressure. FIGS. 3A-3E illustrate the cap 240 with translucency to reveal interior features of the cap 240. The cartridge body 210 is illustrated in a cutaway view in FIGS. 3C-3E to reveal interior features of the cartridge body 210.

Figure 3A:
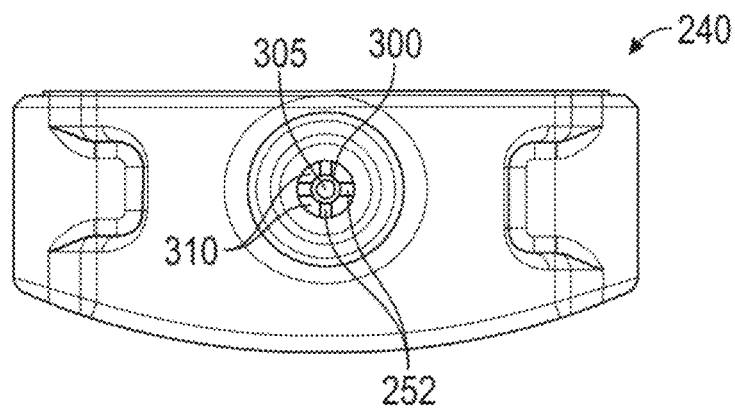
FIGS. 3A-3E depict a mechanical fluid transfer mechanism of the example cartridge of FIGS. 2A-2F.
Figure 3B:
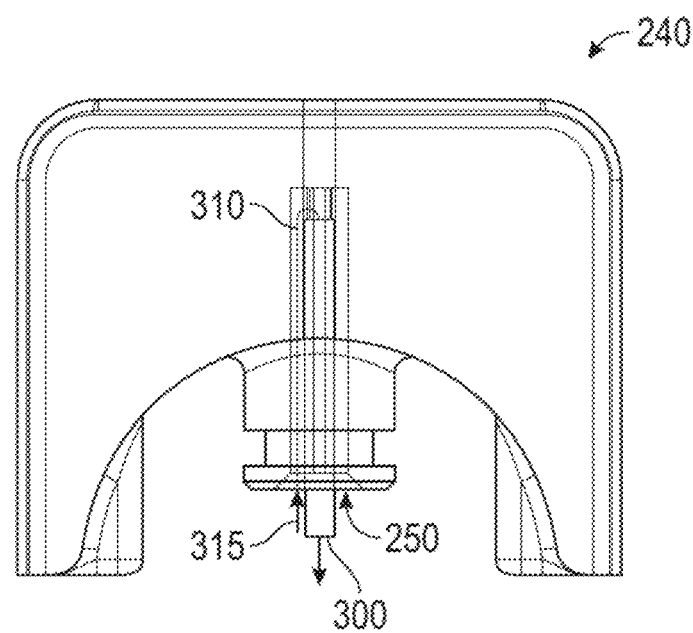

With reference to FIGS. 3A and 3B, a fluid sample may be received in a capillary tube 300, for example, within an inner lumen 305 of the capillary tube 300. The cap 240 is sized and shaped to receive the capillary tube 300 as described above with reference to FIGS. 2E and 2F. The fluid sample may be introduced into the capillary tube 300 while the capillary tube 300 is within the cap 240, or the capillary tube 300 may contain the fluid sample when it is placed into the cap 240.

FIG. 3A is a front view of the cap 240 of the cartridge 200. While the capillary tube 300 is disposed within the retaining well 250 of the cap 240, the retaining structures 252 hold the capillary tube 300 in a position spaced from the walls of the retaining well 250. Thus, a plurality of air channels 310 are formed between the interior of the retaining well 250 and the exterior of the capillary tube 300.

FIG. 3B is a top view of the cap 240 of FIG. 3A. A rear portion 310 of some or all of the retaining structures 310 (e.g., the rear portions 254 of FIG. 2F) cause the capillary tube 300 to remain spaced from the rear of the retaining well 250. This arrangement forms a cap fluid path 315 such that air or other fluids can flow into the retaining well 250 through the air channels 310, around the rear of the capillary tube 300, and out of the retaining well 250 through the inner lumen 305 of the capillary tube 300. Accordingly, application of a relatively high pressure at the air channels 310 can cause a fluid within the inner lumen 305 to flow out of the capillary tube 300 along the cap fluid path 315.

Figure 3C:
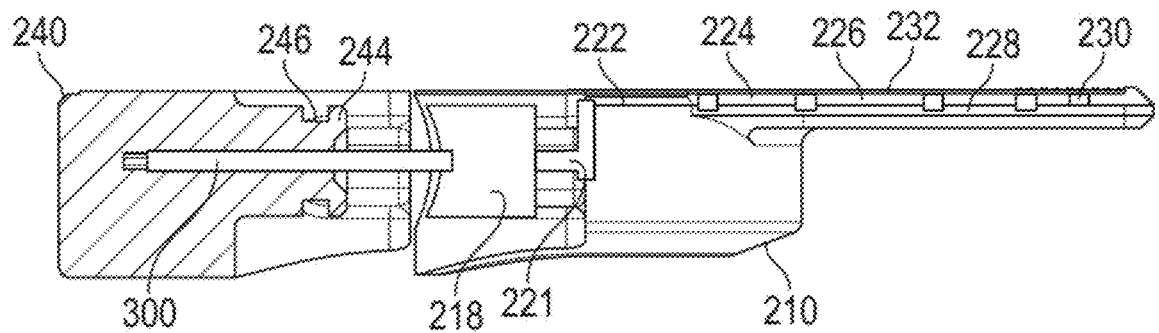
Figure 3D:
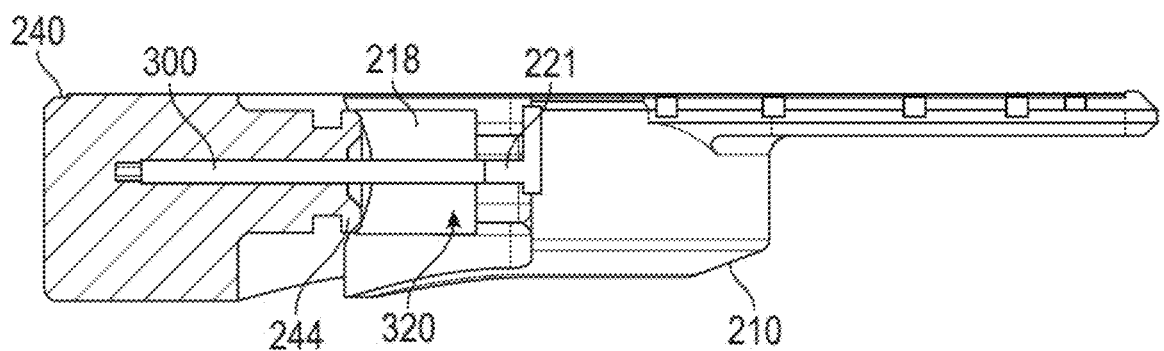
Figure 3E:
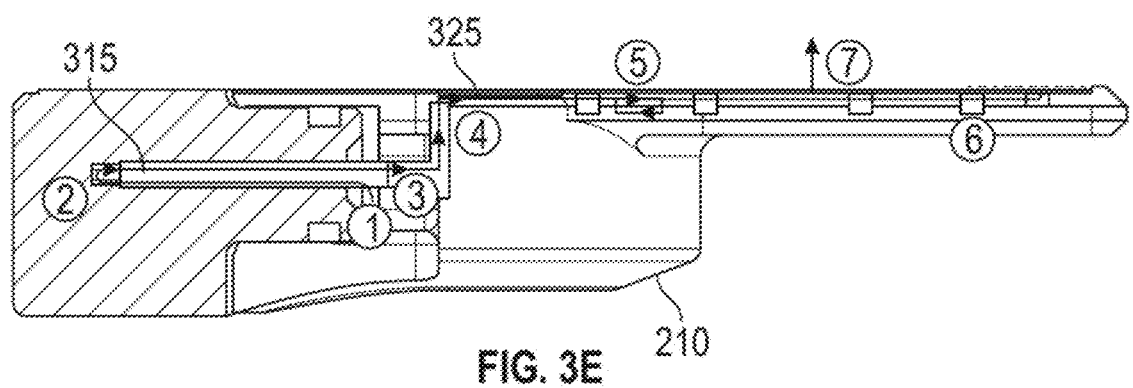

FIGS. 3C-3E illustrate various stages in a process of coupling the cap 240 to the cartridge body 210, together with associated fluid paths for effecting sample movement into the test well 228 and other components of a cartridge body flow path 325. FIG. 3C depicts the cap 240 adjacent but not coupled to the cartridge body 210, FIG. 3D depicts the cap 240 being coupled to the cartridge body 210, and FIG. 3E depicts the cap 240 fully coupled with the cartridge body 210.

As shown in FIG. 3C, the plunger 244, retaining well 250, and capillary tube 300 are aligned with the receiving well 218 of the cartridge body 210. The plunger 244 is sized and shaped to sealingly engage the receiving well 218. An O-ring or other seal (not shown) can be positioned in the groove 246 of the plunger 244 to achieve and/or enhance the seal between the plunger 244 and the receiving well 218. The receiving well 218 is fluidically coupled to the mixing well 224 by an inlet 221 sized and shaped to sealingly receive an end of the capillary tube 300. When the cap 240 is aligned with the cartridge body 210, the process continues to the configuration of FIG. 3D.

As shown in FIG. 3D, the plunger 244 engages the walls of the receiving well 218. As the plunger 244 (and/or an O-ring disposed on the plunger 244) engages the walls of the receiving well 218, a volume of ambient air is trapped within the receiving well 218. This trapped air 320 has a volume defined by the portion of the receiving well 218 not occupied by the plunger 244. As the cap 240 is pressed further onto the cartridge body 210, an outer end of the capillary tube 300 enters and sealingly engages with the inlet 221. Thus, as cap 240 and the cartridge body 210 are pressed further together, the trapped air 320 is compressed within the shrinking volume of the portion of the receiving well 218 not occupied by the plunger 214. Because the inlet 221 is blocked by the capillary tube 300, the compression of the trapped air 320 causes the trapped air 320 to flow along the cap flow path 315 of FIG. 3B.

Referring now to FIG. 3E, the fluid transfer effected by coupling the cap 240 and the cartridge body 210 will be described. FIG. 3E illustrates the flow along the cap flow path 315 and the cartridge body flow path 325 with encircled numbers shown as labels for certain points along the fluid path. The encircled numbers are discussed below as example steps of a progression of trapped air 320 and a fluid sample as they travel through the cap flow path 315 and the cartridge body flow path 325 within the cartridge 200, with each step including a directional arrow showing the direction of fluid travel at that step. For clarity and simplicity of FIG. 3E, some components labeled with reference numbers in FIGS. 2A-3D are not labeled in FIG. 3E.

Prior to step (1), a user provides a fluid sample within a capillary tube 300. Also prior to step (1), the capillary tube 300 is placed within the retaining well 250 of the cap 240 between the retaining structures 252 to form the cap flow path 315.

At step (1), as the plunger 244 compresses the trapped air 320, the trapped air 320 is forced into the air channels 310. The trapped air 320 flows along the cap flow path 315 through the air channels 310 between the retaining structures 252 and along the exterior of the capillary tube 300.

At step (2), the trapped air 320 reaches the rear of the retaining well 218. The trapped air 320 continues along the cap flow path 315 into the inner lumen 305 of the capillary tube 300. Upon entering the inner lumen 305, the trapped air 320 contacts and exerts a pressure upon the fluid sample contained within the capillary tube 300. The pressure is directed along the length of the capillary tube 300 toward the cartridge body 210.

At step (3), the fluid sample flows out of the capillary tube 300 and into the inlet 221 of the cartridge body 210. The fluid sample is propelled into the inlet 221 by the pressured exerted at the opposite end of the capillary tube 300 by the trapped air 320. Capillary action or wicking may also propel the fluid sample into the inlet 221, for example, where the inlet and fluidically connected segments along the cartridge body flow path 325 are suitably narrow to cause wicking. At step (4), the fluid sample travels through the first segment 222 of the cartridge body flow path 325.

At step (5), the fluid sample enters the mixing well 224. The mixing well may include one or more reagents. Agitation caused by the flow of the fluid sample within the relatively larger space of the mixing well 224 causes the reagent and the sample to be mixed. In some embodiments, the reagent and the fluid sample are mixed into a homogeneous solution in which the reagent is evenly distributed throughout the fluid sample. The depth, width, and/or cross-sectional profile of the mixing well 224 may be selected to facilitate mixing of the reagent and the fluid sample.

At step (6), the mixed reagent and fluid sample (referred to as the "test fluid") leave the mixing well 224 and travel along the second segment 226 of the cartridge body flow path 325 into the test well 228.

At step (7), a portion of the test fluid continues along the third segment 230 of the cartridge body flow path 325 to fill any remaining open volume within the cartridge body flow path 325. The path of step (7) shows the optional flow of a gas (e.g., a gas portion of the test fluid or ambient air present within the cartridge body 210) through the valve 232. In some embodiments, the valve 232 can include a liquid-impermeable, gas-permeable filter to allow any gas present in the test fluid or within the cartridge body 210 to vent through the valve 232 as the test fluid fills the space within the cartridge body flow path 325. The valve 232 may further minimize the occurrence of air bubbles within the test well 228. In some embodiments the valve 232 may not present and/or may not be configured to vent gas.

Following the completion of steps (1)-(7), the cartridge 200 is sealed and contains the test fluid within the cartridge body 210 and the cap 240. The sealed cartridge 200 may then be placed into a reader device such as the reader devices 110, 600 described herein, for testing to detect one or more target agents within the test fluid. In various embodiments, the size of the fluid sample and/or the quantity of the reagent may preferably be selected to provide sufficient test fluid to substantially fill the fluid space enclosed within the cartridge 200 along the cap flow path 315 and the cartridge body flow path 325. The volume of the receiving well 218, and the corresponding size of the plunger 244, may preferably be selected so that the receiving well 218 contains sufficient air for transporting the fluid sample along the length of the fluid path and into the test well 328. It will be understood that the propulsion of the fluid sample through the capillary tube 300 into and along the cartridge body flow path 325, as described above with reference to FIGS. 3A-3E, may occur due to capillary action or wicking, fluid pressure due to the compression of a trapped liquid or gas (e.g., air) within the receiving well 218, or both.

Figure 4A:
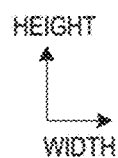
FIGS. 4A-4G depict various examples of electrodes that can be used in a test well of the cartridges of FIGS. 1A-2F or in the test well or channel of another suitable target detection cartridge as described herein.
Figure 4A:
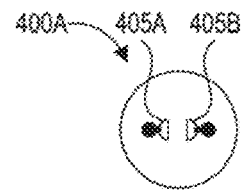
Figure 4B:
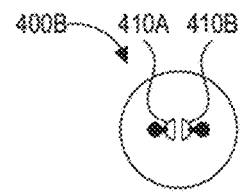
Figure 4C:
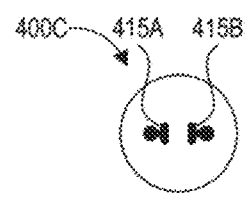
Figure 4D:
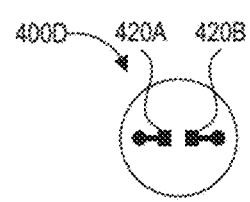
Figure 4E:
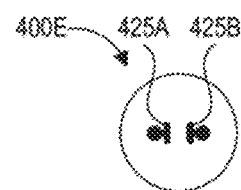
Figure 4F:
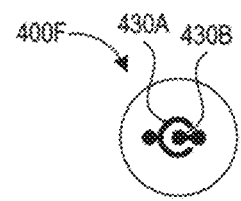
Figure 4G:
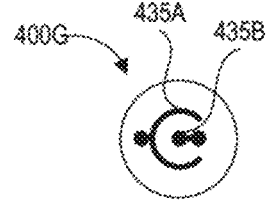
Figure 4H:
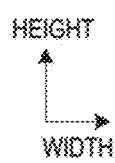
FIGS. 4H-4N depict further examples of electrodes that can be used to implement three-terminal sensing and/or four-terminal sensing in a test well of the cartridges of FIGS. 1A-2F or in the test well or channel of another suitable target detection cartridge as described herein.
Figure 4H:
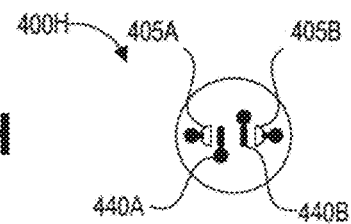
Figure 4I:
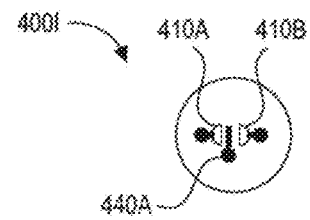
Figure 4J:
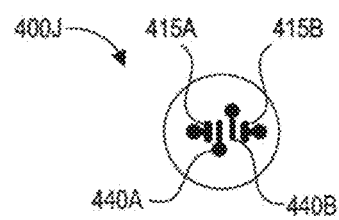
Figure 4K:
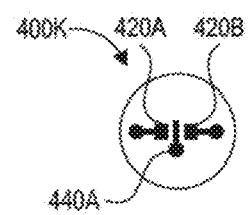
Figure 4L:
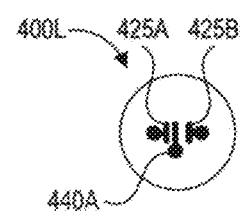
Figure 4M:
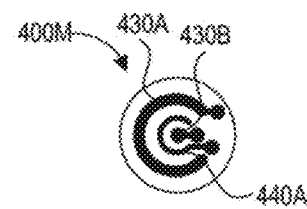
Figure 4N:
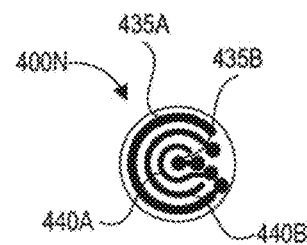

FIGS. 4A-4N depict various examples of electrode configurations that can be used in a test well of the cartridges of FIGS. 2A-3E or in the test well or channel of another suitable target detection cartridge as described herein. The test wells shown in FIGS. 4A-4N are depicted as circular, however the electrodes can be used in test wells of other geometries in other examples. Unless otherwise noted, the solid circles in FIGS. 4A-4N represent contacts between the disclosed electrodes and conductors leading to or from the electrode. "Width" as used below refers to a dimension along the horizontal direction of the pages of FIGS. 4A-4N, and "height" as used below refers to a dimension along the vertical direction of the pages of FIGS. 4A-4N. Though depicted in a particular orientation, the illustrated electrodes of FIGS. 4A-4N can be rotated in other implementations. Further, the disclosed example dimensions represent certain potential implementations of the electrode configurations 400A-400G, and variations can have different dimensions that follow the same ratios between the provided example dimensions. The electrodes shown in FIGS. 4A-4N can be made from suitable materials including platinum, gold, steel, or tin. In experimental testing, tin and platinum performed similarly and suitably for certain test setups and test targets.

FIG. 4A depicts a first electrode configuration 400A wherein the first and second electrodes 405A, 405B are each formed as a semicircular perimeter. The straight edge of the first electrode 405A is positioned adjacent to the straight edge of the second electrode 405B and separated by a gap along the width of the configuration 400A. The gap is larger than the radius of the semicircle of the electrodes. Thus, the first and second electrodes 405A, 405B are positioned as mirrored semicircular perimeters. In one example of the first electrode configuration 400A, the gap between the closest portions of the first and second electrodes 405A, 405B spans approximately 26.369 mm, the height (along the straight edge) of each of the electrodes 405A, 405B is approximately 25.399 mm, and the radius of the semicircle of each of the electrodes 405A, 405B is approximately 12.703 mm.

FIG. 4B depicts a second electrode configuration 400B. Similar to the first electrode configuration 400A, the first and second electrodes 410A, 410B of the second electrode configuration 400B are each formed as a semicircular perimeter and are positioned as mirrored semicircles with their straight edges facing one another. The first and second electrodes 410A, 410B of the second electrode configuration 400B can be the same size as the first and second electrodes 405A, 405B of the first configuration 400A. In the second electrode configuration 400B, the gap along the width of the configuration 400B between the first and second electrodes 410A, 410B is smaller than in the first configuration 400A, and the gap is smaller than the radius of the semicircle of the electrodes 410A, 410B. In one example of the second electrode configuration 400B, the gap between the closest portions of the first and second electrodes 410A, 410B spans approximately 10.158 mm, the height (along the straight edge) of each of the electrodes 410A, 410B is approximately 25.399 mm, and the radius of the semicircle of each of the electrodes 410A, 410B is approximately 12.703 mm.

FIG. 4C depicts a third electrode configuration 400C having first and second linear electrodes 415A, 415B separated by a gap along the width of the configuration 400C, where the gap is approximately equal to the height of the electrodes 415A, 415B. The width of the electrodes 415A, 415B is approximately one half to one third of the height of the electrodes. In one example of the third electrode configuration 400C, the gap between the closest portions of the first and second electrodes 415A, 415B spans approximately 25.399 mm, the height of each of the electrodes 415A, 415B is also approximately 25.399 mm, and the width of each of the electrodes 415A, 415B is approximately 10.158 mm.

The ends of the first and second electrodes 415A, 415B can be radiused, for example having a radius of around 5.078 mm.

FIG. 4D depicts a fourth electrode configuration 400D having first and second rectangular electrodes 420A, 420B separated by a gap along the width of the configuration 400D, where the gap is approximately equal to the width of the electrodes 420A, 420B. In one example of the fourth electrode configuration 400D, the gap between the closest portions of the first and second electrodes 420A, 420B spans approximately 20.325 mm, the height of each of the electrodes 420A, 420B is also approximately 23.496 mm, and the width of each of the electrodes 420A, 420B is approximately 17.777 mm.

FIG. 4E depicts a fifth electrode configuration 400E having first and second linear electrodes 425A, 425B separated by a gap along the width of the configuration 400E, where the gap is approximately equal to the height of the electrodes 425A, 425B. The fifth electrode configuration 400E is similar to the third electrode configuration 400C, with the width of the electrodes 425A, 425B reduced to around one half to two thirds of the width of the electrodes 415A, 415B while having the same height. In one example of the fifth electrode configuration 400E, the gap between the closest portions of the first and second electrodes 425A, 425B spans approximately 25.399 mm, the height of each of the electrodes 425A, 425B is also approximately 25.399 mm, and the width of each of the electrodes 425A, 425B is approximately 5.078 mm. The ends of the first and second electrodes 425A, 425B can be radiused, for example having a radius of around 2.542 mm.

FIG. 4F depicts a sixth electrode configuration 400F having concentric annular electrodes 430A, 430B. The sixth electrode configuration 400F is the configuration shown in the test well 228 of FIGS. 2A, 2C, and 2D. The inner electrode 430B can be a disc or circular-shaped electrode and can be positioned in the center of the test well. The outer electrode 430A can be a semicircular electrode formed concentrically around the inner electrode 430B and separated from the inner electrode 430B by a gap. In the sixth electrode configuration 400F, the gap is approximately equal to the radius of the inner electrode 430B. A break in the semicircle of the outer electrode 430A occurs where a conductive lead connects the inner electrode 430B to the current providing conductor. In one example of the sixth electrode configuration 400F, the gap between the inner edge of the annular first electrode 430A and the outer perimeter of the circular second electrode 430B spans approximately 11.430 mm, the radius of the circular second electrode 430B is approximately 17.777 mm, and the thickness of the annulus of the annular first electrode 430A is approximately 5.080 mm. The ends of the first electrode 430A can be radiused, for example having a radius of around 2.555 mm, and the gap between the open ends of the annulus of the first electrode 435A can be around 28.886 mm from vertex to vertex.

FIG. 4G depicts a seventh electrode configuration 400G having concentric annular electrodes 435A, 435B. Similar to the embodiment of FIG. 4F, the inner electrode 435B can be a disc or circular-shaped electrode having the same radius as inner electrode 430B and can be positioned in the center of the test well. The outer electrode 435A can be a semicircular electrode formed concentrically around the inner electrode 435A and separated from the inner electrode 435A by a gap. In the seventh electrode configuration 400G, the gap is greater than the radius of the inner electrode 435B, for example two to three times greater. Correspondingly, the outer electrode 435B has a larger radius than the outer electrode 430B. In one example of the seventh electrode configuration 400G, the gap between the inner edge of the annular first electrode 435A and the outer perimeter of the circular second electrode 435B spans approximately 24.131 mm, the radius of the circular second electrode 435B is approximately 17.777 mm, and the thickness of the annulus of the annular first electrode 435A is approximately 5.080 mm. The ends of the first electrode 435A can be radiused, for example having a radius of around 2.555 mm, and the gap between the open ends of the annulus of the first electrode 435A can be around 46.846 mm from vertex to vertex.

In the embodiments of FIGS. 4A-4E, either electrode can be used as the excitation electrode and the other electrode can be used as the signal electrode. In the embodiments of FIGS. 4F and 4G, the inner electrode 430B, 435B is configured to be used as the excitation electrode (e.g., coupled to a current source) and the outer electrode 430A, 435A is configured to be used as the signal electrode (e.g., provides its signal to a memory or processor). In some example tests, the sixth electrode configuration 400F exhibited the best performance of the configurations shown in FIGS. 4A-4G.

FIGS. 4H-4N depict further examples of electrode configurations suitable for implementing three-terminal sensing and/or four-terminal sensing. In some embodiments, three-terminal sensing (e.g., potentiostat-type or 3-wire measurement) or four-terminal sensing (e.g., Kelvin-type or 4-wire measurement) may improve the accuracy of impedance measurements in the systems and methods described herein. For example, the excitation electrode and the signal electrode may themselves carry some charge. Additionally, there may be some additional impedance related to surface effects at the electrode-fluid interface. Accordingly, a third electrode or a third and fourth electrode (e.g., a second electrode pair) may further be disposed within the test well. The third and/or fourth electrodes can carry a substantially smaller or negligible current relative to the current carried by the excitation and signal electrodes. The third and/or fourth electrodes may thus be used to accurately determine a voltage (e.g., a voltage between the third and fourth electrodes, or a voltage between the third electrode and the excitation or signal electrode). This precisely measured voltage may be used to determine an impedance measurement having enhanced accuracy. It will be understood that the configurations of three or four electrodes illustrated in FIGS. 4H-4N are merely examples of a number of three- or four-terminal configurations that may be provided within the test wells of the present disclosure.

FIG. 4H depicts an electrode configuration similar to the electrode configuration of FIG. 4A, with the addition of a third electrode 440A and a fourth electrode 440B disposed between the first electrode 405A and the second electrode 405B. Either or both of the third electrode 440A and the fourth electrode 440B may be used to implement three- or four-terminal sensing.

FIG. 4I depicts an electrode configuration similar to the electrode configuration of FIG. 4B, with the addition of a third electrode 440A disposed between the first electrode 410A and the second electrode 410B. The third electrode 440A may be used to implement three-terminal sensing.

FIG. 4J depicts an electrode configuration similar to the electrode configuration of FIG. 4C, with the addition of a third electrode 440A and a fourth electrode 440B disposed between the first electrode 415A and the second electrode 415B. Either or both of the third electrode 440A and the fourth electrode 440B may be used to implement three- or four-terminal sensing.

FIG. 4K depicts an electrode configuration similar to the electrode configuration of FIG. 4D, with the addition of a third electrode 440A disposed between the first electrode 420A and the second electrode 420B. The third electrode 440A may be used to implement three-terminal sensing.

FIG. 4L depicts an electrode configuration similar to the electrode configuration of FIG. 4E, with the addition of a third electrode 440A disposed between the first electrode 425A and the second electrode 425B. The third electrode 440A may be used to implement three-terminal sensing.

FIG. 4M depicts an electrode configuration similar to the electrode configuration of FIG. 4F, with the addition of a third electrode 440A disposed between the outer electrode 430A and the inner electrode 430B. The third electrode 440A may be used to implement three-terminal sensing.

FIG. 4N depicts an electrode configuration similar to the electrode configuration of FIG. 4G, with the addition of a third electrode 440A and a fourth electrode 440B disposed between the outer electrode 435A and the inner electrode 435B. Either or both of the third electrode 440A and the fourth electrode 440B may be used to implement three- or four-terminal sensing.

Figure 5A:
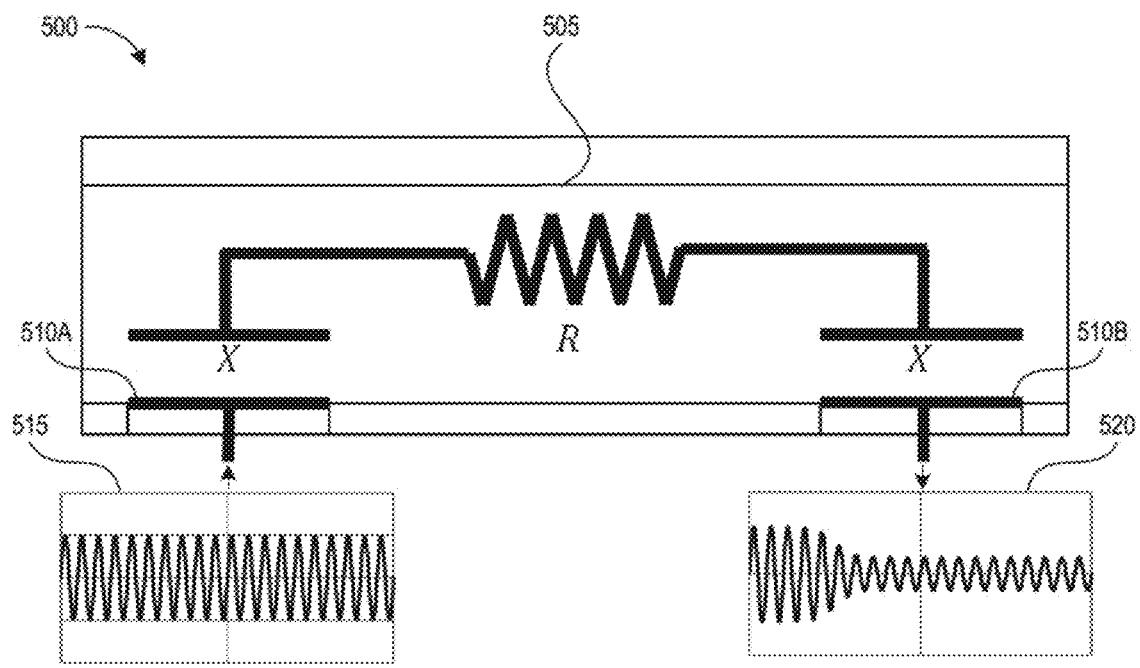
FIG. 5A depicts a first electrode or excitation electrode and a second electrode or signal electrode that may be spaced apart from one another within a test well of the cartridges of FIGS. 1A-2F or in the test well or channel of another suitable target detection cartridge as described herein.

FIG. 5A schematically depicts a first electrode or excitation electrode and a second electrode or signal electrode that may be spaced apart from one another within a test well of the cartridges of FIGS. 2A-3E or in the test well or channel of another suitable target detection cartridge as described herein.

The formation of an aggregate, nucleic acid complex, or polymer, for example during an amplification process in the test wells of cartridges of FIGS. 2A-3E, can affect waveform characteristics of one or more electrical signals that are sent through a channel. As shown in FIG. 5A, a first electrode or excitation electrode 510A is spaced apart from a second electrode or sensing electrode 510B within test well 505. The test well 505 can contain a test solution undergoing an amplification process. During some of all of that process, an excitation voltage 515 can be provided to the excitation electrode 510A, from which the excitation voltage 515 is transmitted into the fluid (preferably all or substantially all liquid) within the well 505.

After passage through and attenuation by the liquid sample (represented schematically by the resistance R and reactance X), the attenuated excitation voltage is sensed or detected at the sensing electrode 510B. The fluid acts as a resistor R in series with the excitation electrode 510A and the sensing electrode 510B. The fluid also acts as in series capacitor(s), shown by the reactance X. The raw sensed signal during some or all of the duration of a test can be represented over time as a sinusoidal curve with varying amplitudes, similar to that shown in plot 520.

The excitation voltage 515 can be an alternating current at a predetermined drive frequency. The particular frequency selected can depend for example upon the particular target sought to be detected, the medium of the test sample, the chemical makeup of the amplification process constituents, the temperature of the amplification process, and/or the excitation voltage. In some embodiments of the cartridges of FIGS. 2A-3E, the excitation drive frequency can be between 1 kHz and 10 kHz at as low an excitation voltage as possible. As one example, in tests performed to identify a target of H. Influenza ($10^6$ copies/reaction) spiked into 5% whole blood, excitation sensor drive frequency was varied from 100 Hz to 100,000 Hz at 0.15 Volts. These tests revealed that the desired "signal cliff," an artifact in a portion of the signal indicative of a positive test sample described in more detail below, becomes more easily detectable below 100 Hz and is most easily detectable between 1 kHz and 10 kHz. Further, with frequencies in the range between 1 kHz and 10 kHz, the signal cliff advantageously could be identified before 12 minutes of test time had elapsed. Beneficially, faster identification of the signal cliff can result in shorter test times, in turn resulting in quicker provision of test results and the ability to perform more tests per day. At frequencies lower than 1 kHz, the reactance component of the signal (in which the signal cliff may be found in a positive sample) decreased monotonically. The sensor drive frequency can be similarly fine-tuned for other tests to optimize performance, that is, to optimize the detectability of a signal cliff. Detectability of a signal cliff refers to the ability to consistently differentiate between a positive sample and a negative sample.

Figure 5B:
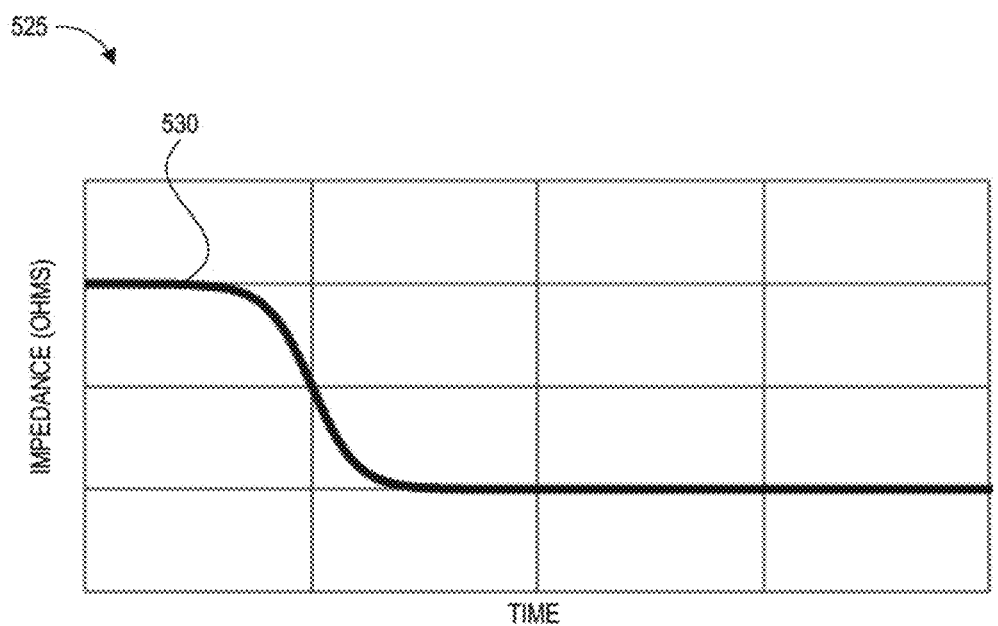
FIG. 5B depicts an example signal that can be extracted from the signal electrode of FIG. 5A.

FIG. 5B depicts an example plot 525 showing an impedance signal 530 that can be extracted from the raw signal 520 provided by the sensing electrode 510B. The impedance signal 530 represents the electrical impedance Z of the test well over time. The impedance Z can be represented by a Cartesian complex number equation as follows:

$$Z = R + jX$$

where R represents the resistance of the test well and is the real part of the above equation and the X represents the reactance of the test well and is the imaginary part of the above equation (denoted by j). Thus, the impedance of the test well can be parsed into two components, the resistance R and the reactance X.

Initially, the value of the resistance R can be determined by taking a baseline measurement of the test well prior to or at the outset of the amplification process. Although the resistance of the test fluid can drift away from this baseline value throughout the duration of the test, the current sensed by the sensing electrode 510B due to the resistance of the test fluid can be in phase with the signal provided through the excitation electrode 510A. Thus, changes or drift in the resistance can be identified by values of the in phase component of the signal 520 over time. The reactance can arise from the effect of inductance in the test fluid, capacitance in the test fluid, or both; this effect can cause the fluid to retain current (e.g., electrons provided by excitation electrode 510A) temporarily. After some time this retained current flows out of the test fluid into the sensing electrode 510B. Due to this delay, the current sensed by the sensing electrode 510B due to the reactance of the test fluid can be out of phase with the current sensed from the resistance of the test fluid. Thus, values of the reactance of the test fluid can be identified by values of the out of phase component of the signal 520 over time. The reactance can fluctuate throughout the duration of the test based on changes to the chemical constituents of the test fluid due to the amplification process. The signal cliff (e.g., a rise or drop in the reactance at or greater than a threshold rate or magnitude and/or during a predetermined window of time) indicative of a positive sample can be found in the reactance X.

During a test, the excitation electrode 510A can be sinusoidally excited with some amplitude and voltage. The excitation electrode 510A is in series with the test liquid in the well, which can be considered as a resistor R. The resistor (e.g., the test fluid) and electrode form a voltage divider, which has a voltage determined by the ratio of the resistor and electrode chemistry/impedances. The resulting voltage waveform sensed at the sensing electrode 510B represents the complex impedance signal 530. In some embodiments, a curve such as the impedance signal 530 may not be generated, but rather the raw sensed signal 520 can be parsed into its resistance and reactance components as described herein. The impedance signal 530 is provided as an example representation of a combined curve representing both the resistance of the test fluid and the reactance of the test fluid over time. The complex impedance signal 530 can be interpreted as a quadrature-modulated waveform (e.g., a combination of an in-phase waveform resulting from the resistance of the test fluid and an out-of-phase waveform resulting from the reactance of the test fluid), where the in-phase and out-of-phase components change on a timescale much greater than the modulation frequency. The in-phase waveform is in-phase with the composite waveform of the complex impedance. Some implementations can use a synchronous detector, for example having multipliers and low pass filters implemented in a field programmable gate array (FPGA), to extract the in-phase and out-of-phase components from the raw signal 520 and compute their amplitude and phase.

In order to parse the impedance signal 530 (or the raw sensed signal 520) into its constituent resistance and reactance components, the voltage waveform 520 at the sensing electrode 510B is sampled faster than its Nyquist frequency (e.g., two times the highest frequency of the excitation voltage) and then decomposed into an in-phase component (resistance) and an out-of-phase component (reactance). The in-phase and out-of-phase voltage components can be computed using the known series resistance (e.g., the value of R) to calculate the real component of the impedance (the resistance) and the imaginary component of the impedance (the reactance).

Figure 5C:
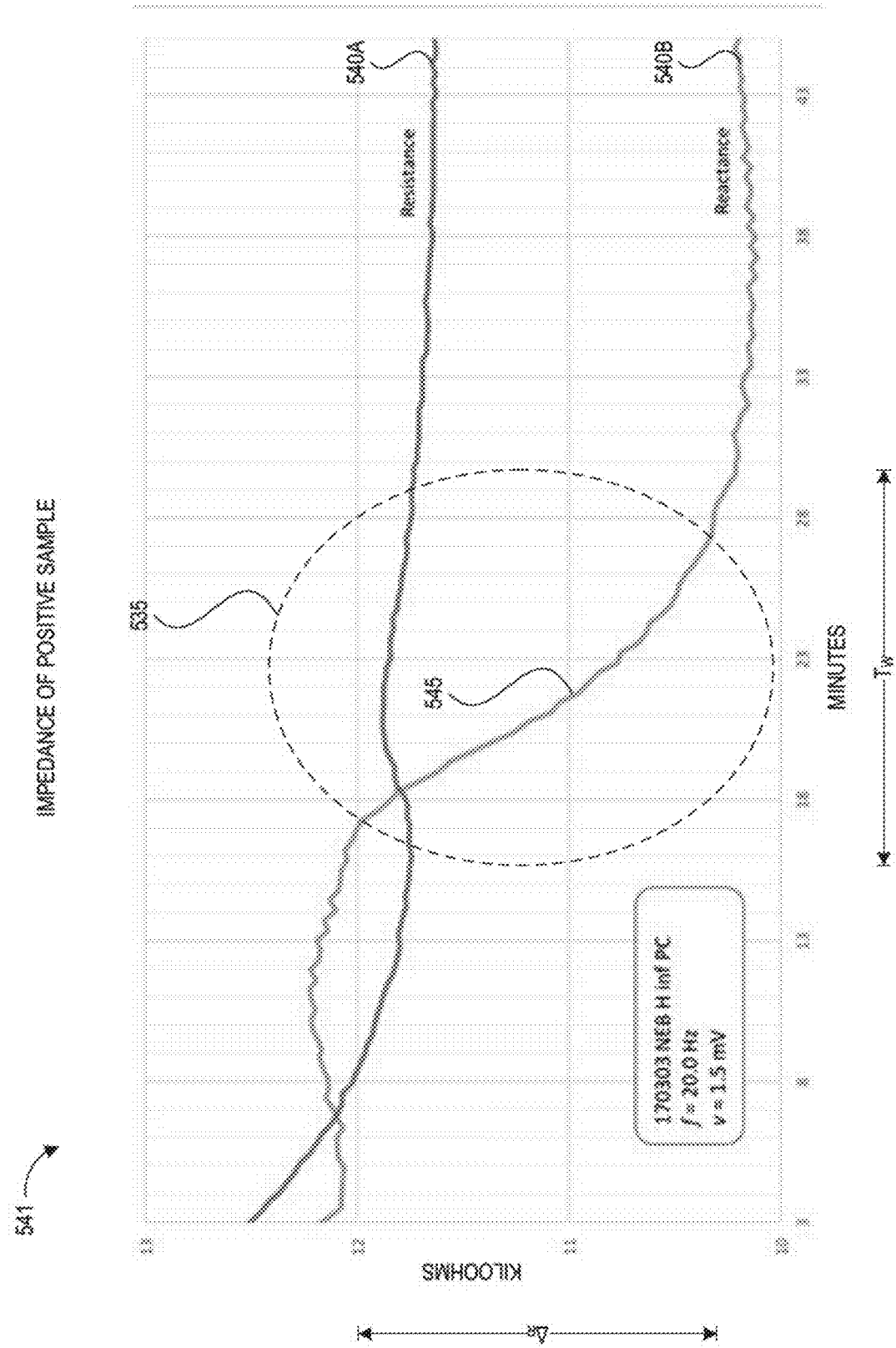
FIG. 5C depicts the resistance and reactance components extracted from a signal as shown in FIG. 5B generated based on an example positive test.

FIG. 5C depicts a plot 541 of the resistance 540A and reactance components 540B over time (t=3 minutes to t=45 minutes) extracted from a raw signal 520 generated based on an example positive test. As illustrated, the signal cliff 545 represents a change $\Delta_R$ in the reactance 540B during a particular window of time $T_W$. The signal cliff 545 indicates a positive sample. At times occurring prior to the signal cliff 545, the reactance curve 540B is relatively flat or stable, and again after the signal cliff 545 the reactance curve 540B is relatively flat or stable. Thus, in this embodiment the signal cliff 545 for the particular test parameters represented by the plot 541 occurs as a drop of $\Delta_R$ in the expected region 535.

The magnitude of the change $\Delta_R$ in the reactance that corresponds to a positive sample signal cliff 545, as well as the position and/or duration of the particular window of time Tw at which the signal cliff 545 is expected to occur, can vary depending on a number of parameters of the test. These parameters include the particular target of the test (e.g., the rate at which that target amplifies), the frequency of the excitation voltage, the configuration of the excitation and sensor electrodes (e.g., their individual shapes and dimensions, the gap separating the electrodes, and the material of the electrodes), the sampling rate, the quantity of amplification agents provided at the start of the test, the temperature of the amplification process, and the amount of target present in the sample. In some embodiments, the expected characteristics of a signal cliff of a positive sample, predetermined for example through experimentation, can be used for differentiating between positive samples and negative samples. In some embodiments, the expected characteristics of a signal cliff can be used for determining the severity or progress of a medical condition, for example via correlations between particular signal cliff characteristics and particular initial quantities of the target in the sample. The predetermined expected characteristics can be provided to, stored by, and then accessed during test result determination by a reader device configured to receive signals from the sensing electrode(s) of a test cartridge.

For a given test, the expected magnitude of the change $\Delta_R$ in the reactance and the expected window of time $T_W$ of a signal cliff 545 for a positive sample can be determined experimentally based on monitoring and analyzing the reactance curves generated by positive control samples (and optionally negative control samples). In some embodiments, the test parameters influencing the signal cliff can be varied and fine-tuned to identify the parameters that correspond to an accurately distinguishable signal cliff. A reader and cartridge as described herein can be configured to match the tested configuration and provided with expected signal cliff characteristics for that test.

For example, in a set of experimental tests for *H. influenza*, the test fluid initially included amplification primers and 1,000,000 added target copies, the excitation voltage was 200 mV P2P, the test parameters included a 10 kHz sweep start and a 10 MHz sweep stop for the frequency of the excitation current, and close and far electrode gaps were configured at 2.55 mm and 5 mm respectively. The amplification temperature was set to 65.5 degrees Celsius, and the two electrode setups (one for each of the close and far gaps) included platinum electrodes. At low frequencies (10 kHz-100 kHz), detectable signal cliffs were identified beginning around 23 minutes into amplification around 10 kHz and around 30 minutes around 100 kHz using the 5 mm gap electrode configuration, with the magnitude of change in reactance being around 3.5-4 Ohms at 10 kHz and dropping to around 3.25-3.5 Ohms at 100 kHz. At low frequencies (10 kHz-100 kHz), detectable signal cliffs were identified beginning around 25 minutes into amplification around 10 kHz and around 30 minutes around 100 kHz using the 2.5 mm gap electrode configuration, with the magnitude of change in reactance being around 3.5-4 Ohms. At higher frequencies, the drop in reactance of the signal cliff decreased, and the time at which these smaller signal cliffs were identified was shifted to later in the amplification process. Accordingly, in this example a test well in a test cartridge may be configured with the 5 mm gap electrodes and a reader device may be configured to provide 10 kHz excitation current to the test cartridge during amplification. The reader device can be provided with instructions to provide this current and monitor the resulting reactance of the test well throughout amplification or for a window of time around the expected signal cliff time (here, 23 minutes), for example between 20 and 35 minutes. The reader device can also be provided with instructions to identify a positive sample based on the reactance exhibiting around a 3.5-4 Ohm change around 23 minutes into amplification, or within the window of time around the expected signal cliff time.

Once identified, the values for $\Delta_R$ and $T_W$ can be provided to reader devices for use in distinguishing between positive and negative samples for that particular test. In some examples, such devices can determine whether the reactance curve 540B has the required value and/or slope at the identified window of time $T_W$ to correspond to the signal cliff. In other embodiments, the reader device can analyze the shape of the reactance curve over time to determine whether it contains a signal cliff. In some embodiments, a reader can modify its testing procedures based on the identified window of time $T_W$ at which the signal cliff 545 is expected to occur, for example by only providing the excitation voltage and monitoring the resultant signal within this window, advantageously conserving power and processing resources compared to continuous monitoring during an entire test time.

Figure 5D:
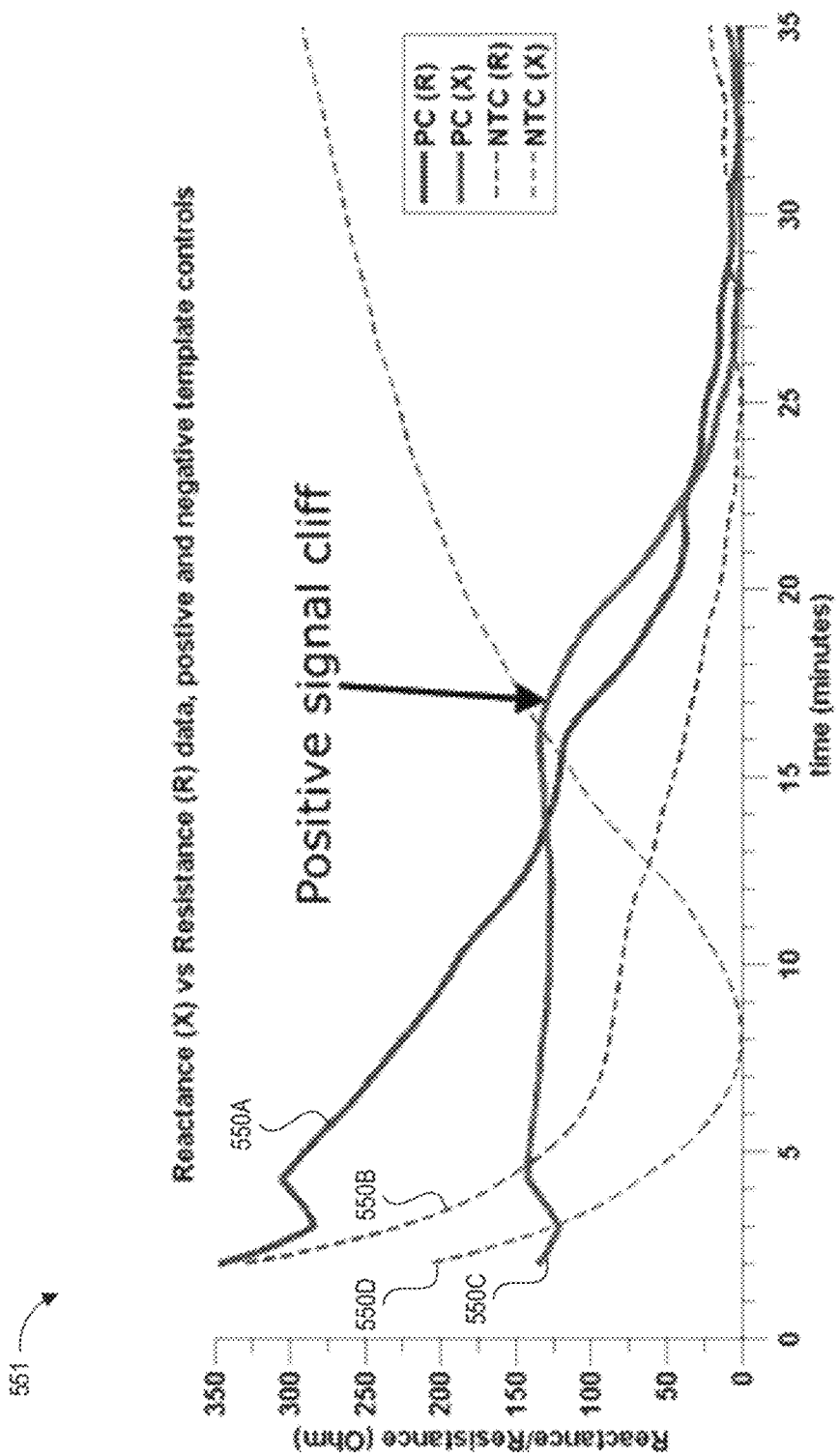
FIG. 5D depicts the resistance and reactance components extracted from signals as shown in FIG. 5B from example tests of positive and negative controls.

FIG. 5D depicts a plot 551 of the resistance and reactance components extracted from the raw sensor data of a sensing electrode 510B during example tests of positive and negative controls. Specifically, the plot 551 shows a curve 550A of the resistance of the positive sample, a curve 550B of the reactance of the positive sample, a curve 550C of the resistance of the positive sample, and a curve 550D of the reactance of the positive sample over the 35 minute duration of the test. As shown by FIG. 5D, the positive sample signal cliff occurs around 17 minutes into the test, with a relatively flat and stable reactance curve 550B leading up to the signal cliff. In contrast, at this same time the negative sample reactance curve 550D exhibits no signal cliff, but rather maintains a quadratic curvature from around t=8 minutes through the end of the test.

Figure 5E:
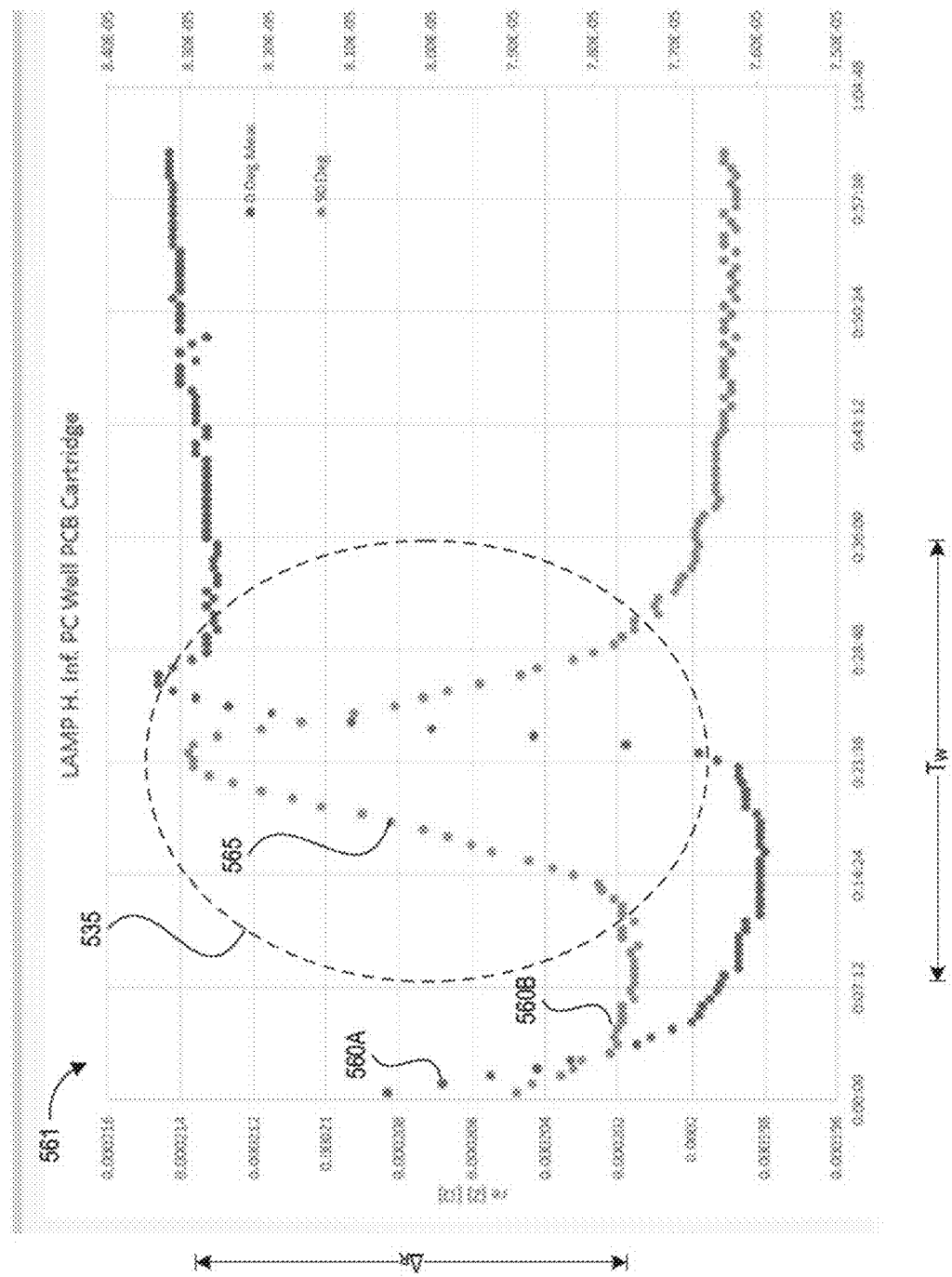
FIG. 5E depicts the resistance and reactance components extracted from a signal as shown in FIG. 5B generated based on another example positive test.

FIG. 5E depicts a plot 561 of the resistance 560A and reactance components 560B over time (t=0 minutes to t=60 minutes since the start of amplification) extracted from a raw signal 520 generated based on an example positive test. As illustrated, the signal cliff 565 represents a change $\Delta_R$ in the reactance 560B during a particular window of time $T_W$. The signal cliff 565 indicates a positive sample. At times occurring prior to the signal cliff 565, the reactance curve 560B is relatively flat or stable, and again after the signal cliff 565 the reactance curve 560B is relatively flat or stable with slight concavity. The signal cliff 565 for the particular test parameters represented by the plot 561 occurs as a peak, spike, or bell curve in the expected region 535, during which the reactance values rise and fall by the $\Delta_R$ value in an approximately parabolic curve. As described herein, varying of certain test parameters (e.g., test well configuration, chemistry and initial quantity of amplification constituents, target, and excitation current characteristics) can vary the geometry of the signal cliff yielded from a positive sample. Thus, in some embodiments the geometry of a "signal cliff" in the reactance values vs time curve can vary from test to test, though for a particular test the curve geometry and/or timing signal cliff remains consistent within reactance change and/or timing parameters across positive samples for that test.

Figure 6:
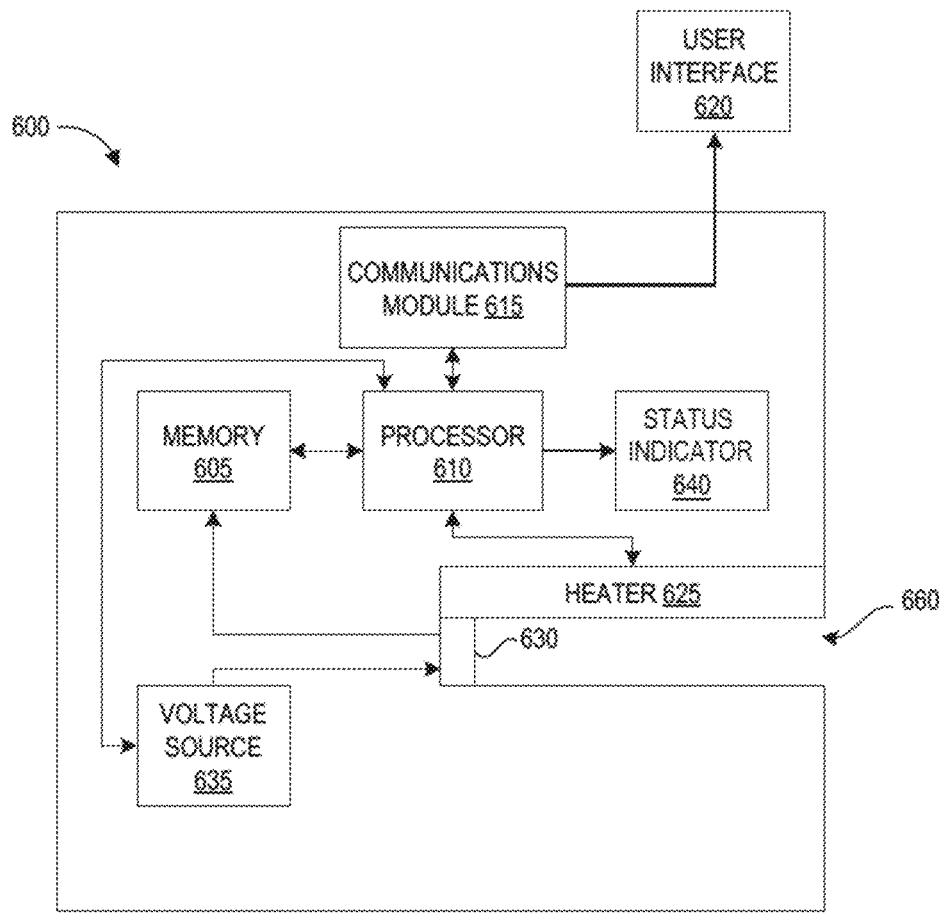
FIG. 6 depicts a schematic block diagram of an example reader device that can be used with the cartridges described herein.

FIG. 6 depicts a schematic block diagram of an example reader device 600 that can be used with the cartridges described herein, for example the cartridges 120 or 200. The schematically illustrated reader device 600 may be, for example, the reader device 110 of FIGS. 1A-1C. The reader device 600 includes a memory 605, processor 610, communications module 615, heater 625, electrode interface 630, voltage source 635, and a cavity 660 into which a cartridge can be inserted. The reader device 600 may further include a status indicator 640. The reader device 600 is in communication with a user interface 620, which may include a user interface of a remote computing device such as a smartphone, tablet, or other device having a testing control application executing thereon.

When test cartridge 120, 200 is inserted into the cavity 660 of the reader device 600, the electrode interface 214 of the cartridge couples with the electrode interface 630 of the reader device 600. This can allow the reader device 600 to detect that a cartridge is inserted, for example by testing whether a communication path is established. In some embodiments, the optional power cartridges described above with reference to FIGS. 1B and 1C may activate a power supply circuit of the reader device 600 when the electrode interface 214 of the cartridge couples with the electrode interface 630 of the reader device 600. Further, such communications can enable the reader device 600 to identify a particular inserted test cartridge 120, 200 and access corresponding testing protocols. Testing protocols can include the duration of the test, the temperature of the test, the characteristics of a positive sample impedance curve, and the information to output to the user based on various determined test results. In other embodiments, the reader device 600 can receive an indication via user interface 620 that a cartridge is inserted (e.g., by a user inputting a "begin testing" command and optionally a test cartridge identifier).

The memory 605 includes one or more physical electronic storage devices configured for storing computer-executable instructions for controlling operations of the reader device 600 and data generated during use of the reader device 600. For example, the memory 605 can receive and store data from sensing electrodes coupled to the electrode interface 630.

The processor 610 includes one or more hardware processors that execute the computer-executable instructions to control operations of the reader device 600 during a test, for example by controlling the heater 625, controlling the communications module 615 to interact with the user interface 620, and activating the voltage source 635. One example of testing operations is described with respect to FIG. 7A below. The processor 610 can be also be configured by the instructions to determine test results based on data received from the excitation electrodes of an inserted test cartridge, for example by performing the process of FIG. 7B described below.

The communications module 615 includes network-enabled hardware components, for example wired or wireless networking components, for providing networked communications between the reader device 600 and remote computing devices. Suitable networking components include WiFi, Bluetooth, cellular modems, Ethernet ports, or USB ports, and the like. Beneficially, networking capabilities can enable the reader device 600 to interact with and be controlled by remote computing devices such as one or more additional handheld computing devices (e.g., smartphones, tablets, etc.). In some embodiments, remote devices may be in communication additional remote computing systems such as hospital information systems and/or laboratory information systems that store electronic medical records, national health agency databases, and the computing devices of clinicians or other designated personnel. In addition, the networking capabilities can enable the reader device 600 to receive information over the network from remote computing devices, for example updated signal cliff parameters for existing test, new signal cliff parameters for new tests, and updated or new testing protocols.

The user interface 620 can be implemented within a remote device connected to the communications module 615 via WiFi, or Bluetooth, or the like. The remote device may have a testing control application installed thereon to provide a testing system user interface, for providing control options and/or presenting test results and other test information to users, on a display of the remote device. Further details of the user interface 620 are described with reference to FIGS. 8A-8D and FIGS. 15A-15P.

The heater 625 can be positioned adjacent to the cavity 660 for heating an inserted cartridge to the desired temperature for an amplification process. Though depicted on a single side of the cavity 660, in some embodiments the heater 625 can surround the cavity.

As described herein, the voltage source 635 can provide an excitation signal at a predetermined voltage and frequency to the excitation electrode of an inserted test cartridge.

The status indicator 640 may include any suitable notification device, such as one or more lights, sound generators, or the like. Operation of a light-based status indicator is described in greater detail with reference to FIGS. 1A-1C.

Figure 7A:
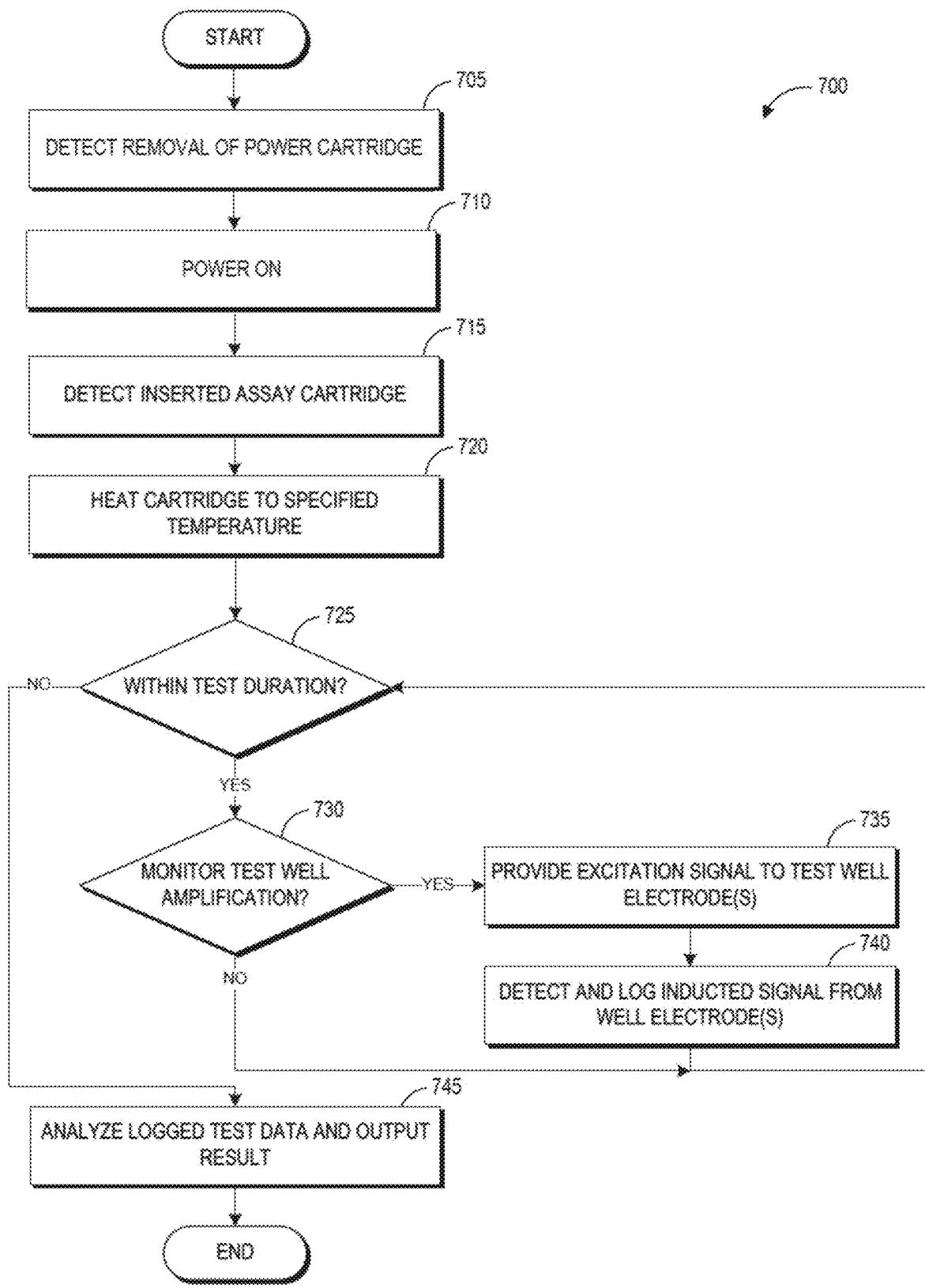
FIG. 7A depicts a flowchart of an example process for operating a reader device during a test as described herein.

FIG. 7A depicts a flowchart of an example process 700 for operating a reader device during a test as described herein. The process 700 can be performed by the reader device 600 described above.

At block 705, the reader device 600 can detect that a power cartridge has been removed from the reader device 600. In some embodiments, the detection of block 705 can occur based on the disconnection of a signal path between the electrode interface 630 of the reader device 600 and one or more contact pads $214_1$-$214_5$ (FIG. 2D) of the power cartridge.

At block 710, the reader device 600 automatically powers on in response to detecting the removal of the power cartridge at block 705. In some embodiments, the reader device may transmit a notification to a user interface 620 device and/or illuminate one or more status lights of a status indicator 640 to indicate that the reader device 600 is powered on and ready to receive an assay cartridge 120, 200.

At block 715, the reader device 600 can detect that an assay cartridge 120, 200, has been inserted, for example in response to user input or in response to establishing a signal path with the inserted cartridge. In some embodiments, the cartridge 120, 200 can include an information element that identifies the particular test(s) to be performed to the reader device 600 and optionally includes test protocol information.

At block 720, the reader device 600 can heat the cartridge 120, 200 to a specified temperature for amplification. For example, the temperature can be provided by information stored on the cartridge 120, 200 or accessed in the internal memory of the reader device 600 in response to identification of the cartridge 120, 200.

At decision block 725, the reader device 600 can determine whether the test is still within its specified test duration. For example, where the expected window of time in which a signal cliff should appear in a positive sample is known, the duration of the test may end at or some predetermined period of time after the end of the window. If so, the process 700 transitions to optional decision block 730 or, in embodiments omitting block 730, to block 735.

At optional decision block 730, the reader device 600 determines whether to monitor the test well amplification by logging data from the test well sensing electrode. For example, the reader 600 may be provided with instructions to only monitor the impedance of the test well during a particular window or windows of a test. If the reader device 600 determines not to monitor the test well amplification, the process 700 loops back to decision block 725.

If the reader device 600 determines to monitor the test well amplification, the process 700 transitions to block 735. At block 735, the reader device 600 provides an excitation signal to the excitation electrode of the test well(s) of the inserted cartridge. As described above, this can be an alternating current at a particular frequency and voltage.

At block 740, the reader device 600 detects and logs data from the sensing electrode of the test well(s) of the inserted cartridge. In some embodiments, this data can be stored for later analysis, for example after completion of the test. In some embodiments, the reader device 600 can analyze this data in real time (e.g., as the test is still occurring) and may stop the test once a positive sample signal cliff is identified.

When the reader device 600 determines at block 725 that the test is not still within its specified duration, the process 700 moves to block 745 to analyze the test data and output the test result. The test result can include an indication that the sample tested positive or negative for the target, or can more specifically indicate an estimated quantity of the target in the tested sample. Following the conclusion of the test, further tests may be performed by returning to block 715 for a new assay cartridge. Alternatively, the reader device 600 may detect insertion of a power cartridge and power off in response.

Figure 7B:
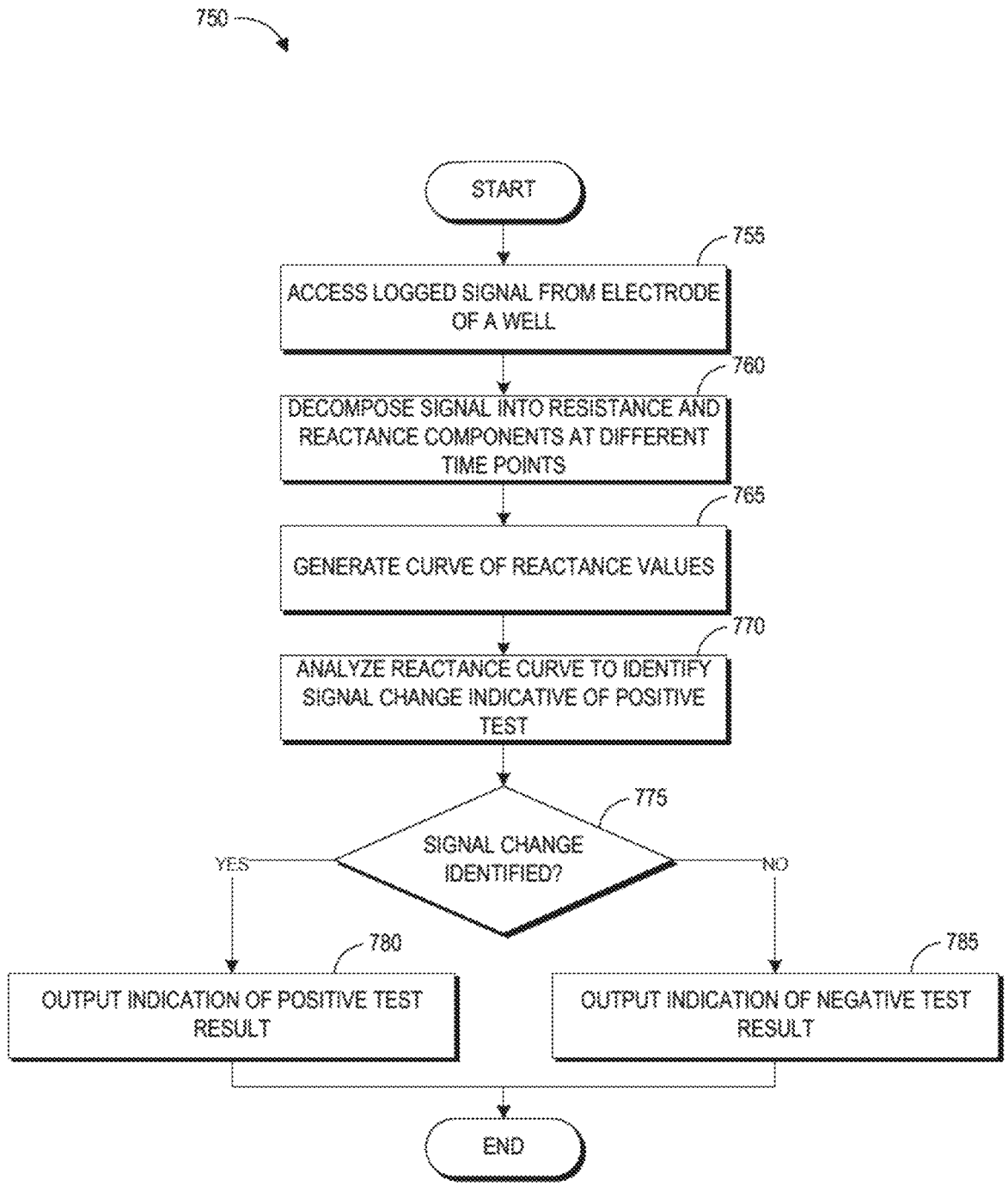
FIG. 7B depicts a flowchart of an example process for analyzing test data to detect a target as described herein.

FIG. 7B depicts a flowchart of an example process 750 for analyzing test data to detect a target as described herein that can be performed by the reader device 600 as block 745 of FIG. 7A.

At block 755, the reader device 600 can access logged signal data received from the electrode of a well.

At block 760, the reader device 600 can decompose the signal into resistance and reactance components across some or all of the different time points of the test. For example, as described above, at each time point the reader device 600 can determine in phase and out of phase components of the raw sampled voltage waveform and can then deconvolute these components using known series resistance of the electrode circuit to calculate the in-phase (resistance) and out-of-phase (reactance) portions of the impedance of the test well.

At block 765, the reader device 600 can generate a curve of the reactance values over time. Also at block 765, the reader device 600 can optionally generate a curve of the resistance values over time.

At block 770, the reader device 600 can analyze the reactance curve to identify a signal change indicative of a positive test. As described above with respect to the signal cliff of FIG. 5C, the reader device 600 can look for greater than a threshold change in reactance, can look for such a change within a predetermined window of time, can analyze the slope of the reactance curve at a predetermined time, or can analyze the overall shape of the reactance curve in order to determine whether a signal cliff (e.g., a rise or drop in the signal preceded and followed by relatively more stable values) is present.

At decision block 775, based on the analysis performed at block 770, the reader device 600 can determine whether the sought-after signal change was identified in the reactance curve. If so, the process 750 transitions to block 780 to output an indication of a positive test result to the user. If not, the process 750 transitions to block 785 to output an indication of a negative test result to the user. The result can be output locally, for example on the display of the device, or output over a network to a designated remote computing device.

FIGS. 8A-8D depict screens of an example graphical user interface 800 of a user device implementing an example testing process in communication with a reader device as described herein. The user interface 800 may be, for example, the user interface 620 illustrated in connection with the reader device 600 of FIG. 6. The user interface 800 may be implemented with any of the reader devices 110, 600 and/or assay cartridges 120, 200 described herein. The screens depicted in FIGS. 8A-8D may be displayed, for example, by an application executing on a smartphone or other user interface device paired to the reader device 110, 600 (e.g., by WiFi, Bluetooth, or the like) so as to allow a user to control and/or monitor the reader device 110, 600 from the user interface device.

Figure 8B:
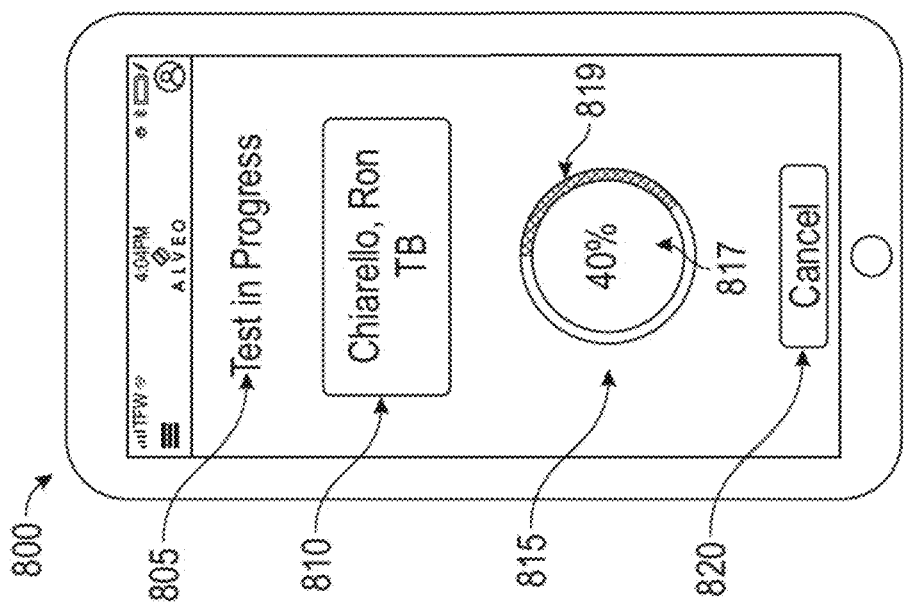
FIGS. 8A-8D depict an example user interface of a user device implementing an example testing process in communication with a reader device as described herein.
Figure 8A:
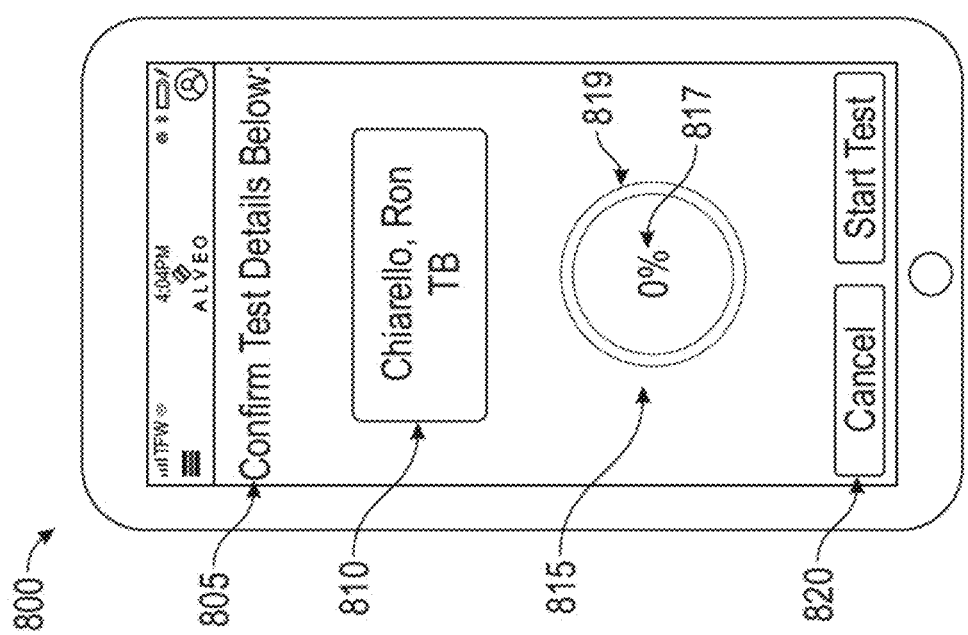

FIG. 8A depicts an initial pre-test screen which may be displayed after an inserted assay cartridge 120, 200 has been detected. In one example, a user scans a cartridge identifier (e.g., cartridge identifier 215 of FIG. 2B) of a cartridge before inserting the cartridge into the reader device. When the device is inserted, the paired reader device detects the inserted cartridge and sends a message to the user interface device that the cartridge has been inserted. The application then displays the initial pre-test screen depicted in FIG. 8A.

The initial pre-test screen includes a status indication area 805, a test identifying area 810, a progress indication area 815 including a numeric progress indication 817 and a graphical progress indication 819, and an input area 820. The status indication area 805 may include an instruction, such as a request for the user to confirm the information in the test identifying area 810. The test identifying area 810 includes information associated with the test to be performed, such as a name or other identifier of a test subject, a condition or target agent to be detected, or the like. In the initial pre-test screen of FIG. 8A, the input area 820 includes user-selectable "cancel" and "start test" options to allow the user to cancel the test or confirm the details and start the test.

FIG. 8B depicts a mid-test screen that may be displayed while the reader device is conducting the test on the fluid sample within the cartridge. The status indication area 805 indicates that the test is in progress. As the test progresses, the numeric progress indication 817 and the graphical progress indication 819 are updated to display the current progress of the test. A user-selectable option to cancel the test is provided in the input area to allow a user to stop the test if desired.

Figure 8D:
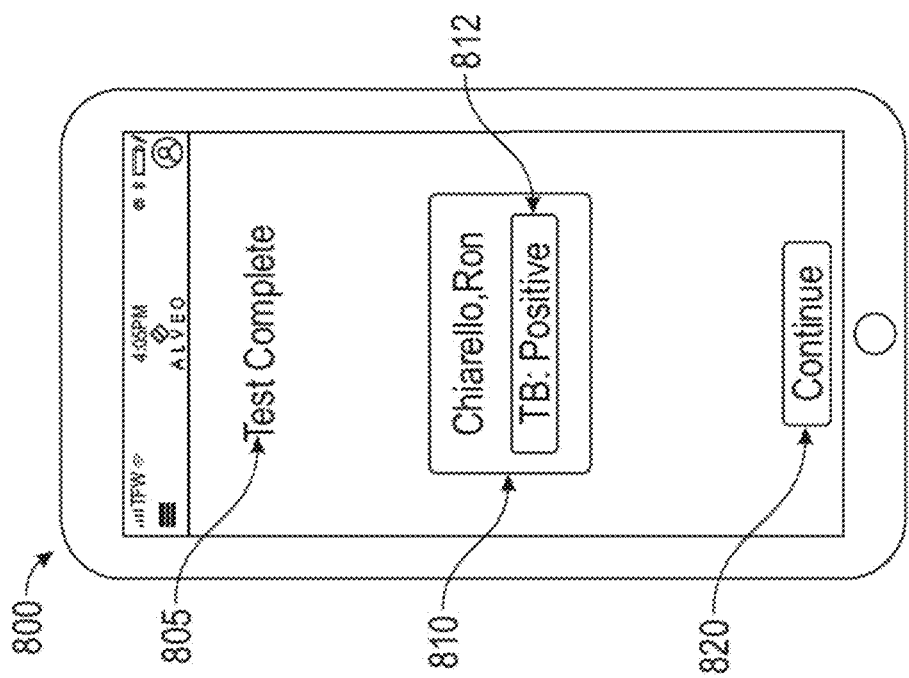
Figure 8C:
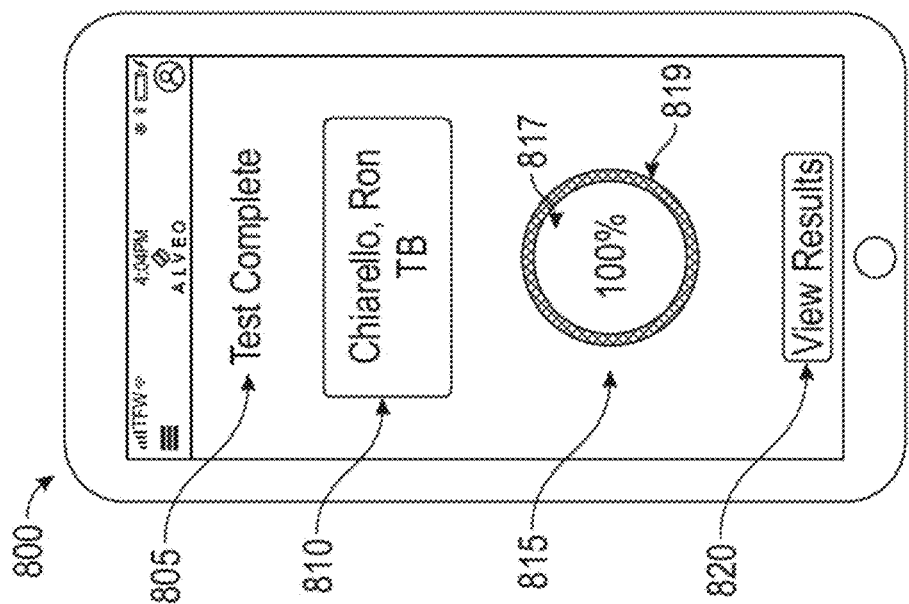

FIG. 8C depicts an initial test completion screen that may be displayed when the reader device has completed the test and has analyzed the logged test data to determine a test result. The status indication area 805, numerical progress indication 817, and/or the graphical progress indication 819 may indicate that the test is complete. In the input area 820, a user-selectable option to view the test results is provided.

FIG. 8D depicts a test result display screen for communicating the results of the test to a user. The test identifying area 810 may still display some or all of the originally displayed test identifying information. The test identifying area 810 may additionally display an outcome 812, such as positive or negative, or other condition associated with the test results. The input area 820 may provide a user-selectable option to continue (e.g., to conduct additional tests, transmit results, etc.).

Figure 9A:
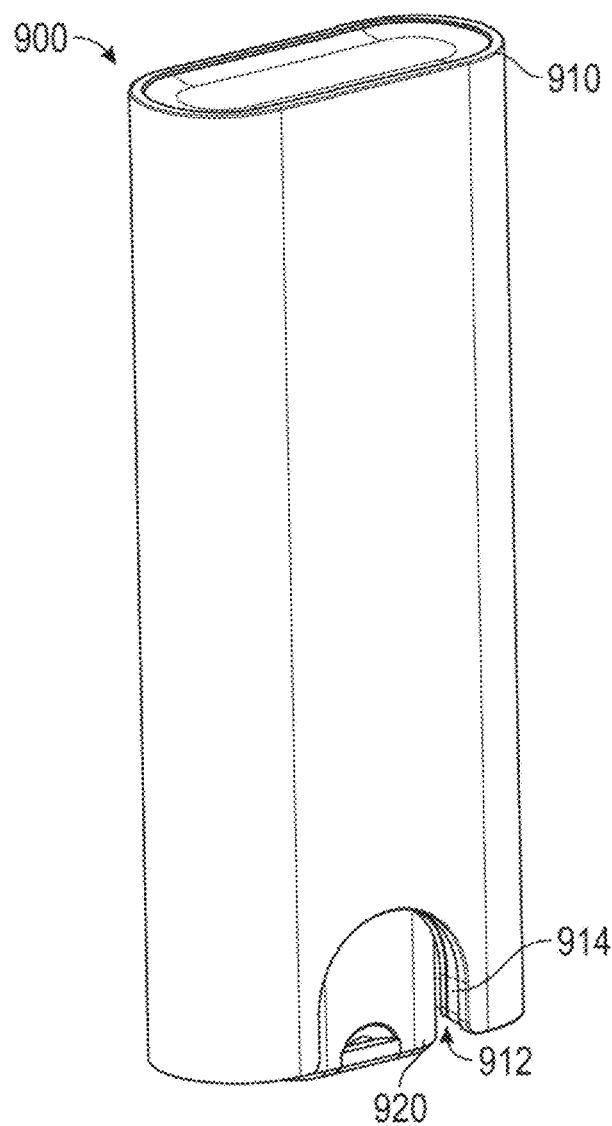
FIGS. 9A and 9B depict an example handheld system for detection of a target.
Figure 9B:
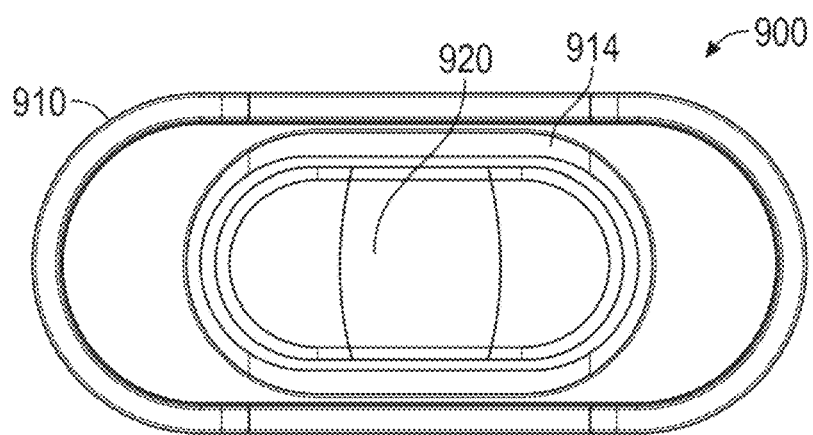

FIGS. 9A and 9B depict a further example of a handheld detection system 900 for detection of a target. Similar to the system 100 of FIGS. 1A-1C, the system 900 may be implemented in conjunction with any of the target detection processes, systems, and devices described herein. The system 900 includes a reader device 910 and a cartridge 920 configured to fit within a cavity 912 of the reader device 910. The cartridge 920 is sized and shaped to be gripped by a user to facilitate insertion and/or removal of the cartridge 920 from the reader device 910. The reader device 910 may further include a light ring 914 disposed about the cavity 912. The light ring 914 may include any or all of the light sources, colors, operation modes, etc., described above with reference to the light ring 114 of FIGS. 1A-1C.

FIGS. 10A-10K depict an example cartridge 1000 configured for detection of a target. As described herein, the target may be a viral target, bacterial target, antigen target, parasite target, microRNA target, or agricultural analyte. Some embodiments of the cartridge 1000 can be configured for testing for a single target, while some embodiments of the cartridge 1000 can be configured for testing for multiple targets. The cartridge 1000 includes a cartridge body 1010 and a cap 1050 configured to be mechanically coupled to the cartridge body 1010. The cartridge body 1010 and the cap 1050, when coupled together, can form an assembled cartridge 1000 for insertion into a reader device such as the reader device 910 of FIGS. 9A and 9B. As will be described in greater detail below, the cartridge body 1010 may include a plurality of test wells therein, such that a single cartridge 1000 can be configured for testing a single sample for multiple targets.

Figure 10A:
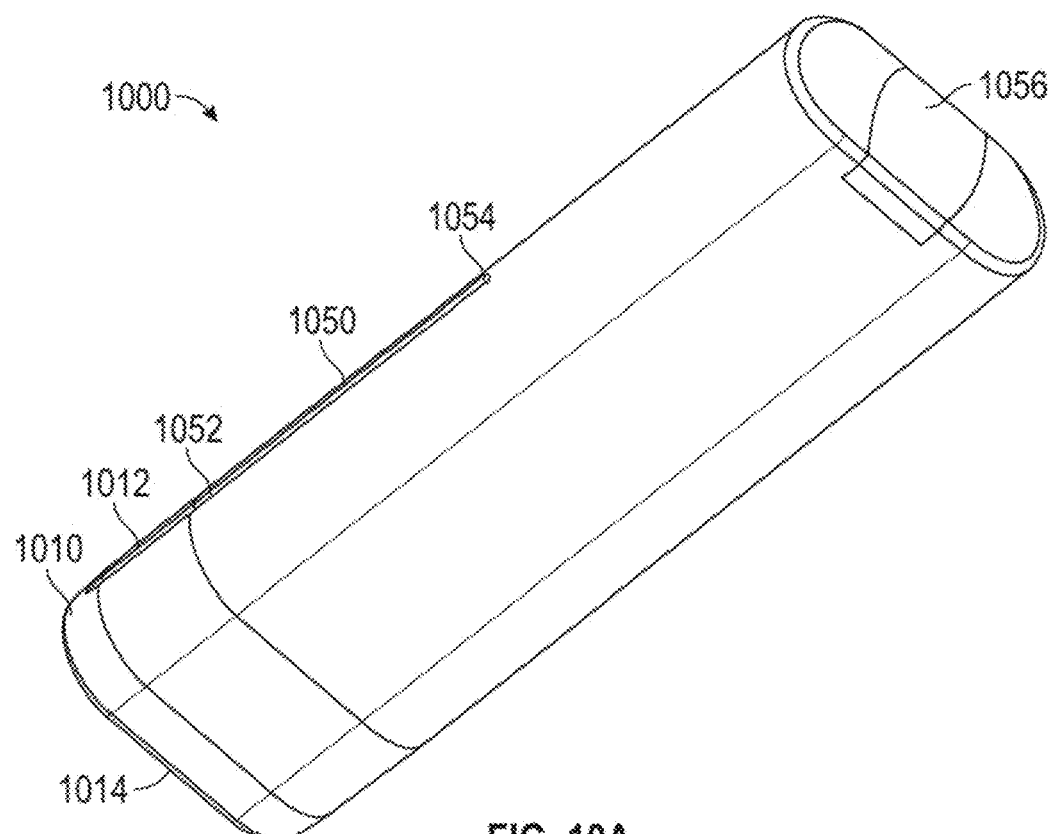
FIGS. 10A-10K depict an example cartridge for detection of a target that can be used in the handheld system of FIGS. 9A and 9B.
Figure 10B:
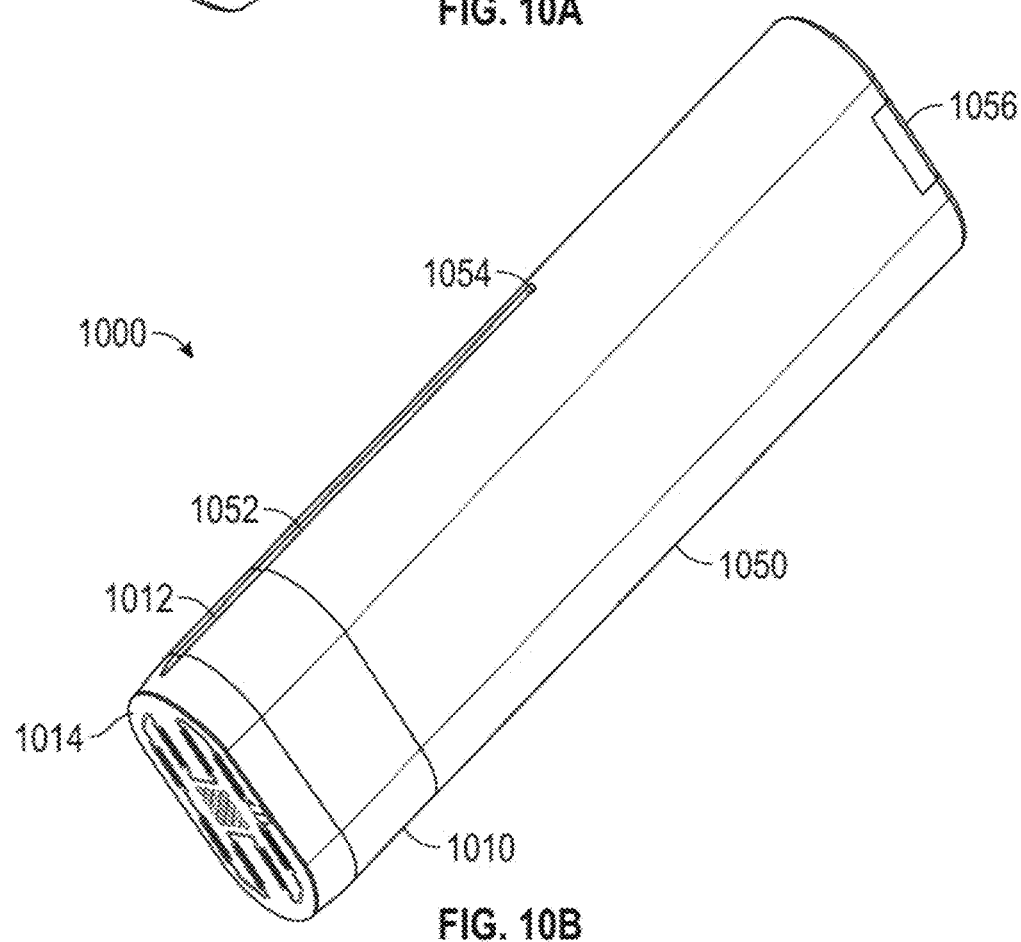

FIGS. 10A and 10B depict a complete cartridge 1000 including the cartridge body 1010 and the cap 1050 coupled together. In use, the cap 1050 and the cartridge body 1010 can operate to seal a provided sample within the cartridge 1000, thereby preventing exposure of test operators to the sample and preventing any liquid from escaping into the electronics of an associated reader device. The cartridge body 1010 and the cap 1050 may be coupled by a friction fit, a snap fit, and/or one or more mechanical or chemical securing means. Coupling of the cartridge body 1010 and the cap 1050 is discussed in greater detail with reference to FIGS. 11A-11D.

The cartridge body 1010 and the cap 1050 can be formed from suitable fluid-impermeable materials such as plastic, metals, or the like, and may be opaque, translucent, or transparent. The cartridge body 1010 can also include a transparent, translucent, or opaque cover surface such as a printed circuit board (PCB) 1014 or other surface partially defining a fluid path within the cartridge body 1010. The PCB 1014 and fluid paths are discussed in greater detail with reference to FIGS. 10E-10K. The cartridge body 1010 and/or the cap 1050 can further include a cartridge identifier 1011. The cartridge identifier 1011 may include human-readable and/or machine-readable information, such as text, a barcode, a QR code, or the like. The cartridge identifier 1011 can include any suitable information associated with the cartridge, such as information specifying a type of test, a target agent, a sample type, a cartridge serial number or other individual cartridge identifier, etc. In addition to serving as an identifier for a user of the type of test associated with the cartridge 1000, the cartridge identifier 1011 may also be scanned by a user (e.g., using a user interface device in communication with a reader device) to communicate one or more test protocols to the reader device.

The cartridge body 1010 and/or the cap 1050 can include ergonomic features such as an indentation or the like to facilitate handling of the cartridge 1000. In the example cartridge 1000 depicted, the cartridge body 1010 further includes an alignment groove 1012 located to align with an alignment groove 1052 of the cap 1050. The alignment groove 1052 of the cap 1050 terminates at a stop 1054 configured to engage a protrusion within a corresponding reader device (e.g., the reader device 910 of FIGS. 9A and 9B) to define a fully inserted position of the cartridge 1000 within the reader device. The cap 1050 can further include a sample receiving area cap 1056 sized and shaped to sealingly close an opening in the cap 1050 for receiving a swab or other sample carrying holding a sample to be analyzed.

Figure 10C:
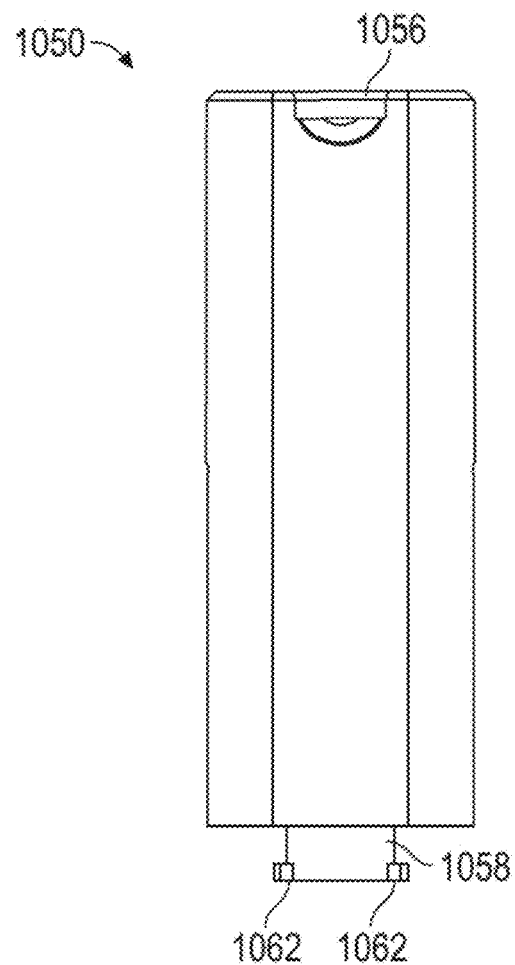
Figure 10D:
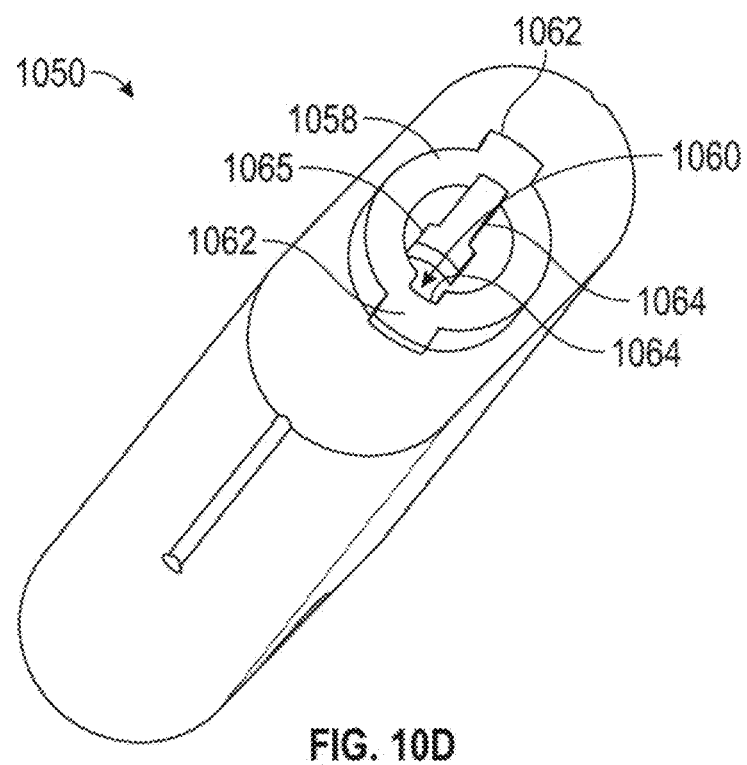

FIGS. 10C and 10D depict the cap 1050 component of the cartridge 1000 of FIGS. 10A and 10B. The cap 1050 comprises an elongate body which is at least partially hollow to receive a sample carrier such as a swab or the like. An opening in the cap 1050 for receiving the sample carrier may be sealed by the sample receiving area cap 1056, which may include one or more O-rings or other resilient structures to sealingly block the opening in the cap 1050.

The cap 1050 further includes a collar 1058 protruding from the cap 1050. The collar 1058 is sized and shaped to facilitate coupling with the cartridge body 1010. The collar 1058 generally comprises a hollow cylindrical body defining a plunger receiving well 1060 through which the fluid sample may pass from the cap 1050 into the cartridge body 1010. The collar 1058 includes interlocking fins 1062 extending radially outward from an exterior surface of the collar 1058, and receiving channels 1064 within the an interior surface of the collar 1058. Each receiving channel 1064 terminates in a widened section 1065 such that the receiving channels 1064 are configured to receive and retain one or more snap-fit connectors of the cartridge body 1010, as will be described with reference to FIGS. 11A-11D.

The cap 1050 may further include one or more liquid constitutent therein to be mixed with a received sample. For example, liquid constituents may include one or more amplification reagents, buffer solutions, water, mucin mitigating agents, or other desired liquid constituents for the testing process. The particular selection and chemistry of these liquids can be tailored to a particular target or targets for which the cartridge 1000 is designed to test. In some embodiments, the liquid constituents may be contained within a blister pack within the cap 1050. The blister pack may be punctured by, for example, insertion of a sample carrier, coupling of the cap 1050 to the cartridge body 1010, etc.

Figure 10E:
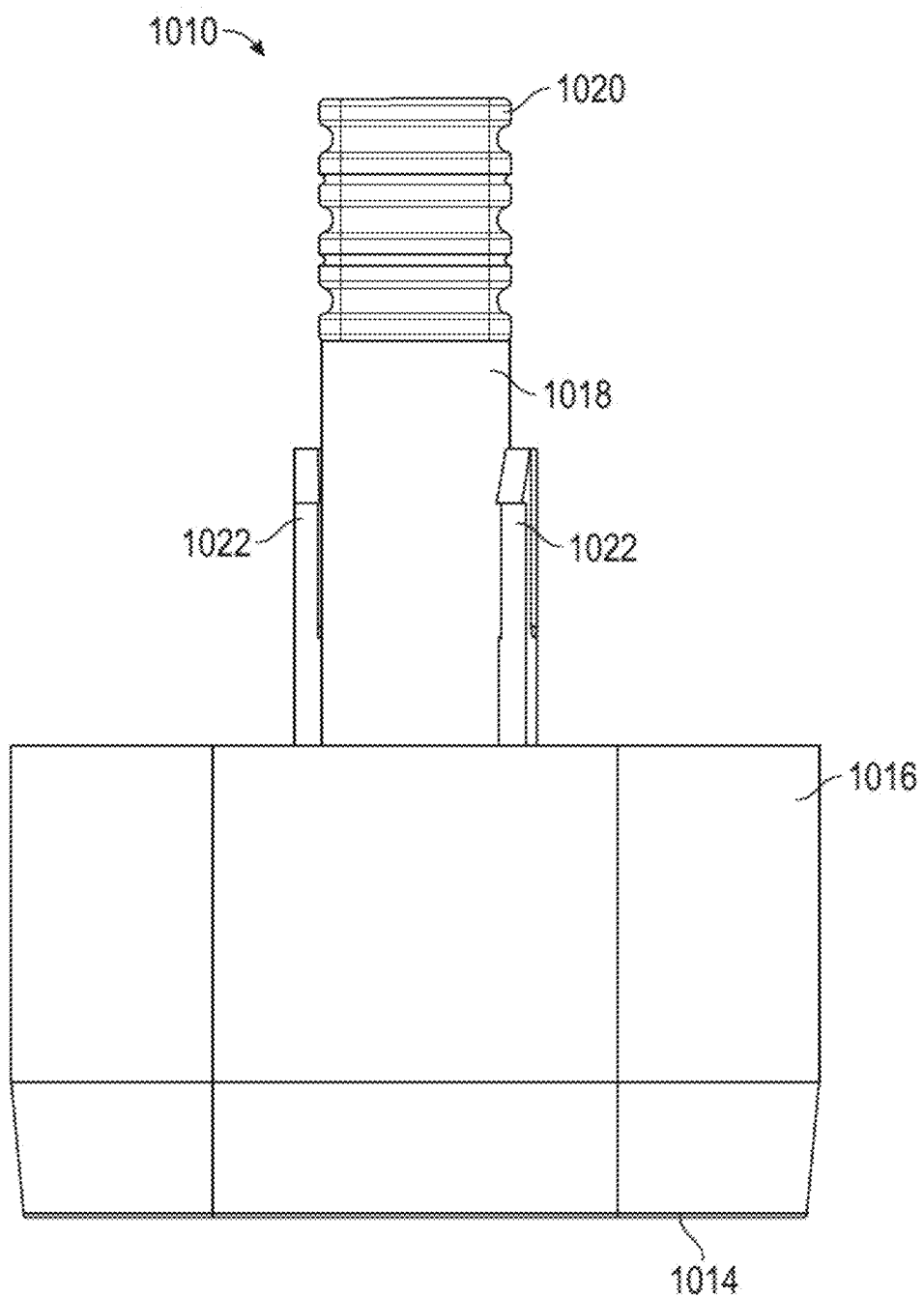
Figure 10F:
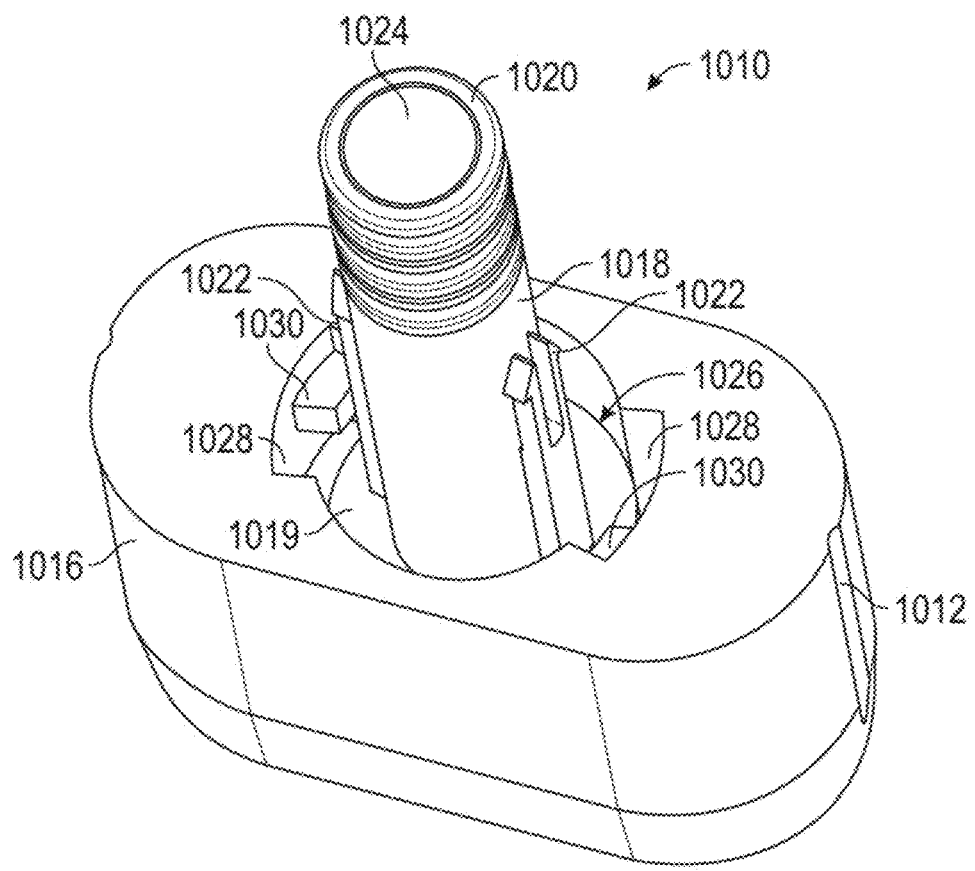
Figure 10G:
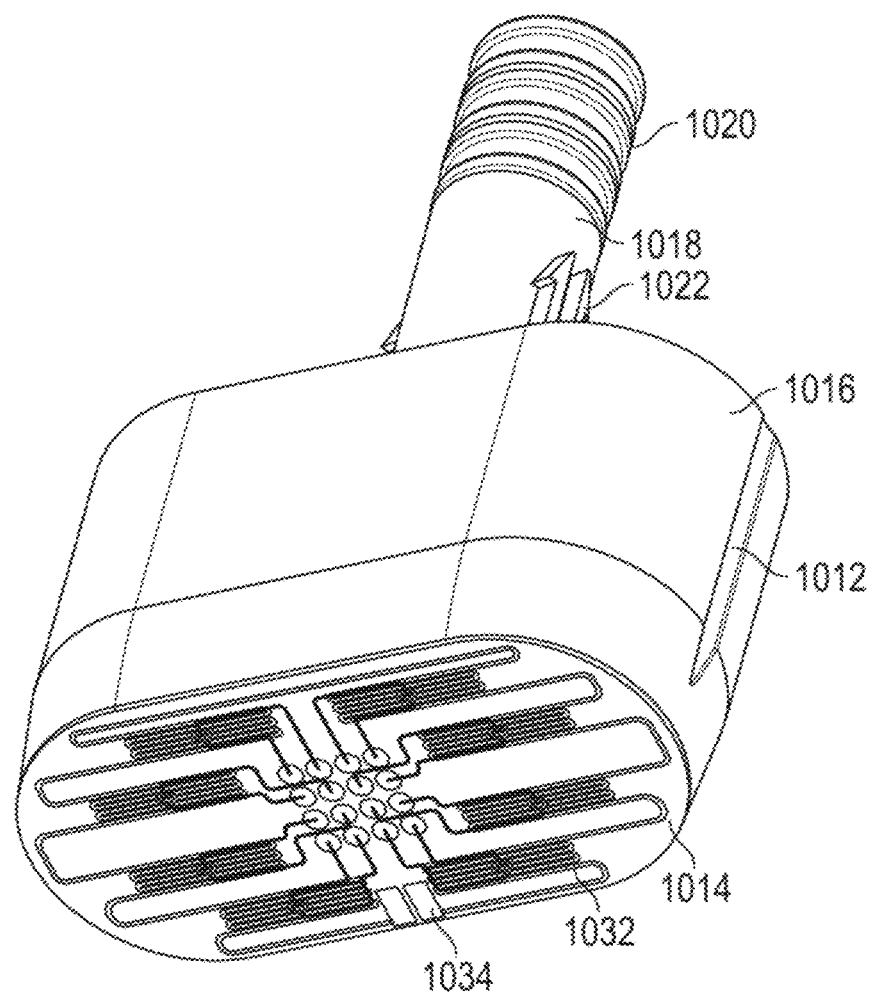
Figure 10H:
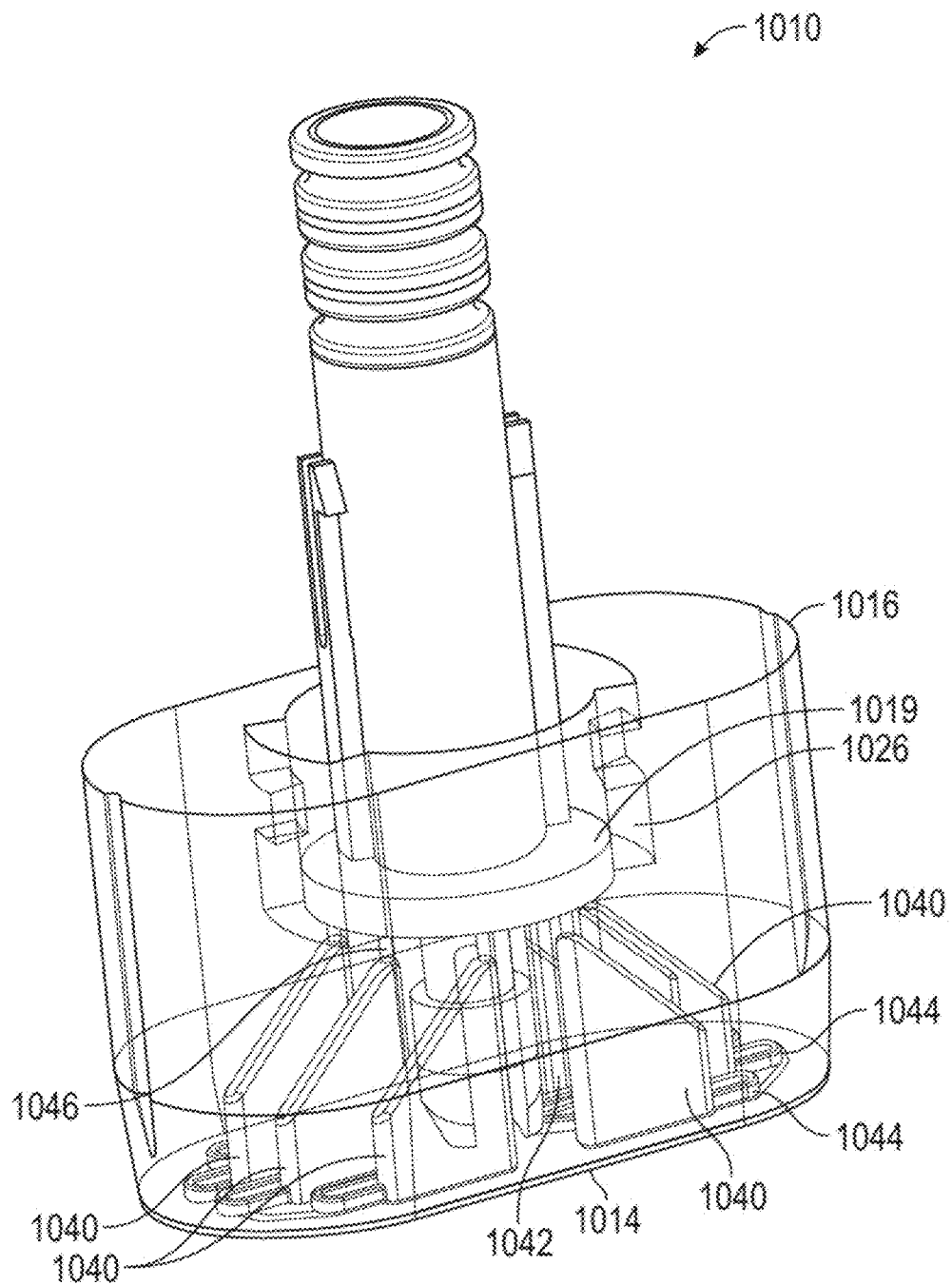
Figure 10I:
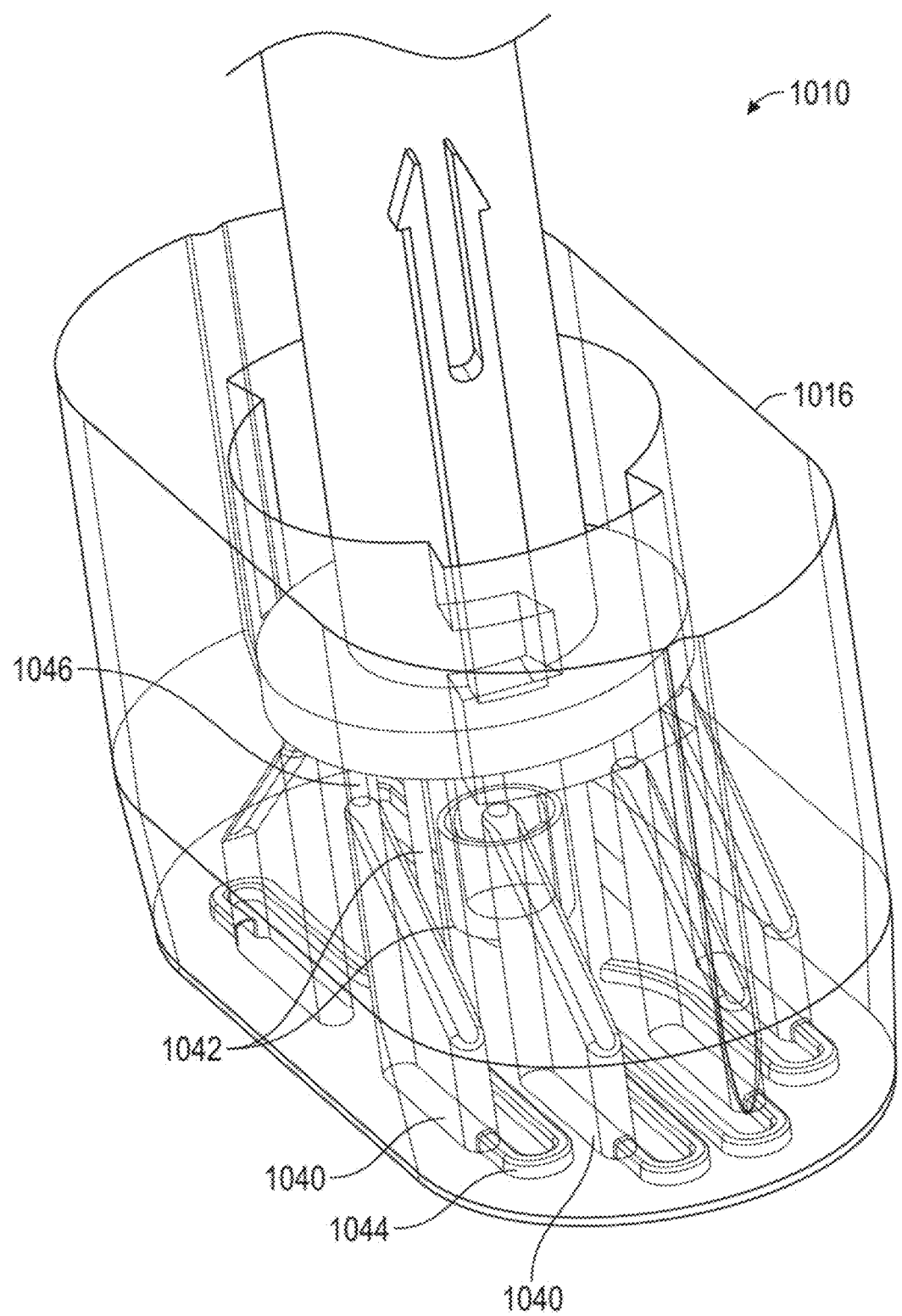
Figure 10J:
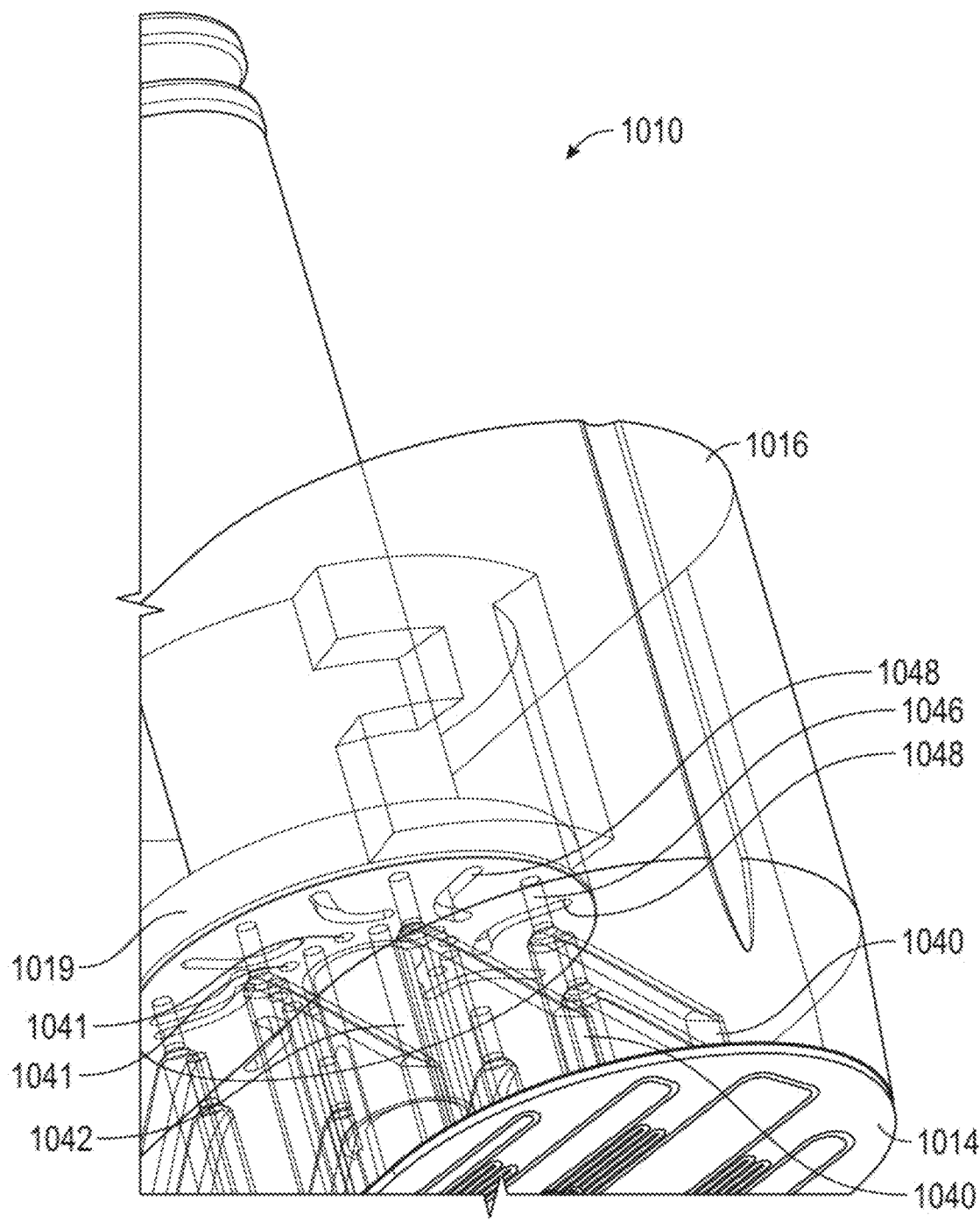
Figure 10K:
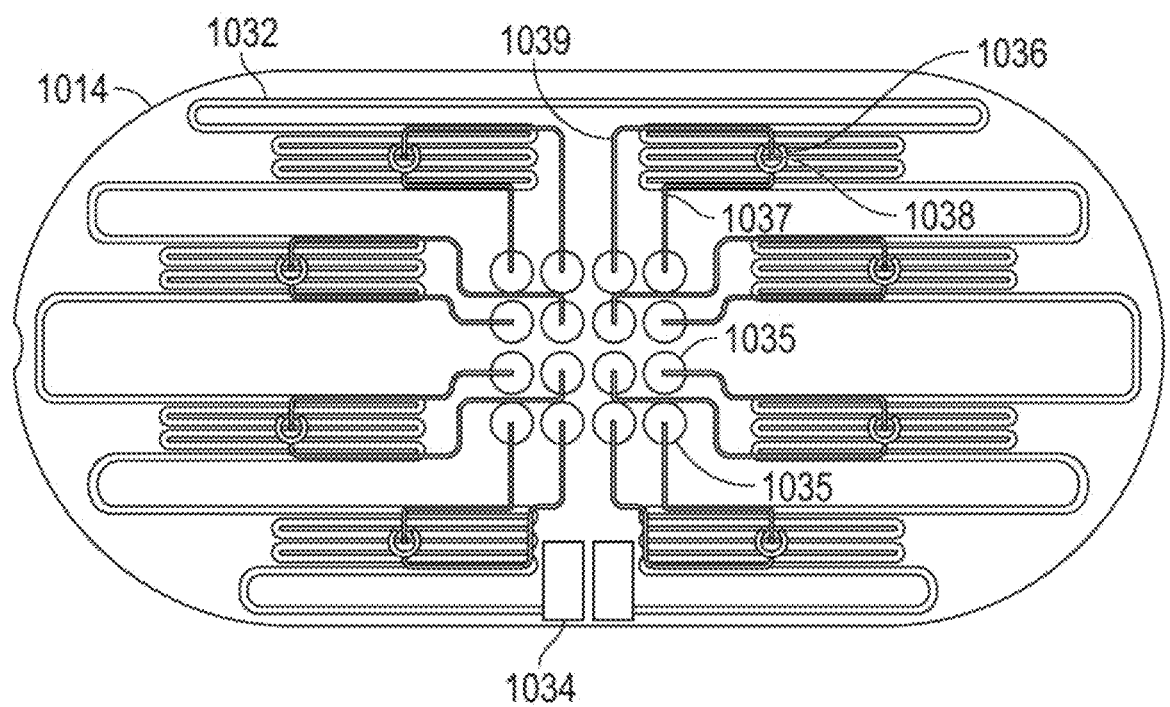

FIGS. 10E-10K depict the cartridge body 1010 component of the cartridge 1000 of FIGS. 10A and 10B. FIGS. 10E-10G are exterior views of the cartridge body 1010. FIGS. 10H-10J depict the cartridge body 1010 with partial translucency to illustrate fluid paths integrally formed therein. FIG. 10K is an enlarged view depicting the PCB 1014 of the cartridge body 1010. Referring to FIGS. 10E-10G, the cartridge body 1010 includes a base 1016 and a hollow plunger 1018 rotatably coupled within a receiving well 1026 of the base such that the plunger 1018 can rotate about its longitudinal axis while being retained within the receiving well 1026.

The plunger 1018 comprises a generally cylindrical body sized and shaped to fit within the plunger receiving well 1060 of the cap 1050 (FIGS. 10C and 10D). A sealing portion 1020 of the plunger 1018 is disposed at a distal end of the plunger 1018 and may include one or more resilient structures (e.g., one or more O-rings, integrally formed elastomeric structures, etc.) having an appropriate diameter to sealingly engage with the interior walls of the plunger receiving well 1060 of the cap 1050. A sacrificial seal 1024 such as a layer of a metallic foil or other thin material may be provided to prevent exposure of the interior of the cartridge body 1010 to the atmosphere prior to use. The plunger 1018 additionally includes one or more snap-fit clips 1022 extending along the exterior of the plunger 1018 parallel to the longitudinal axis of the plunger. The snap-fit clips 1022 are sized and shaped to engage within and be retained by the receiving channels 1064 of the plunger receiving well 1060 of the cap 1050. A plunger baseplate 1019 is rotationally fixed to the plunger 1018 (e.g., may be integrally formed with the plunger 1018). The diameter of the plunger baseplate 1019 may be substantially equal to or slightly larger than the outer diameter of the collar 1058 of the cap 1050.

In some embodiments, one or more liquid constituents may be included within the plunger 1018, instead of or in addition to liquid constituents included within the cap 1050. For example, the sacrificial seal 1024 may contain the liquid constituents within the plunger 1018 and/or the liquid constituents may be contained within a blister pack within the plunger 1018. Liquid constituents contained within the plunger may include one or more amplification reagents, buffer solutions, water, mucin mitigating agents, or other desired liquid constituents for the testing process. The particular selection and chemistry of these liquids can be tailored to a particular target or targets for which the cartridge 1000 is designed to test. The blister pack may be punctured by, for example, insertion of a sample carrier, coupling of the cap 1050 to the cartridge body 1010, etc.

The receiving well 1026 is coaxial with the plunger 1018 and has a generally cylindrical profile with a diameter substantially equal to or slightly larger than the plunger baseplate 1019 and/or the collar 1058 of the cap 1050. The receiving well 1026 further includes cutouts 1028 sized to receive the interlocking fins 1062 of the cap 1050. Stops 1030 within the cutouts 1028 are disposed within the cutouts 1028 to block longitudinal motion of the interlocking fins 1062 in certain rotational positions, as will be described in greater detail with reference to FIGS. 11A-11D.

FIGS. 10H-10J depict additional views of the cartridge body 1010 in which the base 1016 is illustrated with transparency to show the fluid paths contained therein. The base 1016 may comprise any suitable liquid-impermeable material, such as plastic or metal. The base 1016 may be formed by one or more processes such as injection molding, die casting, milling, or the like, such that the depicted fluid paths can be integrally formed therein.

The base 1016 of FIGS. 10H-10J includes eight substantially identical fluid paths, each fluid path including a test well 1040. Various embodiments may include fewer than eight or more than eight fluid paths and test wells 1040 without departing from the scope of the present disclosure. For example, a base 1016 may include 1, 2, 3, 4, 5, 6, 7, 9, 10, 11, 12, or more fluid paths. Multiple identical or similar fluid paths within the base may accommodate simultaneous testing for a plurality of different targets and/or a plurality of simultaneous tests for the same target (e.g., to improve reliability of results).

Each fluid path includes an inlet channel 1042, a lateral channel 1044, a test well 1040, and an outlet channel 1046. Each inlet channel 1042 extends vertically through the base 1016 to fluidically connect a first end adjacent to the plunger baseplate 1019 to an opposite end adjacent to the PCB 1014. Each lateral channel 1044 fluidically connects an inlet channel 1042 to the corresponding test well 1040. Each outlet channel 1046 extends vertically from a test well 1040 to fluidically connect the test well 1040 to the bottom of the plunger baseplate 1019. In the cartridge body 1010 of FIGS. 10H-10J, the PCB 1014 forms a boundary partially defining each lateral channel 1044 and each test well 1040. In this example embodiment, the PCB 1014 may be oriented with the electrodes 1036, 1038 on the side adjacent to the cartridge body 1010 such that the electrodes 1036, 1038 are in contact with the interior of the test wells 1040.

As shown in FIG. 10J, each inlet channel 1042 is disposed radially outward from the longitudinal axis of the plunger baseplate 1019 at substantially the same distance as an array of sample inlets 1041 of the plunger baseplate 1019. Similarly, each outlet channel 1046 is disposed radially outward from the longitudinal axis of the plunger baseplate 1019 at substantially the same distance as the outer ends of an array of J-shaped sample outlets 1048 of the plunger baseplate 1019. The sample inlets 1041 and the inner ends of the J-shaped sample outlets 1048 are fluidically connected through the plunger baseplate 1019 to one or more interior spaces within the plunger 1018. Accordingly, when the plunger baseplate 1019 is rotated to an engaged position, as will be described with reference to FIGS. 11B and 11C, the sample inlets 1041 align with the inlet channels 1042, and the sample outlets 1048 align with the outlet channels 1046, such that a fluid sample within the plunger 1018 can flow into and fill the fluid paths within the base 1016 of the cartridge body 1010.

FIG. 10K illustrates components of the PCB 1014, which may be disposed along a surface of the cartridge body 1010 opposite the receiving well 1026 as shown in FIGS. 10E-10K. In some embodiments, the PCB 1014 may perform heating and/or electrode interface functions, and may further serve as a boundary for one or more fluid paths within the cartridge body 1010. Although the example PCB 1014 depicted herein includes heating and electrode interface functionality, these functions may equally be performed by two or more discrete elements in the cartridge body 1010. In some embodiments, heating may be achieved by heating elements located within a corresponding reader device instead of or in addition to heating elements disposed on or in the cartridge 1000.

The PCB 1014 comprises a generally planar surface having one or more traces disposed thereon in one or more layers. For example, the PCB 1014 may include one or more flex circuits, rigid printed circuit boards, or any other suitable circuitry including one or more current paths disposed on a generally planar substrate. One or more heating traces 1032 electrically connect test well heating elements 1033 to heating current pads 1034. The heating current pads 1034 may come into contact with contacts of a current source of a reader device when the cartridge 1000 is inserted into the reader device, such that a current may be provided to the test well heating elements 1033 to heat fluid samples in one or more test wells of the cartridge body 1010.

The PCB 1014 further comprises a pair of electrodes 1036, 1038 (e.g., an excitation electrode and a sensor electrode) corresponding to each test well. In some embodiments, the electrodes 1036, 1038 may be in direct contact with the fluid sample in each test well if the PCB 1014 serves as a boundary for the test wells. Each electrode 1036, 1038 is electrically connected to an electrode interface pad 1035 by electrode traces 1037, 1039 of the PCB 1014.

In various embodiments, the PCB 1014 may include one or more layers. For example, in some embodiments the PCB is a flex circuit comprising an electrode layer and a heating layer separated from the electrode layer. The electrode layer may include the electrodes 1036, 1038 as well as the electrode traces 1037, 1039 and/or the electrode interface pads 1035. The heating layer may include the heating elements 1033, heating traces 1032, and/or heating current pads 1034. In some aspects, the electrode layer and the heating layer may be disposed on opposite sides of a common substrate, or may be provided on separate substrates. Preferably, the PCB 1014 may be disposed such that the electrode layer including the electrodes 1036, 1038 is adjacent to the cartridge body 1010 and the electrodes 1036, 1038 are fluidically connected to the test wells 1040.

FIGS. 11A-11lD illustrate mechanical fluid transfer aspects of the cartridges 920, 1000 described herein. Similar to the fluid transfer aspects described with reference to FIGS. 3A-3E, the cartridge body 1010 and cap 1050 are configured to create air pressure when coupled together, such that the air pressure propels a fluid sample through the fluid paths of the cartridge body 1010. The cap 1050 is illustrated with translucency in FIGS. 11A-11D, and the cartridge body 1010 is illustrated with translucency in FIGS. 11C and 11D, to reveal interior features of the cap 1050 and cartridge body 1010. The cartridge body 1010 is depicted with the PCB 1014 removed in FIG. 11C.

Figure 11A:
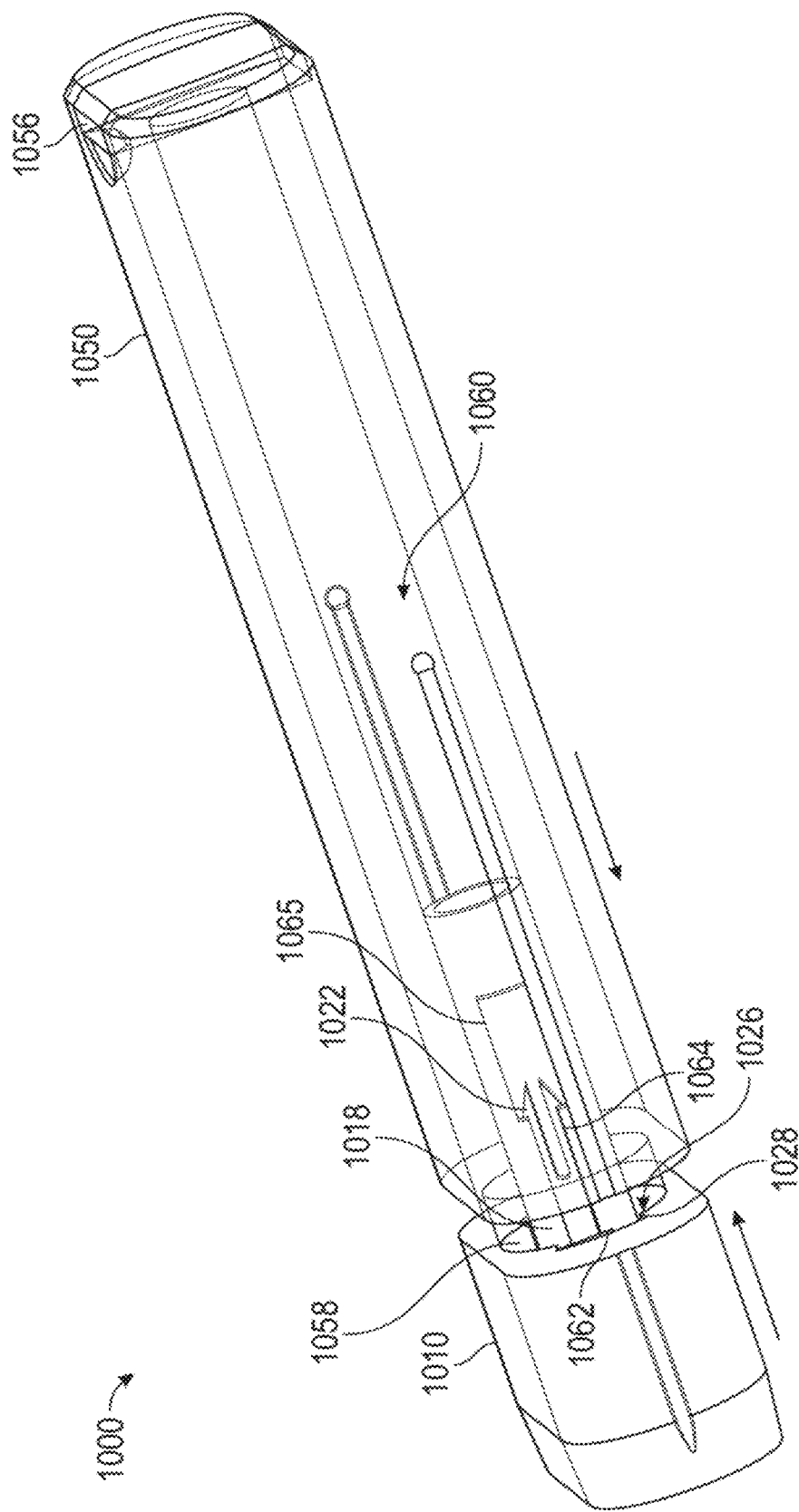

With reference to FIG. 11A, a fluid sample may be received within the cap 1050. For example, a swab or other sample carrier may be inserted into an opening of the cap 1050 opposite the cartridge body 1010, and the opening may then be sealed by the sample receiving area cap 1056 to contain the sample within the cap (e.g., within the plunger receiving well 1060 or other internal space within the cap 1050. When the fluid sample has been sealed within the cap 1050, the process of FIGS. 11A-11D may be used to mechanically couple the cartridge body 1010 to the cap 1050 and move the fluid sample into the cartridge body 1010.

As shown in FIG. 11A, the mechanical coupling of the cartridge body 1010 and the cap 1050 begins by inserting the plunger 1018 of the cartridge body 1010 into the plunger receiving well 1060 of the cap 1050. The sealing portion 1020 of the plunger 1018 can sealingly engage with the interior of the plunger receiving well 1060 to trap and begin compressing a volume of air within the plunger receiving well 1060. As the plunger 1018 slides into the plunger receiving well 1060, the snap-fit clips 1022 slide within the receiving channels 1064 until they pass into the widened sections 1065 of the receiving channels 1064, where they are longitudinally retained. Retention of the snap-fit clips 1022 within the receiving channels 1064 prevents removal of the cap 1050 from the cartridge body 1010, and further locks the cap 1050 rotationally with the plunger 1018, thereby allowing a user to rotate the plunger 1018 and plunger baseplate 1019 by rotating the cap 1050, which may be relatively large and easy to manipulate manually. The cap 1050 and cartridge body 1010 may slide together until the collar 1058 of the cap 1050 is partially within the receiving well 1026 of the cartridge body 1010 and the interlocking fins 1062 of the collar 1058 contact the stops 1030 (FIG. 10F) within the cutouts 1028.

Figure 11B:
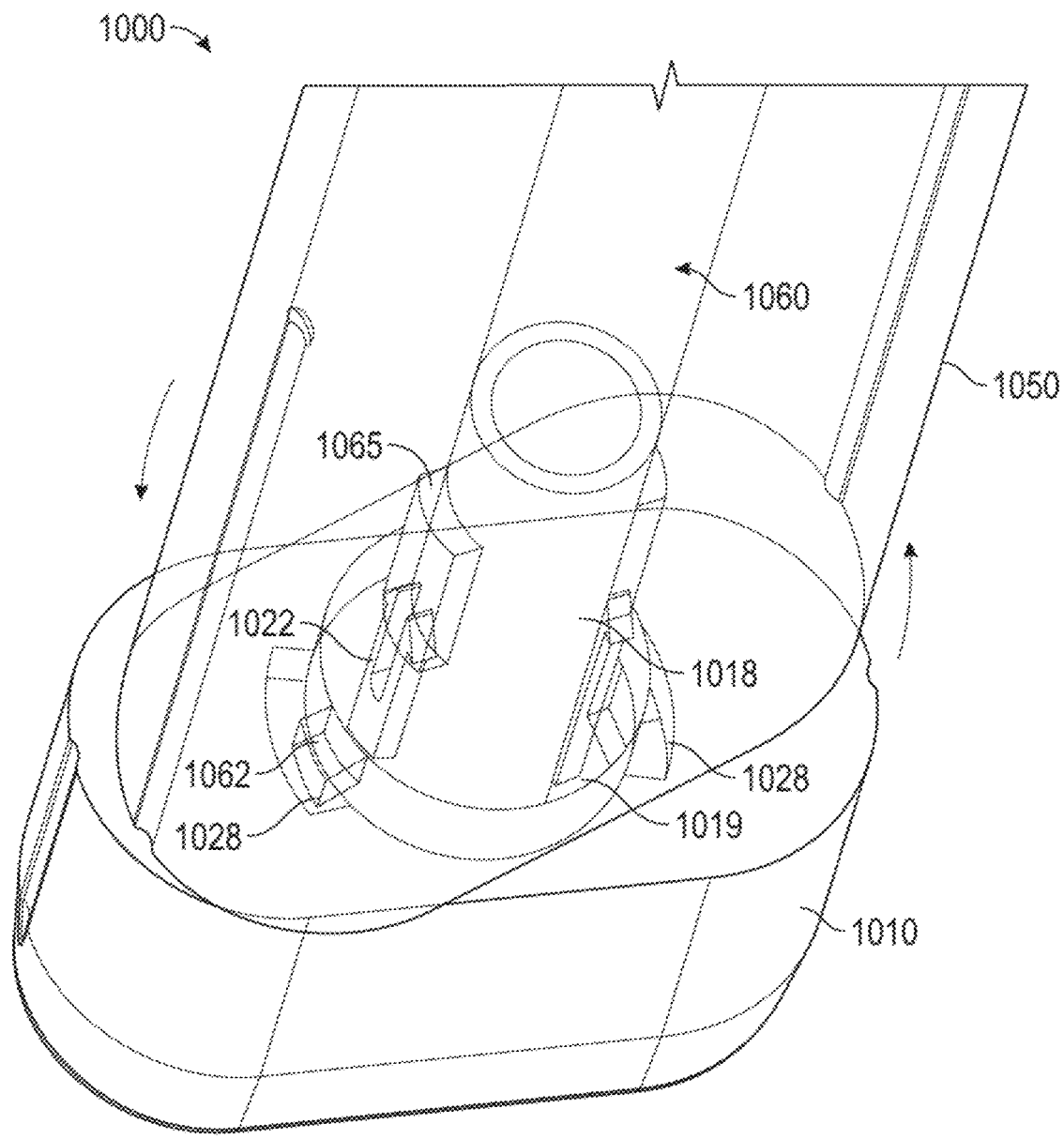

As shown in FIG. 11B, the cap 1050, plunger 1018, and plunger baseplate 1019 may then be rotated about the longitudinal axis. Because the snap-fit clips 1022 rotationally fix the plunger 1018 to the cap 1050, rotation of the plunger 1018 and plunger baseplate 1019 may be achieved by rotating the cap 1050. The cap 1050 may rotate until the interlocking fins 1062 are blocked by a lateral side of the cutouts 1028 of the receiving well 1026. In the example cartridge 1000, the cutouts 1028 and interlocking fins 1062 are sized to allow a total rotation of approximately 22.5° while the interlocking fins 1062 are within the cutouts 1028. However, other example cartridges may function with a different range of rotational motion, such as between approximately 5° and approximately 90°, between approximately 10° and approximately 45°, between approximately 15° and approximately 30°, between approximately 20° and approximately 25°, or any angle or subrange of angles therebetween. In some embodiments in which liquid constituents are contained in a blister pack within the cap 1050 and/or the plunger 1018, the rotation of components in FIG. 11B may cause the blister pack to be punctured so as to release the liquid constituents to mix with the sample.

Figure 11C:
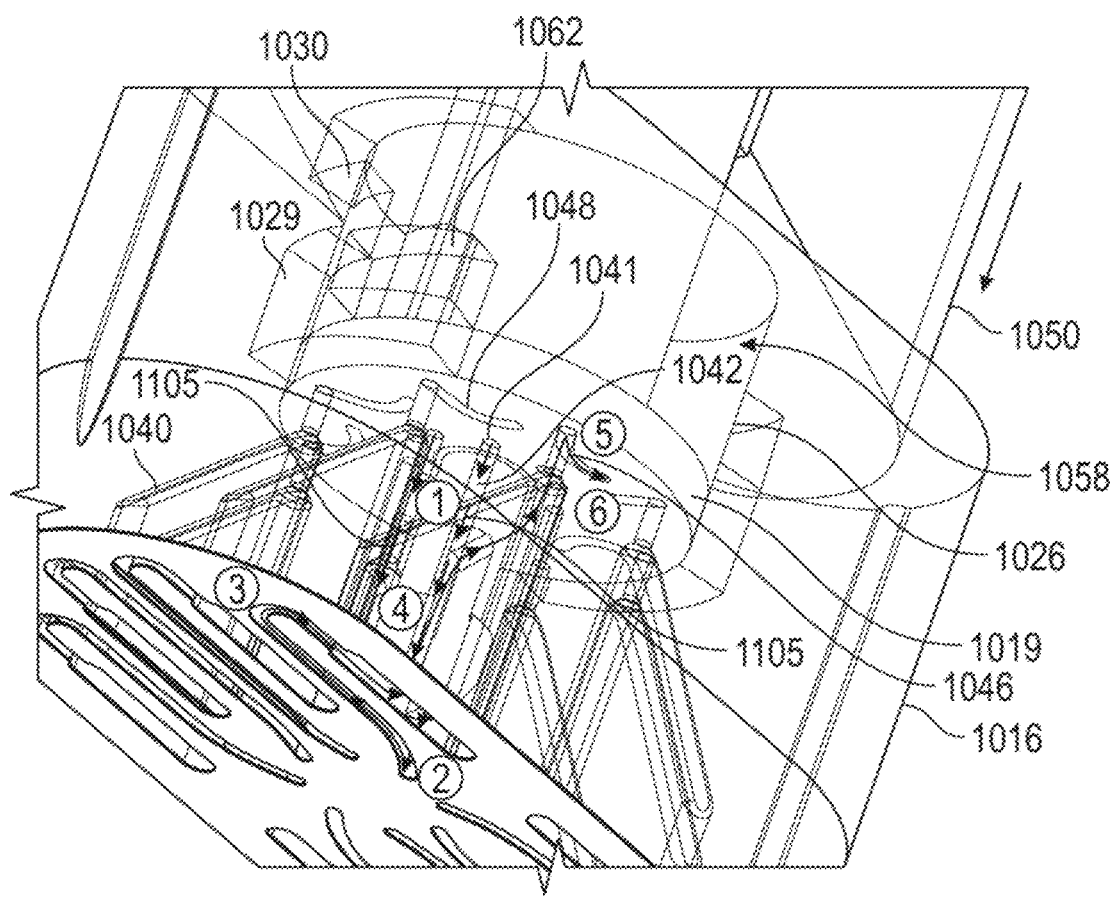

With reference to FIG. 11C, the cap 1050 may be moved downward along the longitudinal axis, such that the collar 1058 moves further into the receiving well 1026. Because the stops 1030 only extend along a portion of the cutouts 1028, the rotational motion described with reference to FIG. 11B moves the interlocking fins 1062 clear of the stops 1030 such that the interlocking fins 1062 can move to an interior portion 1029 of the cutouts 1028. As shown in FIG. 11C, the rotated position of the plunger baseplate 1019 substantially aligns the inlet channels 1042 and the outlet channels 1046 with the sample inlets 1041 and the sample outlets 1048, respectively. When the cap 1050 is pressed further onto the cartridge body 1010 to the position of FIG. 11C, the sample carrier and/or one or more internal structures within the cap 1050 may mechanically contact and rupture a seal on or within the plunger 1018 (e.g., the sacrificial seal 1024 of FIG. 10F), thereby allowing the trapped air compressed by the plunger 1018 to flow into the interior of the plunger and propel the fluid sample through the plunger baseplate 1019 and into the fluid paths of the cartridge body 1010. In some embodiments in which liquid constituents are contained in a blister pack within the cap 1050 and/or the plunger 1018, the longitudinal motion of components in FIG. 11C may cause the blister pack to be punctured so as to release the liquid constituents to mix with the sample.

The flow of the fluid sample through the fluid paths of the cartridge body 1010 will now be described with continued reference to FIG. 11C. FIG. 11C illustrates the flow of a portion of a fluid sample through a single example fluid path 1105 within the cartridge body 1010 with encircled numbers shown as labels for certain points along the fluid path. The encircled numbers are discussed below as example steps of a progression of a fluid sample as it travels through the flow path 1105. within the cartridge body 1010, with each step including a directional arrow showing the direction of fluid travel at that step.

At step (1), as the compressed air is allowed to flow into the plunger 1018, the fluid sample is forced through the sample inlet 1041 into the inlet channel 1042. The fluid sample travels along the inlet channel 1042 toward the lateral channel 1044.

At step (2), the fluid sample reaches the PCB 1014 boundary of the fluid path, and begins traveling parallel to the PCB 1014 within the lateral channel 1044. At step (3), the fluid sample continues through the curved lateral channel 1044 toward the test well 1040.

At step (4), the fluid sample enters the test well 1040. The test well 1040 may contain one or more reagents. Agitation caused by the turbulent flow of the fluid sample within the relatively larger space of the test well 1040 causes the reagent and the sample to be mixed. In some embodiments, the reagent and the fluid sample are mixed into a homogeneous solution in which the reagent is evenly distributed throughout the fluid sample. The depth, width, shape, and/or cross-sectional profile of the test well 1040 may be selected to facilitate mixing of the reagent and the fluid sample.

At step (5), any excess fluid sample is pushed from the test well 1040 into the outlet channel 1046 and enters the outer end of the J-shaped sample outlet 1048. As the excess fluid sample reaches the inner end the sample outlet 1048, it passes through a corresponding opening in the plunger baseplate 1019 at step (6) and is vented into the plunger 1018. In some embodiments, the interior volume of the plunger 1018 and/or the cap 1050 is separated from the interior volume that is fluidically connected to the sample inlet 1041, so as to create a directional flow of fluid sample along the fluid path 1105.

After the cap 1050 is pressed fully onto the cartridge body 1010 as shown in FIG. 11C, initiating the flow of the fluid sample through the fluid path within the cartridge body, the cartridge 1000 may reach a pressure equilibrium as the compressed air forces the fluid sample into the fluid path 1105, the fluid path 1105 is filled with the fluid sample, and a portion of the sample is vented back into the plunger 1018 and/or the cap 1050. The pressure equilibrium may be reached relatively quickly, for example, within 10 seconds, 5 seconds, 2 seconds, 1 second, or less.

Figure 11D:
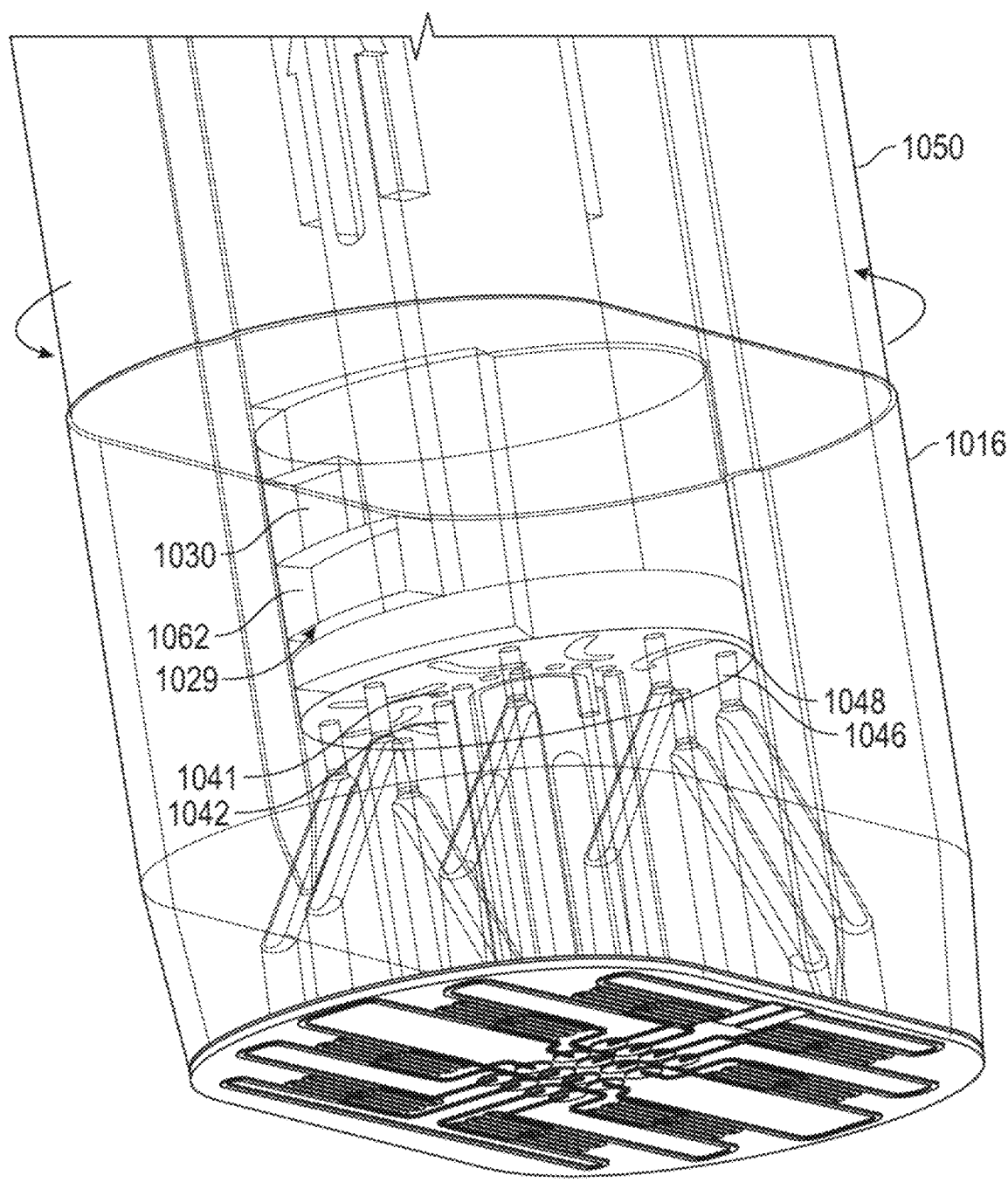

Referring now to FIG. 11D, when the fluid path 1105 is filled, the cap 1050, plunger 1018, and plunger baseplate 1019 may again be rotated relative to the cartridge body 1010. In the example process of FIGS. 11A-11D, the above components are rotated by the same angular displacement, but in the opposite direction, relative to the rotation of FIG. 11B. Thus, as shown in FIG. 11D, the plunger baseplate 1019 rotates relative to the fluid path 1105 such that the inlet channels 1042 and outlet channels 1046 are no longer aligned with the sample inlets 1041 and sample outlets 1048, thereby sealing the fluid path 1105 and retaining the fluid sample within the test wells 1040 for testing. This final rotation step additionally causes the interlocking fins 1062 of the cap 1050 to be retained under the stops 1030 within the interior portion 1029 of the receiving well cutouts 1028, completing and securing the mechanical coupling of the cartridge body 1010 and cap 1050. Moreover, the final rotation step substantially aligns the exterior profiles of the cartridge body 1010 and the cap 1050 such that the assembled cartridge 1000 can be inserted into a reader device to perform one or more tests on the fluid sample contained therein.

FIGS. 12A-12I illustrate a further embodiment of a cartridge 1200 configured for detection of a target. As described herein, the target may be a viral target, bacterial target, antigen target, parasite target, microRNA target, or agricultural analyte. Some embodiments of the cartridge 1200 can be configured for testing a single target, while some embodiments of the cartridge can be configured for testing for multiple targets. The cartridge 1200 includes a cartridge body 1202 and a swab assembly 1220 configured to be mechanically coupled to the cartridge body 1202 at a swab assembly insertion point 1208.

The cartridge body 1202 includes a thin film testing assembly 1204 and an ergonomic frame 1206 configured to be grasped by a user. The thin film testing assembly 1204 generally includes a plurality of test wells 1258, pinch valves 1214 for isolating fluid within the test wells 1258, a gas permeable filter 1212 such as a membrane or the like, and an electrode interface 1210 for electrically connecting electrodes at the test wells to circuitry of a reader device. The cartridge further includes a fluidic piston 1218 and a transition point 1216 for introducing a fluid sample from the swab assembly 1220 into the thin film testing assembly 1204. The features of the thin film testing assembly 1204 are discussed in greater detail with reference to FIGS. 12H and 12I.

Referring now to FIGS. 12C-12G, the swab assembly 1220 includes a tube 1222, a slider 1224, and a cap 1234 configured to fit together to form a substantially sealed swab assembly 1220. The tube 1222 includes a tube channel 1226 sized and shaped to receive a shaft 1236 of the cap 1234. The tube channel 1226 may be sealed, such as with a foil seal or the like, to contain one or more liquid reagents, buffers, etc., during shipping and/or prior to use of the swab assembly 1220. The tube channel 1226 may have an hourglass profile, a dual lobe profile, or other shape configured to facilitate mixing of fluids therein. In some embodiments, the tube channel 1226 may further include interior threading or other protruding features further configured to facilitate mixing of fluids with in the tube channel 1226. The slider 1224 comprises a hollow structure configured to fit around an engagement end 1223 of the tube 1222. The tube 1222 further includes one or more snap-fit clips 1232 configured to interlock with first and second snap-fit openings 1228 and 1230 of the slider 1224. As shown in FIG. 12A, the cartridge body 1202 includes an overhand that keeps the tube 1222 centered in a width of the cartridge body 1202.

Figure 12A:
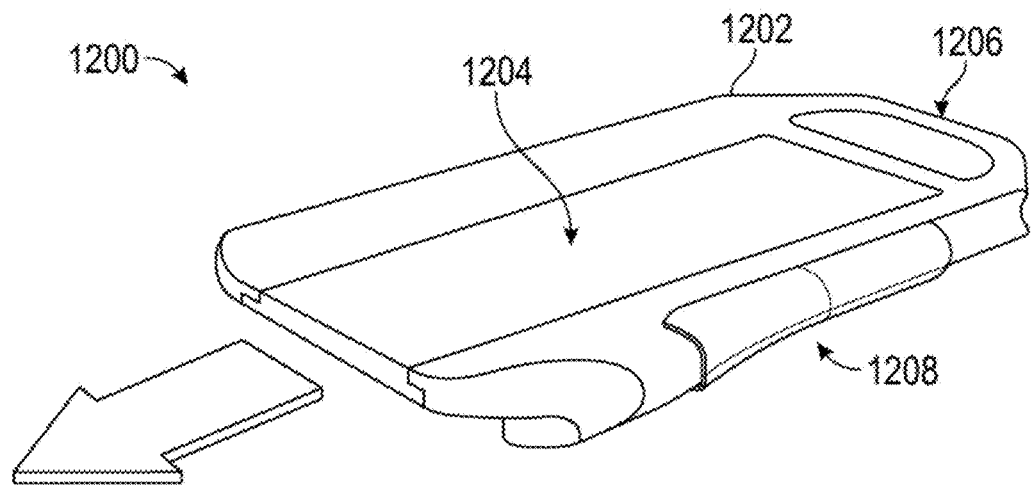
Figure 12B:
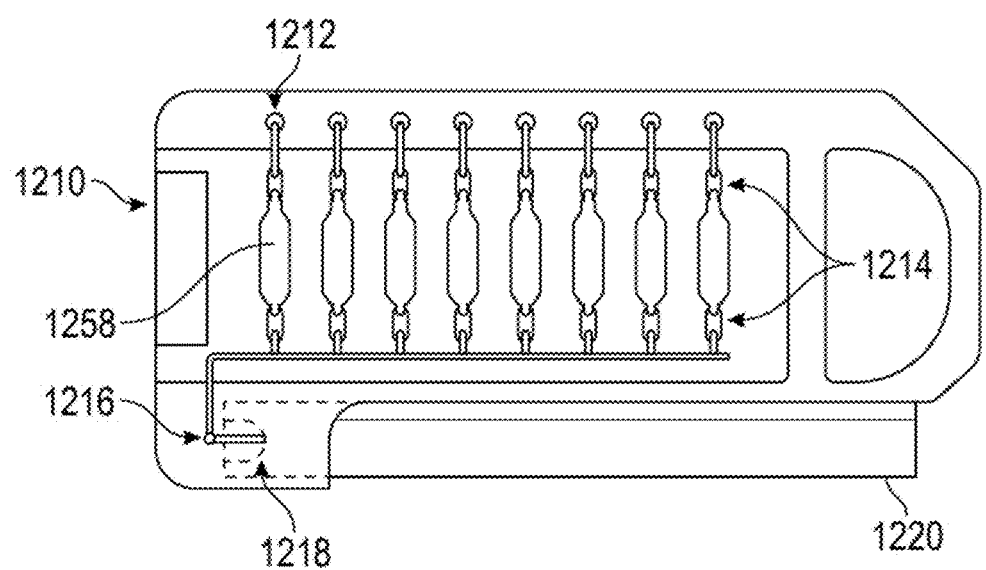
Figure 12D:
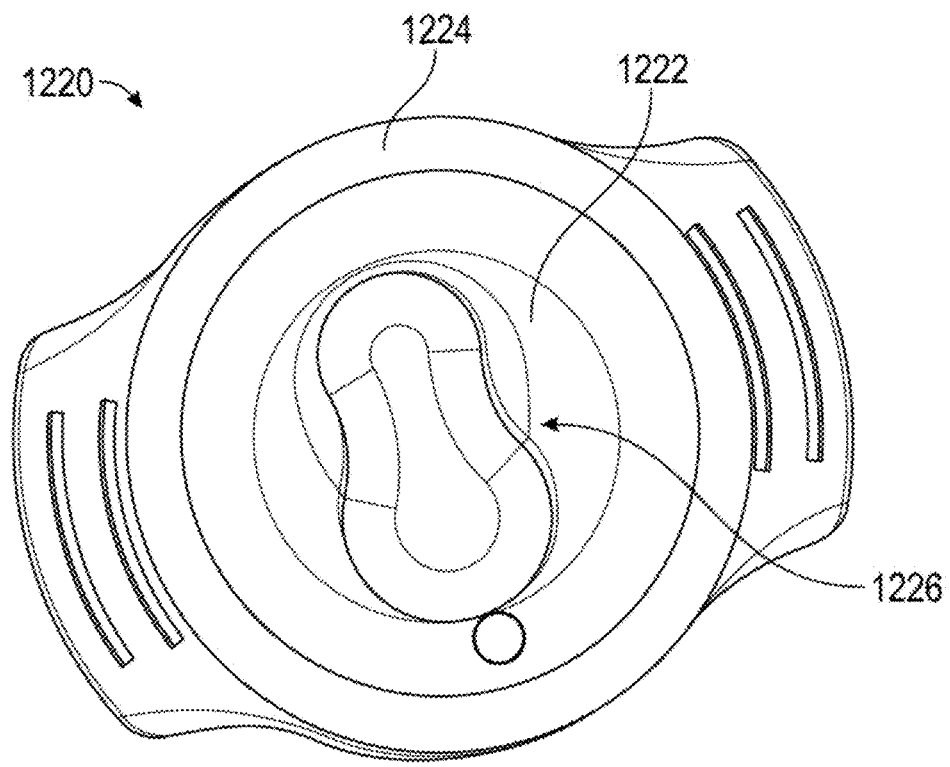
Figure 12E:
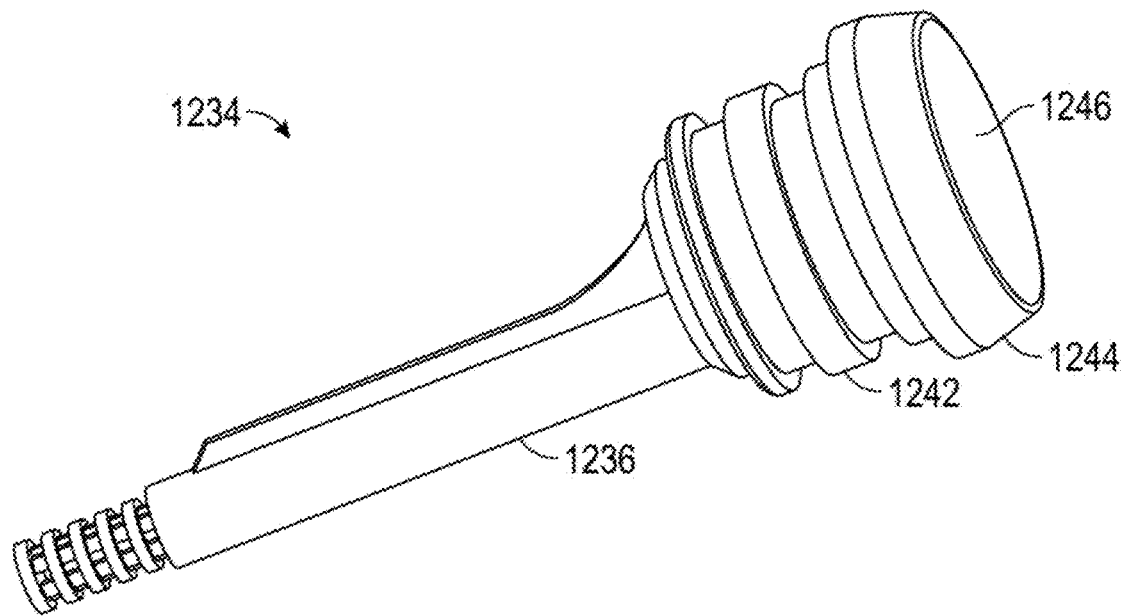
Figure 12F:
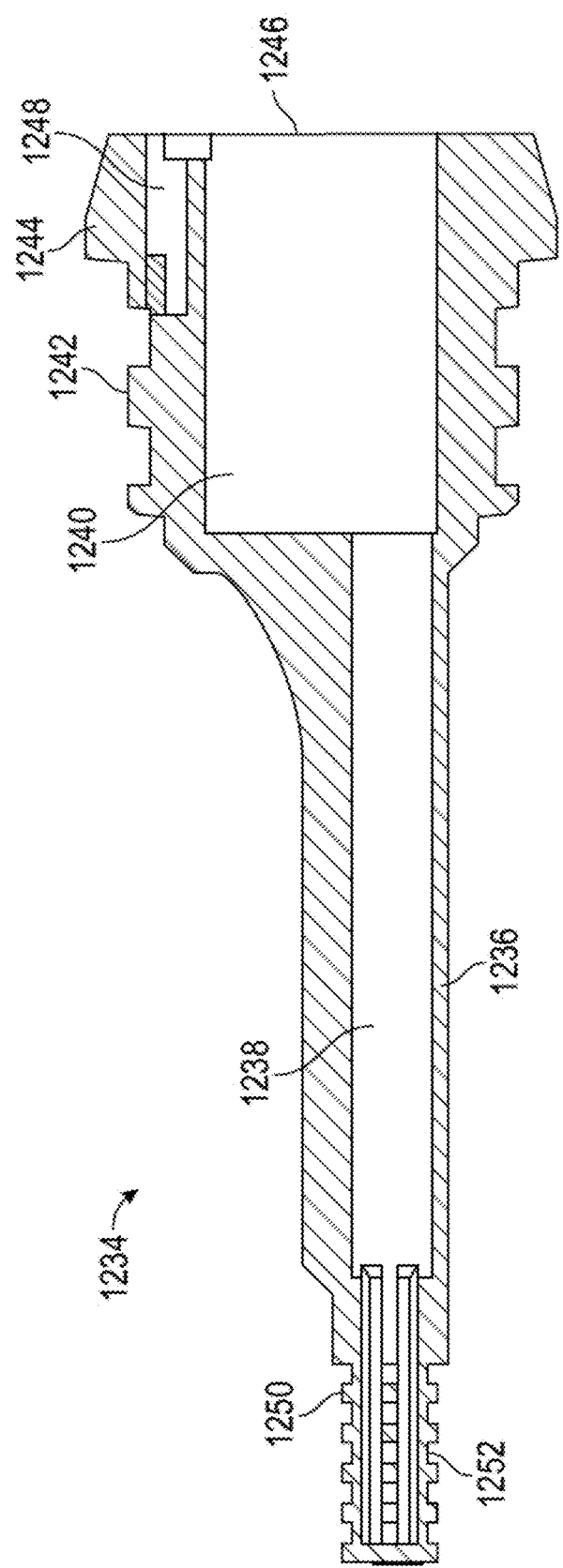

FIGS. 12E and 12F illustrate the cap 1234. FIG. 12E is a perspective view of the cap. FIG. 12F is a cross-sectional view of the cap illustrating internal components thereof. The cap 1234 comprises a hollow shaft 1236 surrounding a cap channel 1238, and a hollow upper section 1244 surrounding a metered volume 1240. The upper section 1244 may further include a sealing portion 1242 comprising a resilient material (e.g., rubber, a resilient plastic, or other elastomeric material) sized and shaped to sealingly engage the interior of the slider 1224. A foil seal 1246 may seal one or more liquid and/or dried reagents within the cap 1234. A vent 1248 may be fluidically connected to the metered volume 1240 to allow any gas trapped within the cap 1234 to be vented. The shaft 1236 terminates at a cap inlet 1250 fluidically connected to the cap channel 1238, which may include one or more sections of a filter 1252 configured to allow fluid flow into the cap channel 1238. In some embodiments, an additional seal may be provided over the cap inlet 1250 to seal any liquid and/or dried reagents within the cap 1234 prior to use.

Figure 12G:
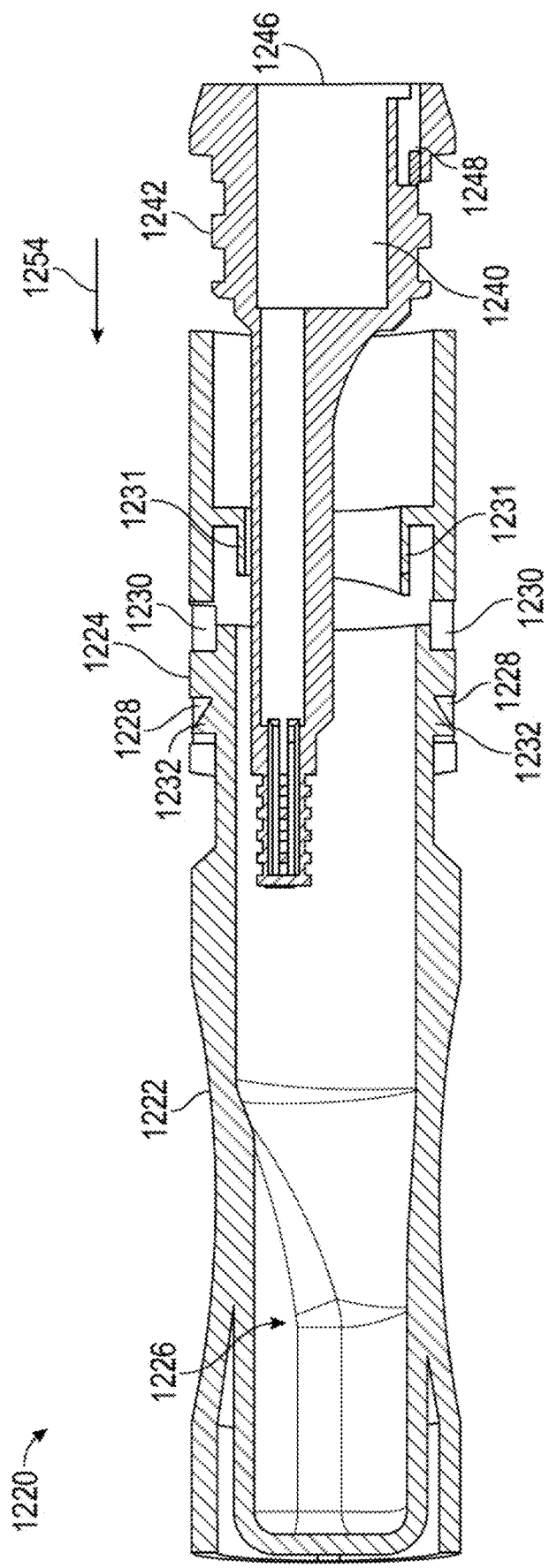

Referring jointly to FIGS. 12C-12G, and particularly with reference to FIG. 12G, an example process of introducing a sample to the swab assembly 1220 will now be described. Prior to introduction of the sample, the cap 1234 is separate from the tube 1222 and the slider 1224. The tube 1222 includes a liquid comprising one or more liquid reagents, buffers, or the like, sealed within the tube 1222 by a seal at the engagement end 1223 of the tube 1222. The cap 1234 includes one or more additional liquid reagents, buffers, or the like, sealed within the cap 1234 by the foil seal 1246. In the initial configuration, the snap-fit clips 1232 are engaged in first snap-fit openings 1228.

A sample (e.g., a nasal swab or other swab-collected sample) may be received on a swab. Prior to inserting the swab into the swab assembly 1220, the slider 1224 is moved along a first direction 1254 relative to the tube 1222 such that the snap-fit clips 1232 of the tube 1222 engage with the second snap-fit openings 1230. This motion may cause an internal structure 1231 of the slider 1224 to break the foil seal at the opening of the tube to expose the liquid reagents or buffers contained within the tube channel 1226.

When the tube channel 1226 is exposed, the swab may be introduced into the tube channel 1226 such that the sample on the swab mixes with the liquid reagents within the tube channel 1226. The interior profile and/or other mixing features of the tube channel 1226 may facilitate mixing of the sample with the liquid reagents to form a test fluid. In some embodiments, the swab may be broken off from a handle such that the portion of the swab containing the sample remains within the tube channel 1226.

After the sample has been introduced to the tube channel 1226 to form the test fluid, the cap 1234 may be mechanically coupled to the tube 1222 and slider 1224 to complete the swab assembly 1220. If a seal is provided around the cap inlet 1250, the seal may be removed. The shaft 1236 of the cap is inserted through the slider 1224, and the cap 1234 is pushed into the slider 1224 and the tube channel 1222 such that the sealing portion 1242 sealingly engages with the interior of the slider 1242. As the cap 1234 continues to move along the direction 1254, air and fluid are compressed within the tube channel 1222 to drive the mixed test fluid through the cap inlet 1250 and the cap channel 1238 into the metered volume 1240. Any gas, such as air, present within the metered volume 1240 may be vented externally through the vent 1248. The filter 1252 at the cap inlet 1250 prevents solids, such as solids within the swab sample or pieces of the swab itself, from entering the cap 1234. The location of the cap inlet 1250 at an end of the tube channel 1226 distal from the metered volume 1240 may advantageously cause the inlet 1250 to receive an optimal portion of the test fluid in the event that the test fluid has not quite achieved a homogeneous mixture. When the cap 1234 has been sealingly inserted into the tube 1222 and slider 1224, the swab assembly 1220 is fully assembled, and any liquid therein is retained within the swab assembly 1220 by the foil seal 1246 of the cap 1234. The swab assembly 1220 may then be placed into the swab assembly insertion point 1208 of the cartridge 1200 to introduce the test fluid to the thin film testing assembly 1204.

Figure 12H:
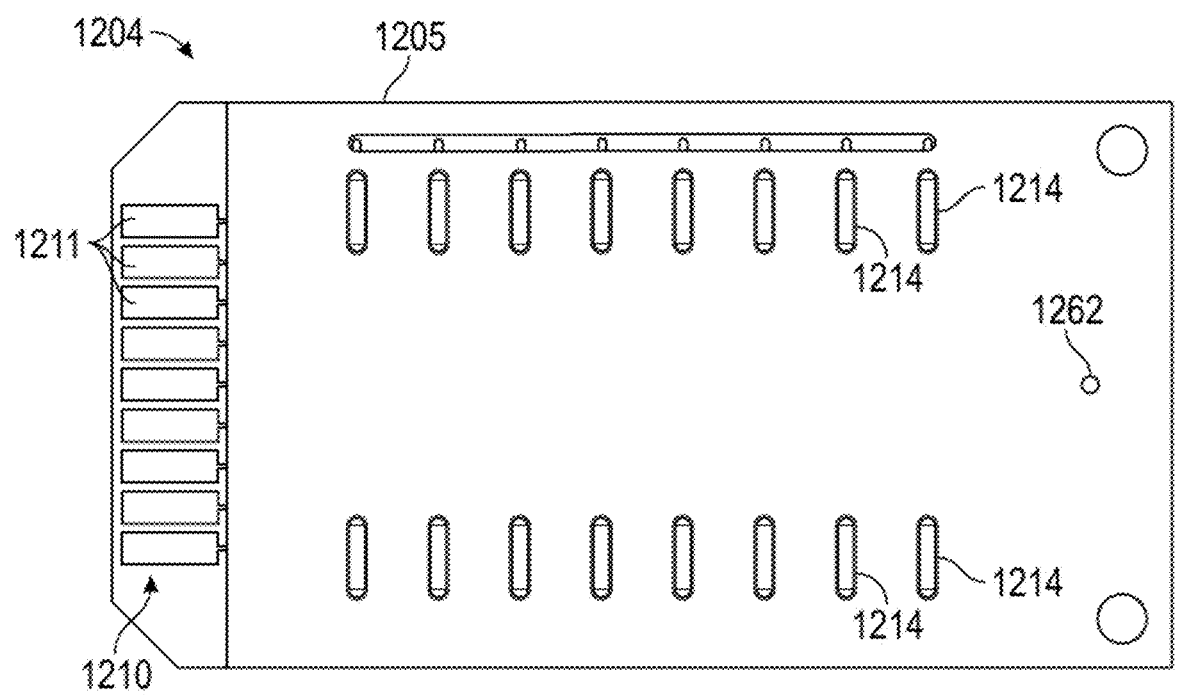
Figure 12I:
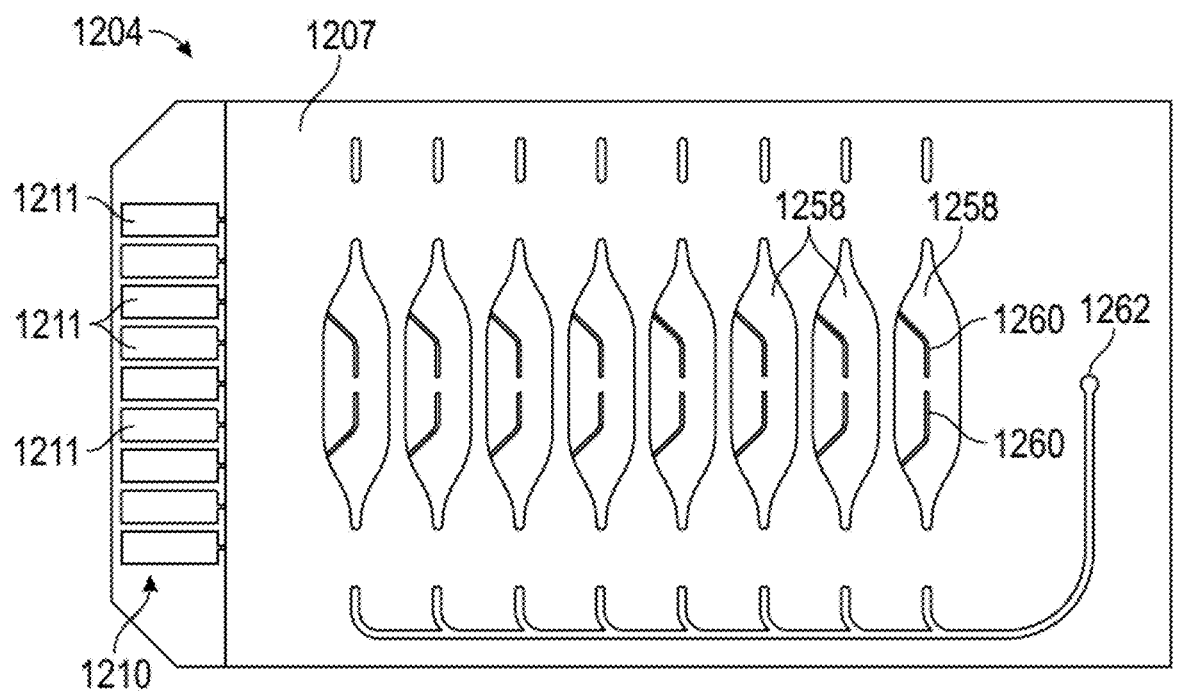
Figure 13A:
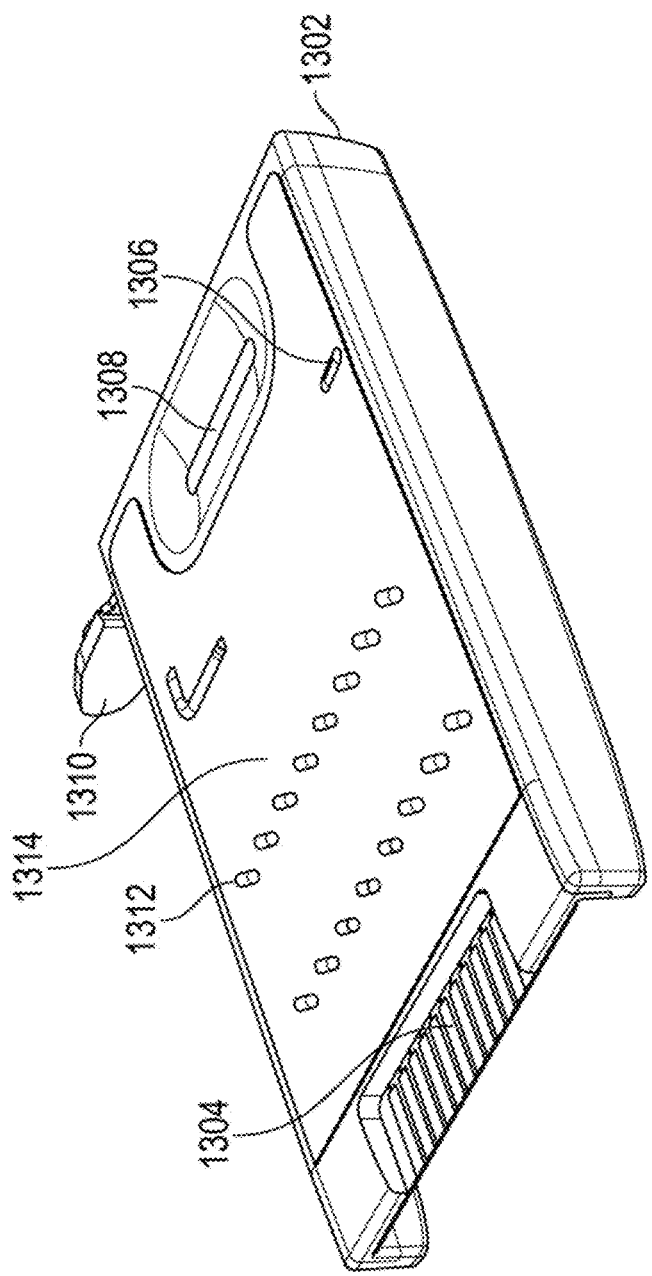
FIGS. 13A-13E depict an example of another type or format of cartridge configured to detect a target that can be used in conjunction with a handheld system disclosed herein.
Figure 13B:
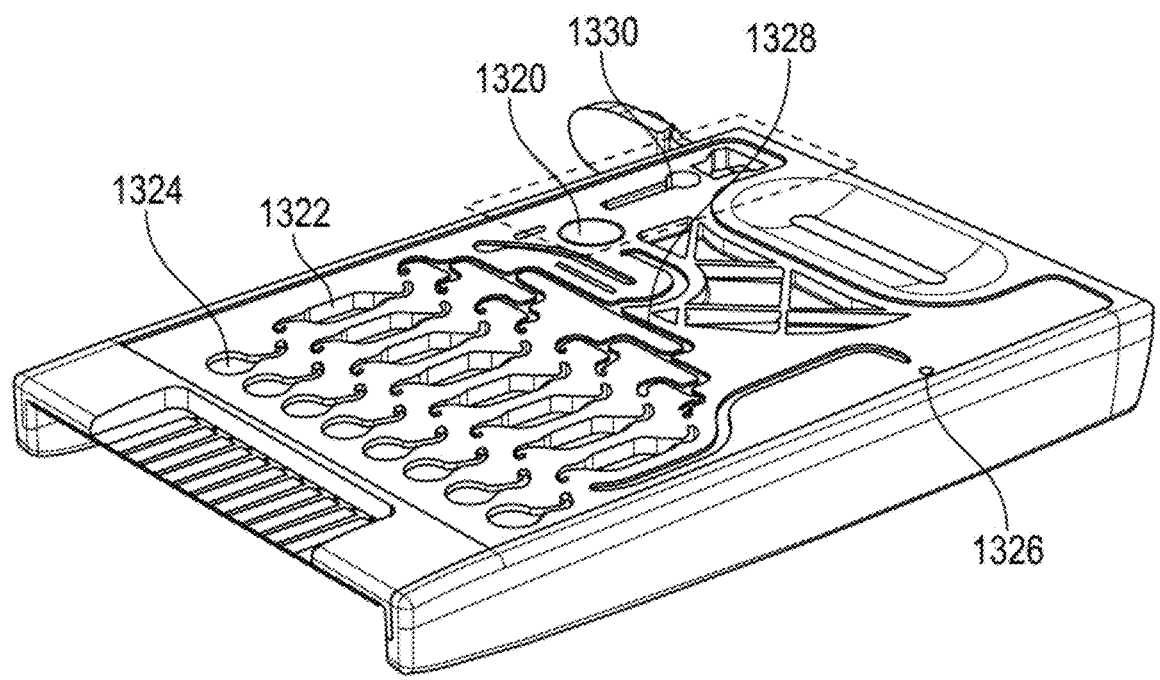
Figure 13C:
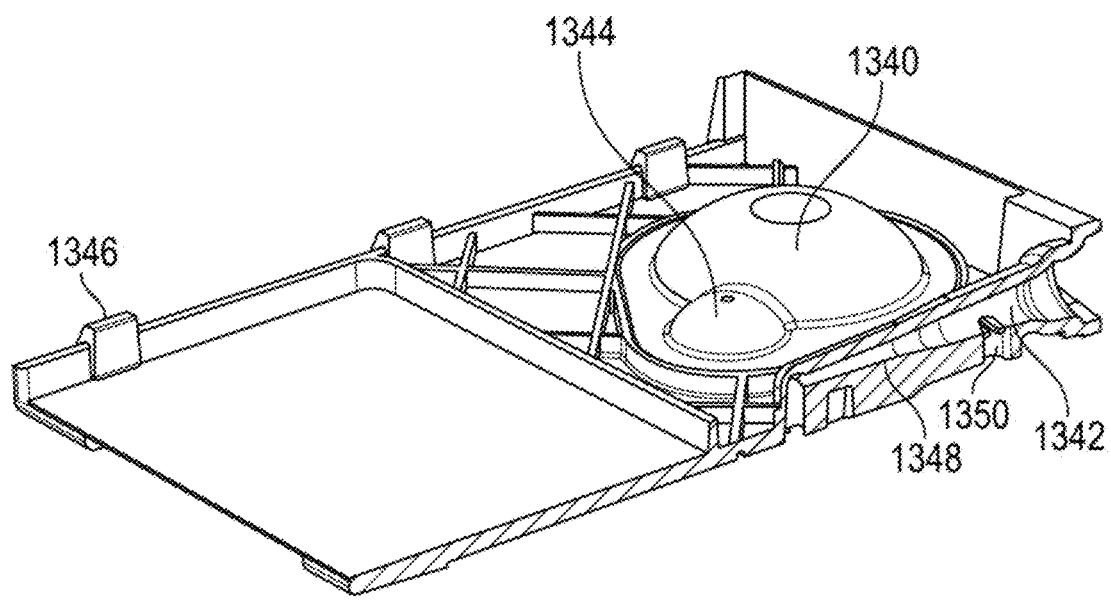
Figure 13D:
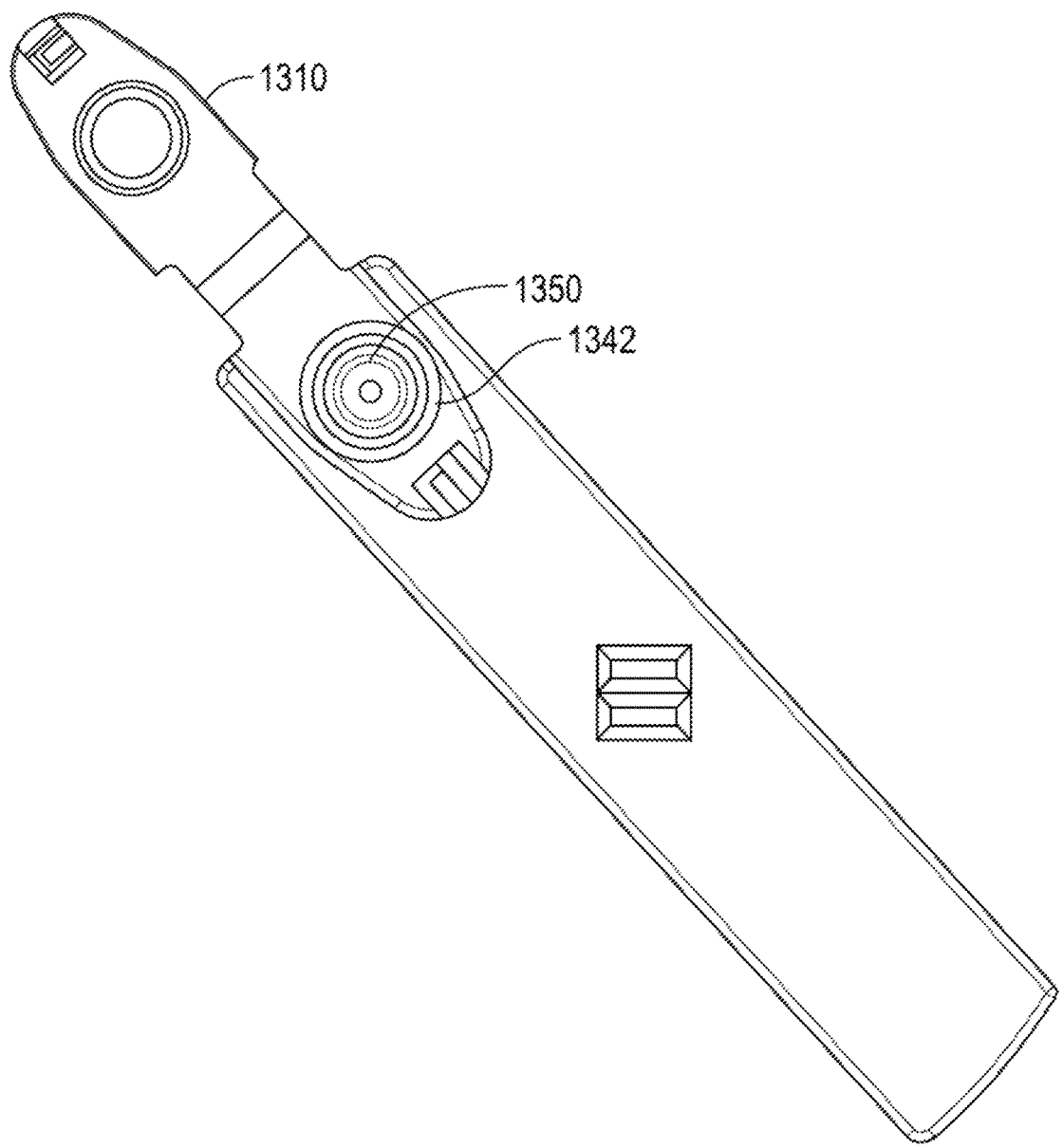
Figure 13E:
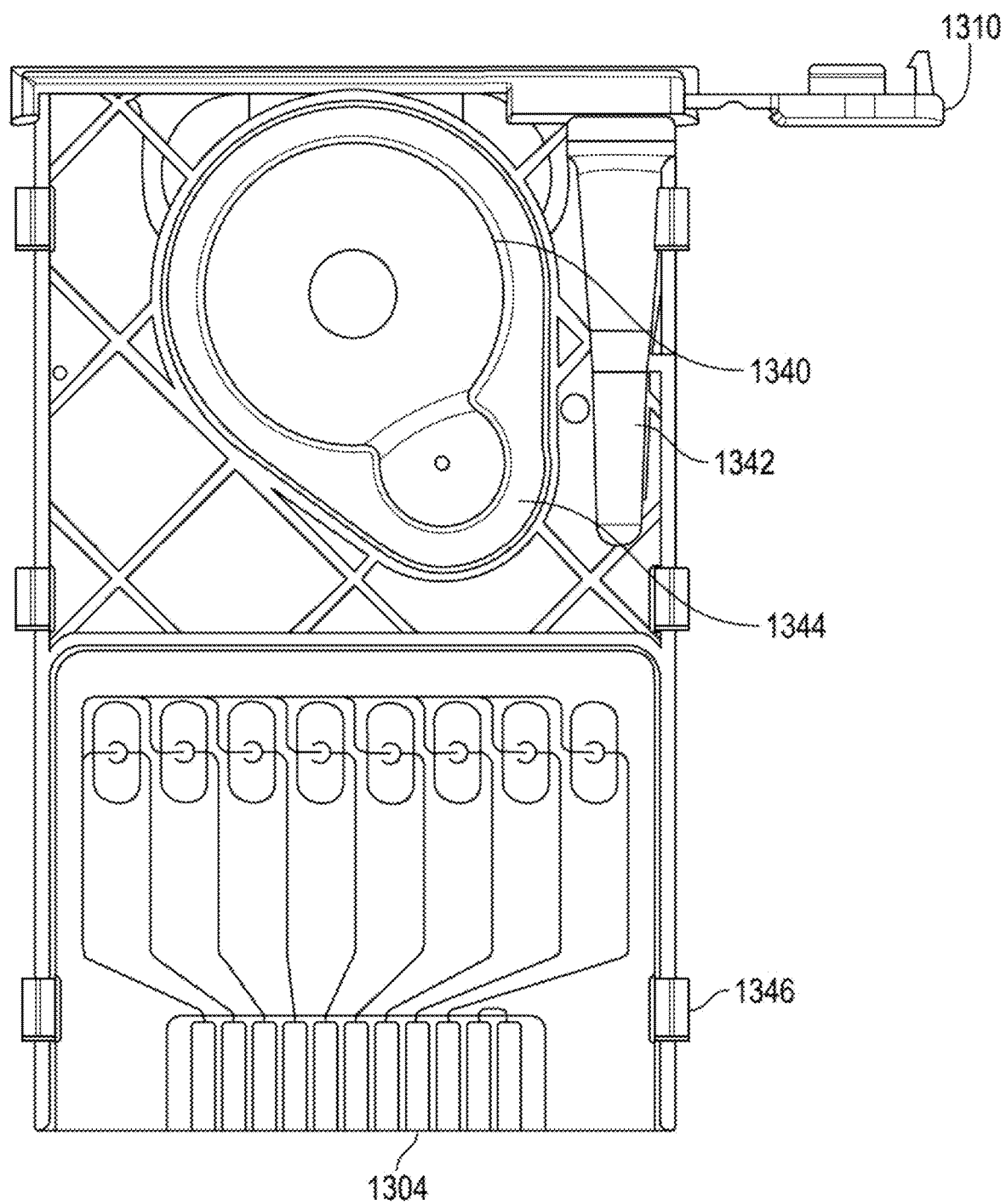

Referring now to FIGS. 12B, 12H, and 12I, the thin film testing assembly 1204 includes a substrate 1207 surrounding a plurality of test wells 1258. One boundary of the test wells 1258 is formed by a cover film 1205 including a plurality of pinch valves 1214 which form a portion of a fluid flow path into the thin film testing assembly 1204. A pair of electrodes 1260, which may be formed consistent with any of the electrodes described elsewhere herein, are provided within each test well 1258 and electrically connected to electrode connection pads 1211 of the electrode interface 1210 for connection to a reader device.

When the swab assembly 1220 is inserted into the swab assembly insertion point 1208 of the cartridge 1200, the fluid within the metered volume 1240 of the swab assembly 1220 flows through the transition point 1216 and along a fluid path within the thin film testing assembly 1204 to fill the test wells 1258. Any gas such as air within the thin film testing assembly 1204 may be displaced from the test wells 1258 and vented at a vent 1262 and/or at the gas permeable filter 1212.

The cartridge 1200 may then be inserted into a reader device sized and shaped to receive the cartridge 1200. As the cartridge 1200 is inserted into the reader device (in a direction of the arrow in FIG. 12A), electrical contacts within the reader device come into contact with the electrode connection pads 1211 of the cartridge 1200. In addition, the opening within the reader device for receiving the cartridge 1200 has a width selected such that an interior surface of the reader device compresses and/or crushes the pinch valves 1214, preventing fluid flow therethrough after the cartridge 1200 has been inserted into the reader device. In some embodiments, the pinch valves 1214 may comprise a thermoformed plastic or other material selected such that the pinch valves 1214 can be compressed and closed off without breaking and allowing the test fluid to escape. When the pinch valves 1214 are compressed and/or crushed, the test fluid within each test well 1258 is fluidically isolated within the test well 1258 for testing. Heating and testing of the test fluids in the test wells 1258 may then proceed as described above with reference to the cartridges 200, 1000. In some embodiments, the test wells 1258 may be pre-loaded with one or more primers (e.g., spot-dried, powdered, or other non-liquid primers) or other reagents corresponding to the tests to be performed and/or target agents to be detected in each test well 1258. Some or all of the test wells 1258 may include the same or different primers as the primers present in the other test wells 1258, depending on the individual test to be performed and/or target agents to be detected in each test well 1258.

FIGS. 13A-13E depict an example of another type or format of cartridge 1300 configured to detect a target, such as a nucleic acid e.g., a desired DNA or RNA sequence, which can be used in conjunction with one or more of the handheld systems disclosed herein. In some embodiments, the target may be a viral target, bacterial target, antigen target, parasite target, microRNA target, or agricultural analyte. Preferably, such targets are selected viral, bacterial, parasite, microRNA, or agricultural DNA or RNA sequences e.g., sequences complementary to selected primers designed to identify the presence or absence of such targets. Some embodiments of the cartridge 1300 can be configured for testing for the presence or absence of a single target, while some embodiments of the cartridge 1300 can be configured for testing for multiple targets, optionally simultaneously or within a short time after the first identified result. In some embodiments, the cartridge 1300 may be configured to test for enzymes (for example, in the evaluating and/or analyzing for enzyme replacement therapy). In some embodiments, the cartridge 1300 may be configured to test for environmental contaminants such as pesticide residues (e.g., glyphosphate, and so forth), heavy metals, benzene residues, and so forth. In some embodiments, the cartridge 1300 may be configured to test for or identify pathogens, genomic materials, proteins, and/or other small molecules or biomarkers. In some embodiments, the cartridge 1300 may be configured to test for and/or identify elevated prostate-specific antigen (PSA) levels, elevated cells counts, low cell counts, tumor cells, and so forth, for use in oncology applications. In some embodiments, the cartridge 1300 may be configured to identify and/or test for microRNA or used to test for infections, diseases, and so forth often of concern with respect to food safety and/or plasma and/or blood screenings. In some embodiments, the cartridge 1300 may be further configured to identify and/or test for rare infectious diseases, tick and/or mosquito borne (or other insect, plant, and/or animal vector borne) diseases. In some embodiments, the cartridge 1300 may be configured to test for and/or identify norovirus and/or rotavirus, for example in water quality applications. In some embodiments, the cartridge 1300 is configured to test for anything any of the other cartridges described herein test for, and vice versa. The cartridge 1300 includes, among other components, a cartridge body 1302, a cover 1314, electrodes 1304, and a cap 1310. These components will be described in further detail below.

Referring now to FIGS. 13A-13E, the cartridge body 1302 may be thermoformed from a polyethylene or similar plastic material. The cartridge body 1302 may house various components and/or features of the cartridge 1300. For example, the cartridge body 1302 may house at least a portion of the electrodes 1304, a swab receptacle 1342, a sample mixing and microfiltration region 1330 (described further below), a reagent stored in a reagent blister 1340, and an integrated reagent blister rupture feature 1344, a distribution tree 1328 for a sample/reagent mixture from the sample mixing and microfiltration region 1330, an exhaust port 1326 to vent gases, a degassing gas-permeable membrane 1320, and a plurality of reaction wells 1322 configured to allow the electrodes 1304 to generate signals based on the sample/reagent mixture. The cartridge body 1302 also includes a thumb detent configured to be grasped by a user to facilitate removal of the cartridge 1300 from the analyzer, described in further detail below. The cartridge body 1302 also, optionally includes an isolation cap 1310 or a locking isolation cap 1310 configured to isolate, close, or protect the swab receptacle 1342 from external variables. The cover 1314 of the cartridge body 1302 may be thermoformed from a plastic or similar material and includes an exhaust port crush valve 1306 and well isolations crush valves 1312.

The well isolations crush valves 1312 may isolate fluid within the plurality of reaction wells 1322. In some embodiments, the reaction wells 1322 may function similarly to the test wells 1258 described above. The electrodes 1304 may electrically connect electrodes at the reaction wells 1322 to circuitry of a reader device described further below. The electrodes 1304 may function similarly to the electrode interface 1210 described above.

In some embodiments, the swab receptacle 1342 includes a tapering, tubular portion 1348, a scraper portion 1350, dispensing portion 1352, and the isolation cap 1310 or the locking isolation cap 1310. The isolation cap 1310 or the locking isolation cap 1310 and the swab receptacle 1342 are configured to fit together to form a sealed or substantially sealed swab assembly. The tapering, tubular portion 1348 includes a tapering tube channel sized and shaped to receive a swab including mucus or another sample and to be sealed or substantially sealed by the isolation cap 1310 or locking isolation cap 1310. The reagent blister 1340 may contain one or more reagents (for example, a liquid reagent, a buffer, etc.) during shipping and handling before the cartridge 1300 is inserted into the corresponding analyzer. In some embodiments, the reagent blister 1340 includes only reagents in a liquid form. In some embodiments, the reagent blister may comprise a sealed compartment, for example sealed with a foil seal or the like, similar to the sealed channel 1226 described above. The sample mixing and macrofiltration region 1330 may be configured and operate to facilitate mixing of fluids and so forth therein (for example, the sample with the reagent). In some embodiments, the tapering, tubular portion 1348 may further include the scraper 1350 configured to facilitate acquisition of the sample from the swab inserted into the swab receptacle 1342. Further details are provided below. The cartridge body 1302 includes snap-fit clips 1346 that may lock and/or engage with snap-fit openings to interlock and hold the cartridge body 1302 together, similar to the snap-fit clips 1232 and snap-fit openings 1228 described above.

The cartridge 1300 may be a disposable cartridge that is fully integrated, enables detection of one or more pathogens, and includes no moving parts, improving reliability of the cartridge 1300. In many instances, the cartridge 1300 operates similarly to the cartridge 1200 described above.

The cartridge 1300 may be used in conjunction with an analyzer, similar to the analyzer or reader device (for example, reader device 110, 600, or 910) described above with reference to the cartridges described above (for example, cartridge 120, 200, 1000, and 1200). In some embodiments, the analyzer (also referred to herein as the "reader device") may be handheld and battery operated and enable wireless communication with an application operating, for example, on a user's mobile phone or other mobile device. In some embodiments, the application may provide the operator or patient with a view of the results from the analysis of the cartridge as well as an option for the patient to input particular symptoms being suffered. In some embodiments, the application may communicate with a cloud storage system (or similar storage) to store data from the application that is received from or via the analyzer. In some embodiments, the analyzer, application, and cloud storage may enable secure communications and may aggregate information from various cartridge samples to enable treatment decisions (for example, identify that a sample being tested with a cartridge indicates a particular sickness, etc., based on a comparison of the analysis results from the analyzer with results from a historical database of analyses and corresponding sickness, etc., determinations. For example, if the cartridge analyzed by the analyzer indicates influenza, as compared to similar results in the cloud-based historical database, the application may identify appropriate treatments or therapies for influenza and present them to the operator of the application (e.g., to the patient, physician, or health care practitioner, etc.). In some embodiments, the data stored in the cloud may be analyzed in real time to identify outbreaks of diseases, and so forth. Additionally, such information may be used to update manufacturers of vaccines and medications in response to the outbreaks, etc., to ensure sufficient stockpiles of vaccines and/or medications are available.

Figure 14A:
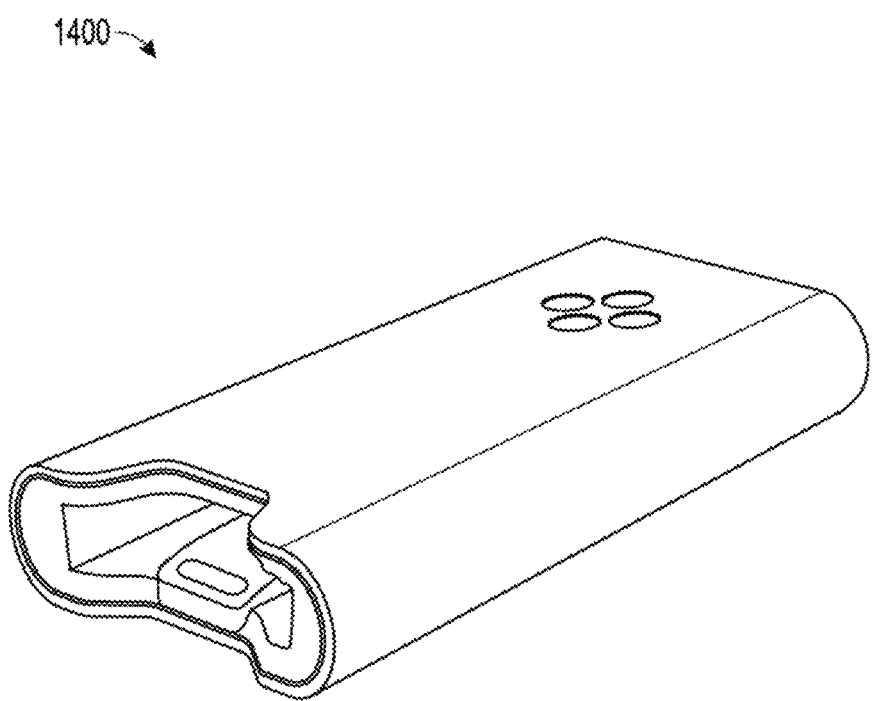
FIGS. 14A and 14B depict an example of another handheld system disclosed herein.
Figure 14B:
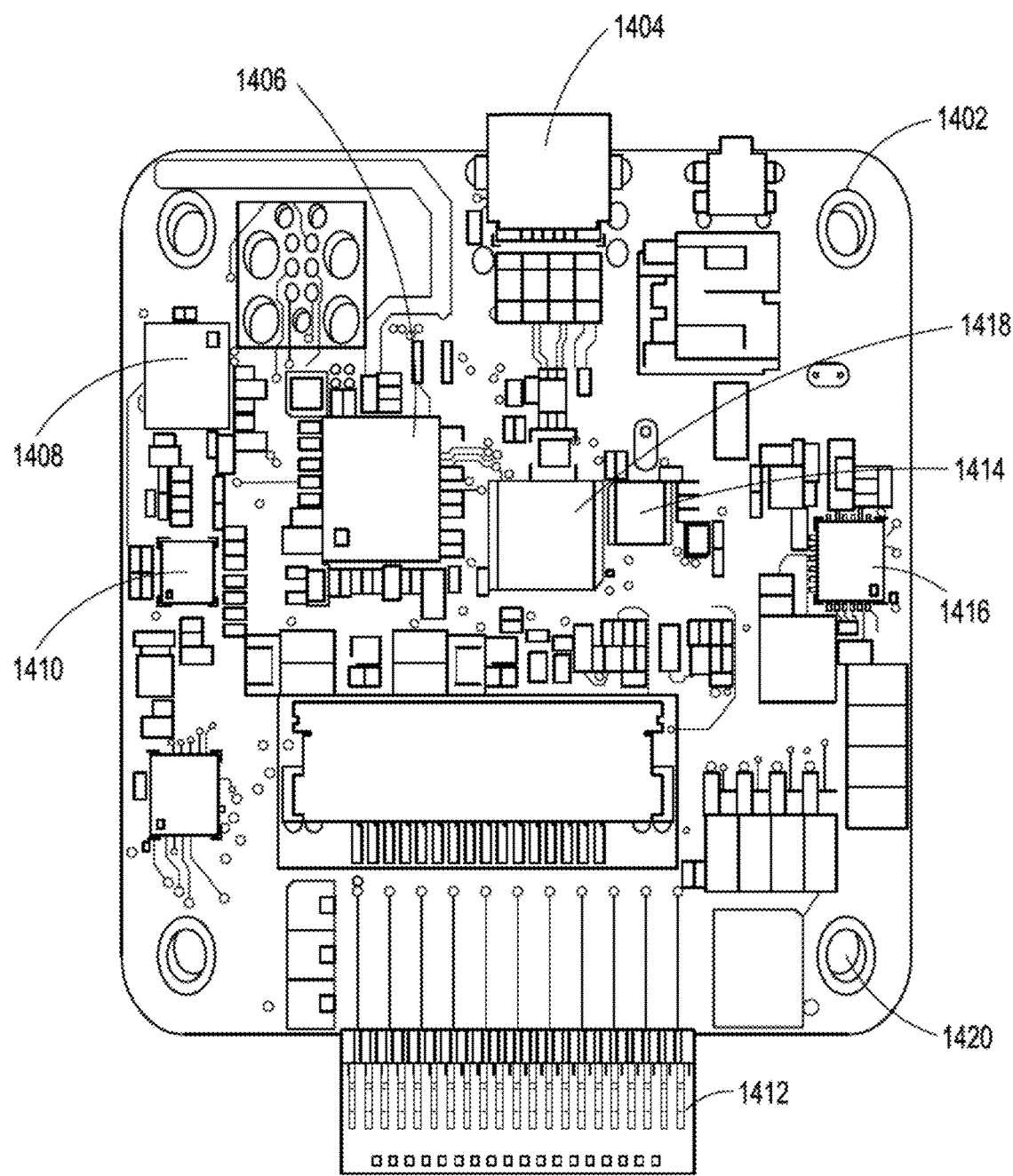

FIGS. 14A and 14B depict an example of the other handheld analyzer system 1400 disclosed herein. The analyzer 1400 includes the features described above of other analyzers, including a slot for insertion of the cartridge, for example the cartridge 1300. In some embodiments, the analyzer 1400 comprises a printed circuit board (PCB) 1402 on which various electrical components are disposed and electrically connected. The PCB 1402 includes a communication or charging port, such as a USB (or similar) port 1404. The PCB 1402 further includes a microprocessor 1406 and a digital signal processor (DSP) 1408. The PCB 1402 further comprises an analog sub-section 1410 and cartridge mating connectors 1412 to electronically couple to the cartridge 1300. The PCB 1402 further comprises a cryptographic processor 1414, a battery controller 1416, and storage 1418. The PCB 1402 may also include one or more mounting holes or devices 1420.

Operation of the cartridge 1300 with the analyzer 1400 is now described.

Before operating the cartridge and the analyzer 1400, the application may be used to select a particular cartridge 1300 that will be used with the analyzer 1400. In some embodiments, the selection may comprise indicating one or more parameters associated with the particular cartridge 1300 to the analyzer 1400. A swab may be used to collect a fluid sample (for example, a nasal fluid or sputum sample). The swab with the fluid sample from the patient may be pressed into the swab receptacle 1342 until the swab stops moving into the swab receptacle 1342. As described above, the swab receptacle 1342 tapers down in diameter to a shape/size that compresses the bristles or other material of the swab against the walls of the swab receptacle 1342. In some embodiments, the swab receptacle 1342 comprises one or more walls (or other surfaces) molded with a specifically selected surface finish. The surface finish enables wetting the fluid sample to the walls. As the swab continues to its fully compressed position as it is pushed into the swab receptacle 1342, the fluid that has been wetted to the walls is forced further in front of the swab because of the decreasing cross-section profile of the swab receptacle 1342. As the swab is removed, the fluid that is forced ahead of the swab is drawn back with the swab being removed, trailing behind the swab. At the point in which the bristles or material of the swab have separated far enough from the walls of the swab receptacle 1342, a surface tension of the fluid sample that is wetted to the walls is sufficient to retain at least a portion of the fluid sample in the swab receptacle 1342 (for example, a reservoir portion of the swab receptacle 1342). Thus, the fluid sample to be analyzed by the analyzer is removed from the fluid sample initially collected on the swab and remains in place as the cap 1310 is closed, sealing or substantially sealing the swab receptacle 1342 and the cartridge 1300.

After the swab receptacle 1342 of the cartridge 1300 is closed via the cap 1310, the patient or operator of the analyzer and cartridge may be prompted to insert the now sealed cartridge 1300 into the analyzer 1400. The process of inserting the cartridge 1300 into the analyzer 1400 may actuate multiple features on the cartridge 1300 using static and/or passive components. For example, the singular action of inserting the cartridge 1300 into the analyzer 1400, as performed by the patient or operator, can have its functionality divided into 3 major phases, with some overlap amongst them, as described below.

The first major phase involves inserting the cartridge 1300 into the analyzer 1400. As the cartridge 1300 is first inserted into the analyzer 1400, a static platform located on the bottom mating surface of the cartridge/analyzer interface in the analyzer 1400 depresses a living hinge via interference (for example, mechanical interference). Thus, the static platform translates a linear motion of the cartridge 1300 as it is inserted into the analyzer 1400 into an angular displacement of a lever mechanically coupled to and engaged with the living hinge. The displacement of the lever/living hinge may result in the rupture of the reagent blister 1340. In some embodiments, the lever and/or living hinge may correspond to the integrated rupture feature 1344, introduced above. The lever coupled to the living hinge may continue to rotate about the living hinge and flex along a length of the lever to depress the reagent blister 1340, thereby distributing the reagents into the cartridge 1300 (for example, into the sample mixing and macrofiltration region 1330 of the cartridge 1300). In some embodiments, forces associated with this distribution action may cause the sample in from the swab receptacle 1342 to mix with and be diluted by the reagents from the ruptured reagent blister 1340 in the sample mixing and macrofiltration region 1330. The forces may further distribute the mixed sample and reagent to the reaction wells 1322, rehydrating dried reagents disposed in the reaction wells 1322. The flow of the mixed sample and reagent may terminate at the exhaust gas-permeable membrane 1324 located at the exit of each reaction well 1322, thereby ensuring uniform filling in each well. All of these processes may occur before the cartridge 1300 is inserted into the analyzer 1400.

As a second of the three major phases, the reaction wells 1322 are isolated. As the mixed sample and reagent is distributed through the cartridge 1300 as described above, a path through with the mixed sample and reagent flows transitions from the distribution tree 1328 of the injection molded cartridge body 1302 (for example, the portions of the cartridge 1300 not including and below the thermoformed cover 1314) into small channels 1315 formed in the thermoformed cover 1314. In some embodiments, the thermoformed cover 1314 is attached to the cartridge body 1302 via pressure-sensitive adhesive (PSA) above the plane of the injection molded cartridge body 1302. In some embodiments, the thermoformed cover 1314 also serves as a housing for or includes other fluidic channel components for the cartridge body 1302. In some embodiments, these other fluidic channel components, for example, the well isolation crush valves 1312, act as isolation valves for each individual reaction well 1322. As the cartridge 1300 nears the end of its insertion into the analyzer 1400, after each of the reaction wells 1322 has been filled with the mixed sample and reagent, passive features located on the upper mating surface of the analyzer 1400 "crush" the isolation crush valves 1312 (which may comprise thin channels) down against the PSA bonding the thermoformed cover 1312 or a film to the injection molded cartridge body 1302. Because of the nature of the PSA, the PSA conforms to the deformed shape of the thin film channel in the cartridge body 1302, serving to isolate the reaction well 1322 fluidically from the channels that join the reaction wells 1322 together fluidically. This isolation may prevent crosstalk and diffusion from reaction well 1322 to reaction well 1322. Additionally, this isolation may serve to isolate the reagents and the byproducts of the reaction from the analyzer 1400 and user.

While the cartridge 1302 is being inserted into the analyzer 1400, the third phase occurs. As described above, the well-isolation crush valves 1312 may protrude from an upper surface of the thermoformed cover 1314 on the cartridge body 1302 so that they are crushed when the cartridge 1302 is inserted into the analyzer 1400. This orientation combined with a dual sided heating design for the cartridge 1300 in the analyzer 1400 necessitated a method of removing a heater surface out of the way of the exhaust crush valve 1306. In order to passively accomplish this, an upper heater is mounted to an integrated crossbar and leaf spring of the analyzer 1400. In some embodiments, two cam runners are positioned in a cartridge receptacle of the analyzer 1400 such that when the cartridge 1300 begins to be inserted, the cam runners push the upper heater up and out of the way of the crush valves (for example, the well isolation crush valves 1312 and/or the exhaust port crush valve 1306) disposed on the thermoformed cover 1312. The cam runners continue to pass along an upper edge of the cartridge body 1302 until the cam runners arrive at a molded drop in the upper edge of the cartridge body 1302. The molded drop in the upper edge of the cartridge body 1302 may be timed or positioned in such a way so as to allow the upper heater to press back down against the cartridge body 1302 while not interfering with the thermoformed valves on the thermoformed cover 1312. In some embodiments, the cam runners dropping into the molded drop of the cartridge body 1302 may also double as a retention feature for the cartridge 1300 in the analyzer 1400. As such, the user may displace a leaf spring that moves the upper heater up and out of the way of the crush valves and displacing the cam runners from the molded drop in order to extract the cartridge 1300 after the testing is completed in the analyzer 1400.

After these three major phases are completed, the cartridge 1300 is fully inserted into the analyzer 1400, the mixed sample and reagent are distributed to the reaction wells 1322 and isolated in each reaction well 1322. The upper heater in the analyzer 1400 may uniformly contact the upper surface of the cartridge body 1302, sandwiching the cartridge body 1302 against a lower heater in the analyzer 1400. Upon full insertion, the cartridge 1300 may also establish an electrical connection to the analyzer 1400 via the flexible electrode layer 1304, thereby enabling the analyzer 1400 to begin a test of the mixed sample and reagent in the reaction wells 1322.

In some embodiments, the method for using the cartridge 1300 with the analyzer 1400 to detect a target involves first collecting a sample fluid from a patient or user. In some embodiments, the sample fluid may be collected using a swab or other similar sample collecting method or means. Once the sample fluid is collected, the sample fluid is introduced into the cartridge 1300. For example, when the sample fluid is collected using the swab, the swab is inserted into the cartridge 1300 via the swab receptacle 1342. The optional cartridge cap 1310 may be closed and the cartridge 1300 may be inserted into the analyzer 1400. The insertion of the cartridge 1300 may cause a reagent blister 1340 to rupture and mix the reagents contained therein with the sample fluid. In some embodiments, the mixture of the reagents and the sample fluid is conveyed to the reaction wells 1322. The reaction wells 1322 may each have a volume of approximately 25 microliters (μL). In some embodiments, the reaction wells 1322 has a volume, size, and/or shape that is based on the overall volume of liquid which will fill the reaction wells 1322 as well as a favorable geometry above the sensing electrode. For example, in some embodiments the reaction wells 1322 are circular, triangular, or rectangular, or any other polygonal shape. In some embodiments, when the reaction wells 1322 comprise a plurality of reaction wells (for example, eight (8) reaction wells), the electrodes 1304 (or corresponding circuitry and/or circuit board components/parameters) of the cartridge 1300 may enable the analyzer 1400 to simultaneously test each of the reaction wells 1322 (for example, each representing a different channel) at a plurality of frequencies (for example, three (3) frequencies). In some embodiments, each reaction well 1322 has a depth or height of approximately 1 millimeter (mm). In some embodiments, the reaction wells 1322 may have a shape such that the volume of each reaction well 1322 is or is approximately 25 mL when each reaction well 1322 has a depth or height of 1 mm. In some embodiments, the reaction wells 1322 contain dried enzymes and primers. The primers and enzymes may be spotted into the reaction wells 1322 as liquids and dried (for example, in two spots per well). Thus, the reaction wells 1322 may include dried primers and enzymes while the reagent blister 1340 may include the wet or liquid reagents. In some embodiments, the reagent blister 1340 and/or the reaction wells 1322 may contain liquid reagents and/or primers and enzymes, respectively, configured to allow for the testing of one or more of a viral target, a bacterial target, an antigen target, a parasite target, a microRNA target, an agricultural analyte, an enzyme, an environmental contaminant, pathogens, genomic materials, proteins, PSA levels, elevated or reduced cell counts, specific cells and/or cell types, infections and/or diseases associated with a particular industry or environment, infectious diseases, vector borne diseases, norovirus, rotavirus, and/or any other small molecules or biomarkers. In some embodiments, the dried enzymes and primers are contained in the reagent blister 1340 or elsewhere in the cartridge 1300. Once the mixture of the reagents and the sample fluid is introduced to the reaction wells 1322, one or more heating elements in the analyzer 1400 are activated to increase a temperature of the mixture in the reaction wells 1322 and impedance sensors begin tracking data in real time. The analyzer 1400 then conducts a test through an isothermal nucleic acid amplification process, and any results are communicated to an application and/or a database for further analysis.

In some embodiments, each of the reader devices 110, 600, 910, and 1400 may incorporate any of the functions and/or components of the other reader devices. For example, the components (and corresponding functions) of the reader device 600 in FIG. 6 may be integrated into the reader devices 110, 910, and 1400. Similarly, each of the reader devices 110, 600, and 910 may include the functionality and features of the reader device 1400. Similarly, the reader device 1400 may include in the functionality and features of the readers devices 110 and 910 to process any cartridge inserted into the reader device 1400.

Similarly, each of the cartridges 120, 200, 1000, 1200, and 1300 may incorporate any of the functions and/or components of the other cartridges. For example, the components and corresponding functions of the cartridge 1300 in FIGS. 13A-13E may be integrated into the cartridges 120, 200, 1000, and 1200. Similarly, the cartridge 1300 may include in the functionality and features of one or more of the cartridges 120, 200, 1000, and 1200 and may be processed by any reader device described herein.

The various components of the handheld detection systems 100 and 900 (for example, the analyzers or reader devices 110, 600, 910, and 1400 and cartridges 120, 200, 1000, 1200, and 1300, described herein) may be integrated with an external computing device. The external computing device, for example a mobile phone, a computer, a tablet, a laptop, or similar device, may communicate with the reader devices 110, 600, 910, and/or 1400 using a communication interface, for example the communications module 615. The external computing device may comprise a testing monitoring and/or control application installed thereon to provide a user options and abilities to monitor and/or control one or more of the cartridge and the reader device. Further details of the functionality of the testing control application (including providing a testing system user interface for controlling options and/or presenting test results and other test information to users, on a display of the remote device) are provided below with reference to FIGS. 15A-15P.

Figure 15A:
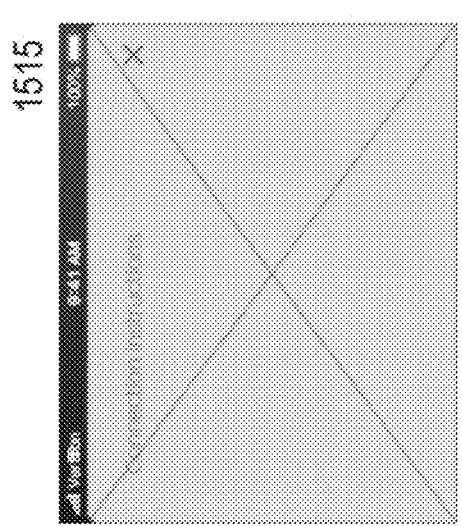
FIGS. 15A-15P depict screenshots of an example graphical user interface hosted on an external computing device and configured to receive input, provide instructions, testing control, and/or monitoring of the handheld system disclosed herein.
Figure 15B:
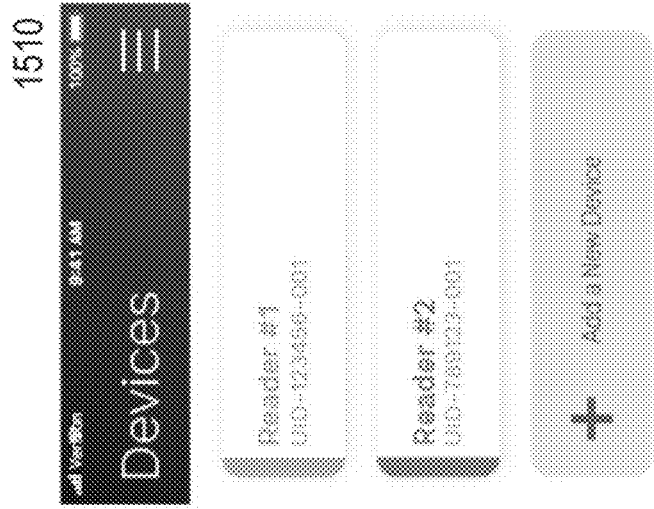
Figure 15C:
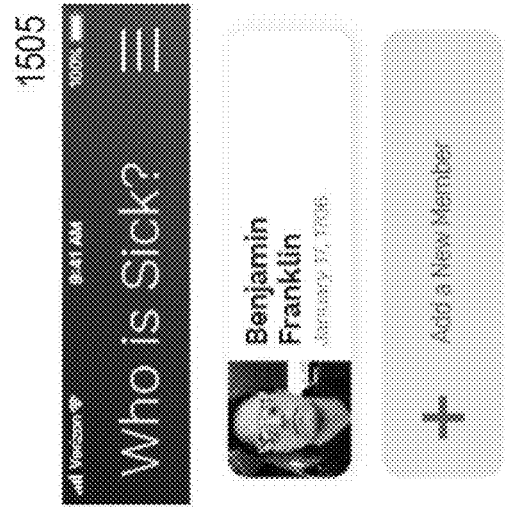
Figure 15D:
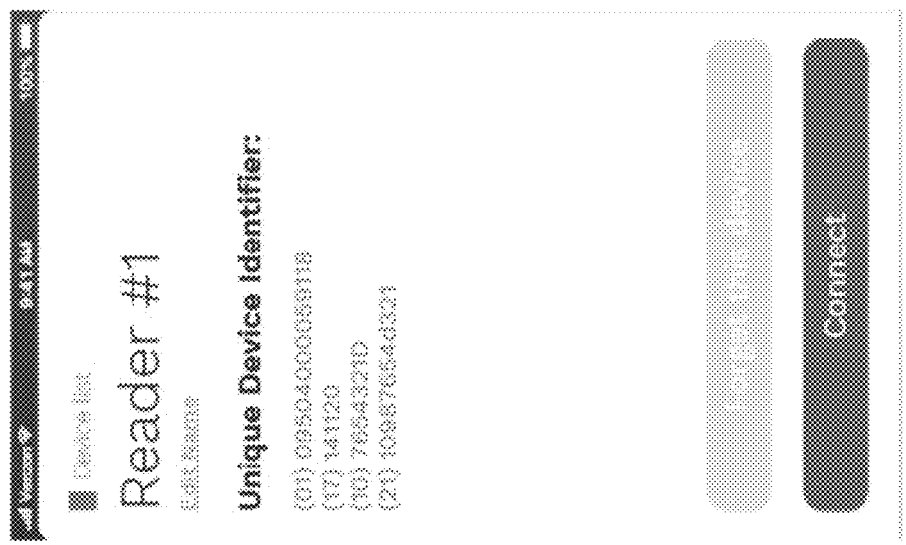
Figures 15H, 15I, 15J:
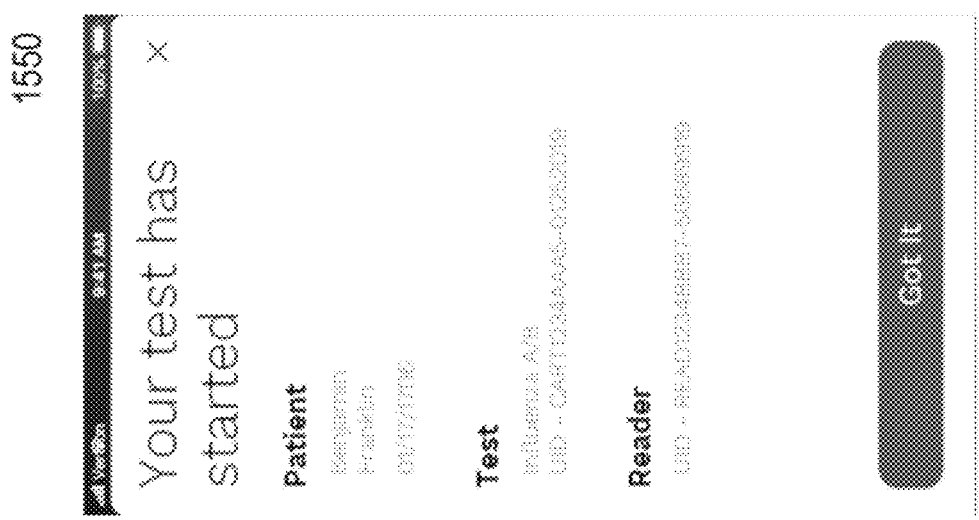
Figure 15M:
Figure 15L:
Figure 15K:
Figures 15N, 15O, 15P:
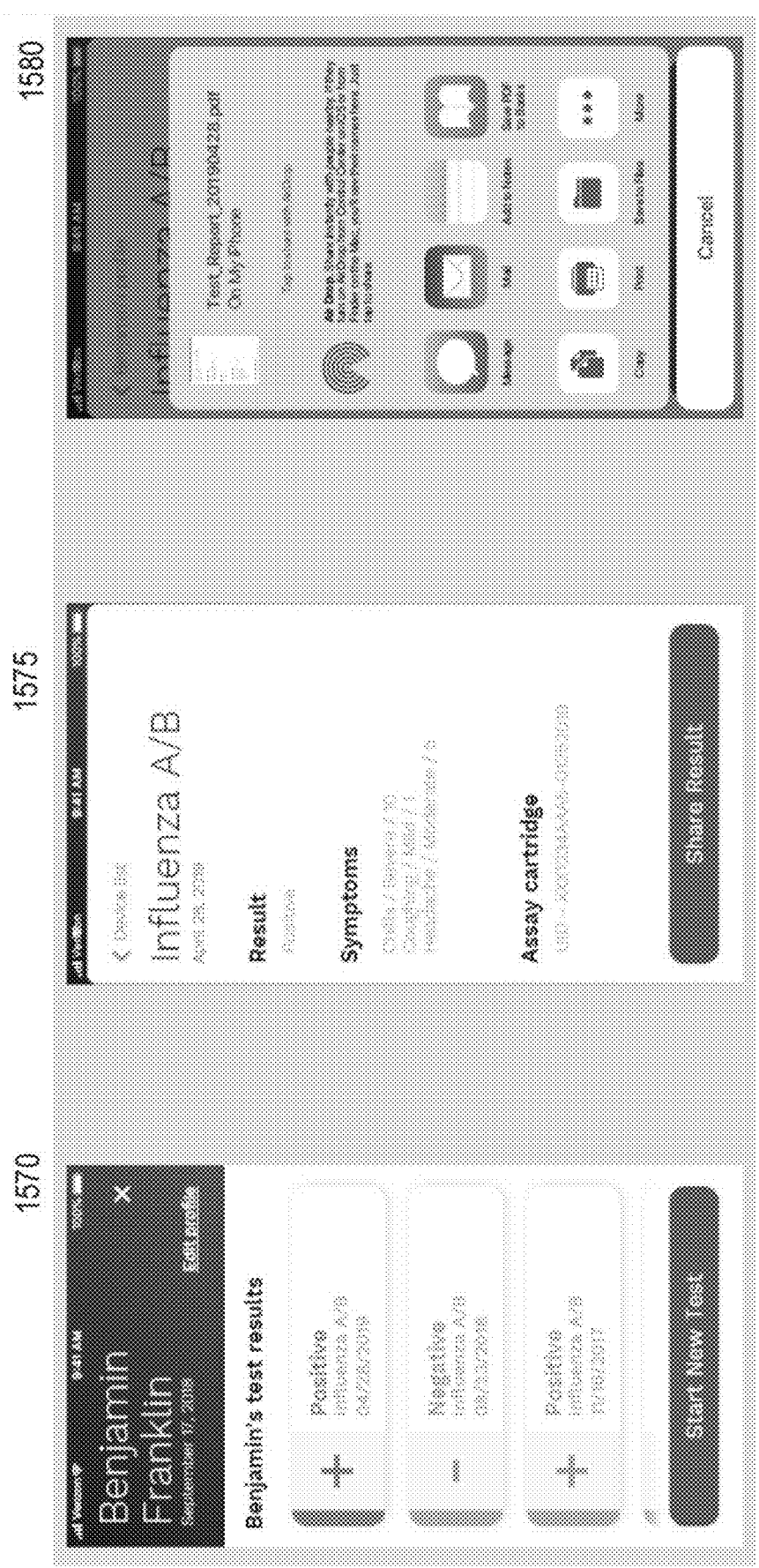

FIGS. 15A-15P depict screenshots of an example graphical user interface 1500 hosted on an external computing device and configured to provide testing control and/or monitoring of the handheld system disclosed herein. The graphical user interface 1500 may include one or more of the features of the graphical user interface 800 described with reference to FIGS. 8A-8D above.

The user interface 1500 may be, for example, the user interface 620 illustrated in connection with the reader device 600 of FIG. 6 or the user interface 800. The user interface 1500 may be implemented with any of the reader devices 110, 600, 910, and/or 1400 and/or assay cartridges 120, 200, 1000, 1200, and 1300 described herein. The screens depicted in FIGS. 15A-15P may be displayed, for example, by an application executing on the external computing device paired to the reader device 110, 600, 910, 1400 (e.g., by WiFi, Bluetooth, or the like). The screens may allow a user of the external computing device to control and/or monitor the reader device 110, 600, 910, 1400 from the external computing device.

FIG. 15A depicts an initial user screen 1505 which may be displayed when the application is activated or run. In one example, a user selects the application from a home screen or the application is launched automatically when the external computing device is paired with the reader device. In some embodiments, the application may run in the background of the external computing device and automatically open or prompt the user when the application detects that the reader is paired to the external computing device or when a cartridge is inserted into the reader device. The user screen 1505 optionally includes a header portion that may be generic to all or a majority of screenshots for the application. The header portion may include a title portion and a menu portion. The title portion may provide a title for the screen being viewed (for example, the title portion for the user screen 1505 includes "Who is Sick?", prompting the user of the application to select or add a person for whom a test has been run, is being run, or will be run. The menu portion optionally may comprise a "hamburger" button that, when clicked, presents the user with available options from a current screen (for example, the screen from which the user accesses the hamburger button.

The user screen 1505 allows the user to identify a patient for which test results are being generated by the reader device, test results are being reviewed, or a profile is being created, revised, or reviewed. The user may be one of the patients identified on the screen 1505 or may be associated with one of the patients identified. The user screen 1505 identifies a single patient's profile, "Benjamin Franklin", but includes a button to add new patients or people to the application. By including an ability for multiple patients to be associated with the application (for example, have test information stored in or by the application), the user interface can link and reference tests associated with corresponding patients in a simplified and secure manner. Accessing a patient's account may require a password or biometric (or other) authentication to ensure privacy of test results and corresponding data.

When the user logs into the application (and provides any necessary authorization information), the application may provide the user with the option to edit an existing profile (for example, the Benjamin Franklin profile) or add a new profile. When the user edits the existing profile(s), the user may edit one or more of the name, birthdate, and representative image or photo. In some embodiments, editing the existing profile comprises removing or deleting the existing profile, which may delete the profile along with any associated information (for example, associated test information). In some embodiments, when a profile is deleted, the user has the option to save or export corresponding test information and other information. When the user adds a new profile, the user may create a new profile including the name, birthdate, and/or representative image or photo for the new profile. Adding a new profile may require the user to authenticate (for example, via e-mail authentication) some information associated with the new profile.

In some embodiments, when the user selects the menu button on any of the screens (for example, screen 1505 of FIG. 15A, the menu may provide the user with many options. The options include: (1) closing the menu; (2) transitioning to a home page; (3) transitioning to a page to manage connected devices; (4) transitioning to a page for ordering supplies; (5) transitioning to a page with information about the application; (6) transitioning to a page to contact a vendor of the application; (7) transitioning to a page for a user manual; and (8) logging out of and exiting the application. Option (1) may close the menu and return the user to the previously visible screen. Option (2) may take the user to the home page of the application, which may be the "Who is Sick?" page where the patient is selected. Option (3) may transition to a page where connected devices (for example, one or more of the reader devices 110, 600, 910, and/or 1400) are managed. Option (4) transitions to a page where the user can order supplies, for example additional cartridges 120, 200, 1000, 1200, and/or 1300 or reader devices 110, 600, 910, and/or 1400, swabs, or similar items. Option (5) may display details of the application (for example, copyright date, version information, application identifier, and so forth). Option (6) may allow the user to contact the vendor of one or more of the application, the reader devices 110, 600, 910, and/or 1400, and the cartridges 120, 200, 1000, 1200, and/or 1300. Option (7) opens a digital user manual for one or more of the application, the reader devices 110, 600, 910, and/or 1400, and the cartridges 120, 200, 1000, 1200, and/or 1300. Option (8) causes the user to sign out (for example, de-authenticate) and exit the application.

Option (3) from the menu may transition the application to the user screen 1510 of FIG. 15B, having the title portion "Devices". The screen 1510 shows devices that are added to and/or associated with the application, such as the Reader #1 and the Reader #2, and an option to add a new device. When the user selects to add the new device, the application transitions to a pairing reader screen 1515 that requests the user to input information to enable the application to communicate with the new device(s), such as a new reader. For example, the pairing reader screen 1515 may prompt the user to pair the new reader with the application over Bluetooth, Wi-Fi, or another communication medium. The pairing reader screen 151 may include a video prompt to show the user how to add the new reader and generally include instructions for pairing the new reader with the application. In some embodiments, the pairing reader screen 1515 may prompt the user to scan or enter a barcode on or associated with the new reader. Once the new reader is added to or associated with the application, the application may return to the screen 1510, where the added reader (e.g., Reader #2) is shown with a note of "Device added!".

When the user selects one of the added devices (for example, the Reader #1), the application transitions to a user screen 1520 of FIG. 15D. The user screen 1520 may provide various information and options to the user. For example, the user screen 1520 provides an option to change the name of the Reader #1, to forget the Reader #1, and to connect to the Reader #1. If the Reader #1 is currently connected to the application, then the user screen 1520 may provide an option to disconnect from the Reader #1. The user screen 1520 also displays identifying information for the Reader #1 and may include a connection status indicator, indicating a status of the connection between the Reader #1 and the application. In some embodiments, the user screen 1520 also includes information regarding current status of the Reader #1. For example, the screen 1520 can indicate whether the Reader #1 is performing a test, analyzing a cartridge, waiting for a cartridge, and so forth, or a recently completed action. Though not shown in FIG. 15D, the screen 1520 may provide one or more commands or controls to the Reader #1.

As described herein, the reader devices and the cartridges provide testing for target agents. The application on the external computing device may facilitate the performance, control, and review of the test and the review and/or communication of the test results. For example, user screen 1525 of FIG. 15E shows results for the user Benjamin Franklin for two previous tests or provides the user the option to start a new test. The screen 1525 shows the two previous test results: a positive test result for Influenza A/B on Apr. 28, 2019 and a negative test result for Influenza A/B on Apr. 28, 2019. The user of the external computing device may select one of the previously completed positive and negative test results and review details of the test, the test results, and any symptoms reported for the patient at the time that the selected test was performed. Additionally, the user can review identifiers for the cartridge from each test and/or the reader device from each test. When the user selects to start a new test, the user interface 1500 may prompt the user to connect to a reader device (for example, one of reader devices 110, 600, 910, and/or 1400, if not already connected). The user interface may also request the user to identify a cartridge (for example, one of cartridges 120, 200, 1000, 1200, and/or 1300) to be used in the test.

When the user selects to start a new test from the screen 1525, the user interface 1500 transitions to and through the screens described above that the user accesses when selecting to add the new reader from the screen 1510. As such, the pairing and connecting of the reader device with the external computing device and user interface 1500 may be completed as described above. When the reader device is paired with the external computing device and the user interface 1500, the user interface 1500 may prompt the user to identify the cartridge being used with the paired reader device at a user screen 1530 of FIG. 15F. The screen 1530 provides the user with a video and/or instructions for identifying, to the application, the cartridge being used. In some embodiments, as described herein, different cartridges may be used for different tests. For example, an influenza test uses a first cartridge while a bronchitis test uses a second cartridge. Because the different tests may use different cartridges, identifying the cartridge to being used for the test may be essential to the test providing a reliable result when analyzed by the reader device. For example, the reader device may receive specific instructions and/or set points, etc., for use in the test based on the identified cartridge. Thus, the instructions provided by the screen 1530 may include scanning a barcode or taking a picture of the cartridge being used or manually entering information identifying the cartridge.

Once the user provides the details of the cartridge being used for the requested test, the user interface 1500 provides instructions to the user for using the cartridge, at a screen 1535 of FIG. 15G. The instructions comprise obtaining a swab and removing a cartridge that matches the identified cartridge for use in the test. The screen 1535 also shows the test that corresponds to the selected and identified cartridge, in this case the influenza A/B test. The screen 1535 may provide any additional instructions or notes to assist the user in preparing to conduct the test.

FIGS. 15H-15J show the user screens 1540-1550, which include instructions provided to the user via the external computing device. The instructions provided to the user screens 1540-1545 include instructions for getting the sample, loading the sample into the cartridge, and getting the cartridge into the reader device. For example, the user interface 1500 instructs the user to get the sample by swabbing the patient's nose such that mucus covers a tip of the swab. The instructions tell the user to then put the tip of the swab into the cartridge and then retract or extract the swab, which causes the cartridge to scrape the mucus into the cartridge. The instructions further teach the user to insert the cartridge into the reader until the user hears a click, which may cause the test to begin. The click may be the result of a mechanical coupling of the reader device to the cartridge. In some embodiments, the user interface 1500 may provide additional instructions to the user. The screens 1540-1550 also include navigation buttons to navigate between screens. The screen 1550 may indicate to the user that the corresponding test has begun. Specifically, the screen 1550 provides the user with a summary of the patient or subject (for example, Benjamin Franklin) along with some information about the patient (for example, date of birth). The screen 1550 also provides details on the test being run, here the Influenza A/B test, and an identifier for the cartridge being used to run the test and the reader running the test. In some embodiments, the screen 1550 also includes a timer or countdown indicating how much time is remaining in the current test, if any.

FIGS. 15K-15M show examples of user screens 1565-1565 through which the user can provide symptoms that the patient is experiencing. In some embodiments, the user can provide the symptoms before the test is run, while the test is run, and/or after the test is run. In some embodiments, the reader or the user interface (herein referred to also as the "application") may use the symptoms in conjunction with the test results to make a determination as to whether the patient is suffering from an ailment (otherwise referred to herein as a sickness or illness) associated with the test. For example, as shown in FIGS. 15K and 15L, the user can input or select symptoms such as fever, chills, muscle aches, sore throat, headache, congested or runny nose, cough, difficulty breathing, decreased appetite, or decreased activity, and so forth. The user may input a symptom that is not shown in FIGS. 15K and 15L. In some embodiments, the user interface 1500 allows the user to select severity levels associated with one or more indicated symptoms, as shown on the screen 1560. For example, if the patient reports having a fever, the user can enter the patient's temperature when the swab collected the sample of the patient's mucus. Similarly, other symptoms may have sliding scale values to provide associated values (for example, a sliding scale for severity of muscle aches or congestion, and so forth. Additionally, screens 1555-1565 include a timer or countdown regarding the test being run as well as the patient name and the test name. On the screen 1565 of FIG. 15M, the user interface 1500 shows when the test is complete and shows any symptoms that the user identifies for the patient. The screen 1565 also gives the user options to view the results of the completed test. The results may include any target agent levels or associated information.

The screen 1570 of FIG. 15N shows a list of completed tests, similar to the screen 1525 of FIG. 15E, described above. However, the screen 1570 includes an additional test as compared to the screen 1525, the additional test being the influenza A/B test completed in screen 1565. The new test is shown as being positive for influenza A/B and includes the date on which the new test was completed. In some embodiments, though not shown in the figures, the user interface 1500 can show the status of the reader device being disconnected and unable to show test results. In some embodiments, if the reader device becomes disconnected from the user interface 1500 and the external computing device during a test, then the user interface 1500 may provide the user with an alert and/or steps to take to reconnect with the reader device. In some embodiments, if the reader device is disconnected from the user interface 1500 and the external computing device, then the user interface 1500 may track and/or display information from when the reader device was last connected to the user interface 1500 and the external computing device. Selecting the new test on the screen 1570 causes the user interface 1500 to present the screen 1575 of FIG. 15O, which includes details of the positive influenza A/B test, symptoms reported along with the test by the user, and details of the cartridge used in the test and potentially the reader device used in the test. In some embodiments, the screen 1575 of FIG. 15O may also include an indicator (not shown in the figures) of a diagnosed ailment and/or one or more recommended steps to follow-up on the test results and/or the indicated ailment. Screen 1580 of FIG. 15P provides the user with options for sharing the test results, for example via text message, e-mail, printing, and so forth. In some embodiments, the user establishes a default sharing plan for all test results, symptoms, and other data for a particular patient. For example, the user can set up the sharing plan to e-mail or message all results, symptoms, and other data to the patient's doctor or parents automatically upon completion of a test or entry of new data, or both.

In some embodiments, as described above with reference to FIGS. 8A-8D, the external computing device and the user interface 1500 are used to scan a cartridge identifier (e.g., cartridge identifier 215 of FIG. 2B) of a cartridge before inserting the cartridge into the reader device. When the cartridge is inserted, the paired reader device detects the inserted cartridge and sends a message to the user interface that the cartridge has been inserted. The user interface 1500 may then display one of the screens described above, with reference to FIGS. 15A-15P. In some embodiments, one or more of the screens of the FIGS. 15A-15P include one or more of the indications, buttons, input fields, areas, and so forth of the FIGS. 8A-8D.

In some embodiments, the user interface (for example, the user interface 1500 or the user interface 800) works with the reader device (for example, one of the reader devices 110, 600, 910, and/or 1400) to determine whether a patient is suffering from a particular illness. For example, the reader device may perform a test using one of the cartridges 120, 200, 1000, 1200, and/or 1300 and determine that a particular target agent is present in the patient's mucus. However, merely the presence of the target agent may be insufficient to determine that the patient is suffering from an illness or ailment. For example, if the patient is merely a carrier of an illness, the patient test results may indicate presence of the virus but the patient may not be suffering from an associated illness. Thus, the user interface may receive symptoms that the patient is experiencing and combine these symptoms with the test results from the reader device to determine whether the patient is suffering from an illness or ailment corresponding to the target agent. For example, if the test result from the reader device indicates the presence of the influenza A/B virus in the patient's mucus but the patient is not experiencing or reporting any symptoms, then the user interface may determine that the patient is not suffering from the influenza virus but is instead a carrier for the virus. On the other hand, when the test result indicates the presence of the influenza A/B virus and the patient reports symptoms known to coincide with the influenza A/B virus in someone suffering from the influenza illness, then the user interface may determine that the patient is infected with the influenza illness. Such a determination may be based on a threshold number of symptoms or specific being met while the target agent is detected (for example, one or two symptoms being suffered while the influenza A/B virus is present). The symptoms may be weighted differently depending on the target agent in the test and/or the corresponding illness. For example, when the target agent is influenza A/B, then symptoms such as fever, chills, muscle aches may be more highly weighted than symptoms such as headache or cough. Thus, symptoms associated with a corresponding illness for the target agent may have higher weights and be more indicative that the patient carrying the virus is suffering the corresponding illness. In some embodiments, the threshold number of symptoms, weighting of symptoms, or specific symptoms to be met to determine that the patient is ill is determined based on one or more metrics. A standard setting or national organization, such as the Center for Disease Control (CDC) or similar organization or entity, may establish the one or more metrics. Thus, the user interface may use the test results from the reader device and the symptom information provided by the user to determine whether the patient is (1) ill or sick or (2) a carrier for the target agent. In some embodiments, the user interface offloads one or more of the determinations described herein to one or more external systems with which the user interface (and the corresponding external computing device) interacts.

In some embodiments, the user interface may generate a score or similar indicator to indicate a probability that the patient is ill or sick. A higher score may correspond to a higher probability that the patient is ill while a lower score may correspond to a higher probability that the patient is not ill. For example, the user interface may use details from the test results from the reader device along with the user provided symptom information to generate the score indicating the probability of sickness of the patient.

The reader device may provide test results that include a range of values, where the range of values correspond to a range of possible detection levels of the target agent. For example, the test results may include one or more of a likelihood that the mucus sample included the target agent (for example, between 0 and 100% probability) and a quantity of the target agent determined to have been included in the mucus sample. The probability that the mucus sample included the target agent may be associated with the quantity of the target agent determined to have been included in the mucus. The range of possible detection levels may refer to different likelihoods or probabilities that the patient has a particular virus or infection. For example, if the reader device provides test results indicating that the patient does have the virus or infection with 100% certainty or that a quantity of the target agent above a first threshold was present, then the score (or probability) may be assigned a minimum value, for example 50 out of a 0 to 100 range. Then, if the patient is experiencing any symptoms associated with the illness associated with the virus or infection, then the value of the score (indicating that the patient is suffering from the corresponding illness) may be increased. For example, for each symptom that the patient experiences that is associated with the illness, the value may increase by a threshold value (for example, 10 points). Thus, the combination of the target agent detection and the symptoms can increase or decrease the score or probability of the patient being sick. Alternatively, if the reader device indicates that the patient has the virus or infection with 50% certainty (or that a quantity of the target agent below the first threshold but above a second threshold was present), then the score may be assigned a different minimum value, for example 25 out of the 0 to 100 range. Accordingly, when the test results indicate a lower probability of the presence of the target agent, more symptoms suffered by the patient are needed to increase the score to the same value as compared to when the test results indicate a high probability of sickness. If the reader device indicates that the patient does not have the virus or infection (or that a quantity of the target agent below the second threshold was present), then the score may be assigned a zero value, for example 0 out of the 0 to 100 range. When the score starts at a zero value based on the test results, no quantity of symptoms may be sufficient to raise the score because the virus or target agent is not present to make the patient ill. Thus, the user interface and the reader device may together generate the score that represents the probability of the patient being sick based on the test results of the target agent and the symptoms suffered by the patient.

In some embodiments, the user interface may review the test results and the provided symptoms to determine whether the patient is suffering from a particular illness not associated with the target agent for which the test was run. For example, if the patient's test results are negative for influenza A/B but the patient is experiencing a fever with chills and a sore throat, the user interface may determine that the patient is suffering from a cold or respiratory syncytial virus (RSV). Thus, the user interface may identify an illness that the patient is suffering from or is likely suffering from based on a positive or negative test results and the symptoms experienced. As such, the user interface may use knowledge (for example, databases) of similarities and differences in symptoms of different illnesses but differences in test results and so forth in illness determinations.

In some embodiments, the user interface generates a score value that indicates a probability that the patient is sick or ill, based on the test results and the symptom information. The user interface may further aggregate external information into the score value, regardless of what the test results and symptoms by themselves would otherwise indicate. The external information may include one or more of test results from other patients that used the same reader device, test results from other reader devices that interfaced with the user interface and the external computing device, test results and other diagnostic information for patients in a hospital or a geographic region, and so forth. For example, the user interface may use test results and/or symptom information from other patients tested by the reader device to inform further the score values. For example, many other patients tested with the reader device coupled to the user interface have positive test results for the same target agent and report one or more similar symptoms. The user interface may use this information to increase a score or probability that the patient is ill or sick, even if the patient's test results and/or symptoms may alone not indicate that the patient is ill. Similarly, the test results and the symptom information for the patient may indicate that the patient is ill but other patients having similar test results and symptoms report that they are not ill. The user interface then may decrease the score or probability that the patient is ill, regardless of what the patient's test results and/or symptom information otherwise indicate. If the test results and the symptoms for the patient are different from those of other patients that report as not being sick (for example, by a threshold amount), then the user interface may increase the score or probability that the patient is sick. On the other hand, if the test results and symptoms are different from those of other patients that report as being sick (for example, by the threshold amount), then the user interface may decrease the score or probability that the patient is sick, regardless of the test results and symptoms.

In some embodiments, the user interface performs one or more actions based on the score or probability values. The user interface may communicate information to one or more of the user, the patient, attending medical staff, the CDC, or similar entities. Alternatively, or additionally, the user interface may generate an alert to the one or more of the user, the patient, attending medical personnel, the CDC, or similar entities. The alert may comprise one or more of a phone call, a text message, an e-mail message, a push message, an audio message, a flashing indicator, or audible indicator, or any other communication used to communicate information. For example, the user interface may automatically generate and transmit an alert to the user based on the results of the test or the indicated symptoms, a combination of the two, or the test results or symptoms in aggregate with information from other patients. For example, if the test results and the indicated symptoms suggest that the patient is suffering from a rare illness, then the user interface may generate and communicate an alert to the patient or user suggesting a follow-up visit to a specialist. Similarly, if the test results and the indicated symptoms suggest that the patient is suffering from highly contagious illness, then the user interface may generate and communicate the alert to the patient or user requesting that the patient restrict interaction with others to minimize risk of communication of the illness to others. If the test results and the indicated symptoms suggest that the patient is suffering from a highly contagious, rare, and difficult to treat illness, then the user interface may generate and communicate the alert to the patient or user but also to local, regional, or national medical staff or disease monitoring agencies. As such, the reader device, cartridge, and user interface on the external computing device may generate information used to help detect an outbreak of a virus or disease.

For example, the user interface and the external computing device may communicate and/or interact with a system that tracks illnesses over a geographic area, for example a city, county, state, or nation, or a specific portion of the population. Thus, the user interface and the external computing device may enable tracking of diseases and/or infections by the system for a number of patients in various geographic areas. In some embodiments, the system performs the tracking based on one or both of the test results and the identified symptoms. In some embodiments, the system performs the tracking based on the scores or probabilities generated by the user interface. The system may aggregate and use the information from multiple user interfaces and external computing devices to generate a geographic heat map. The heat map may show levels of one or more illnesses and/or corresponding rates of infection or healing as different colors or levels on the map, where different colors correspond to different levels (for example, numbers) of reported injections or rates of infection. Thus, the heat map may visually show how numbers of ill patients vary in the geographic area. In some embodiments, the system may use such heat maps to identify pockets of specific illnesses or infections and/or an epidemic that is occurring based on aggregated test results and symptoms provided from multiple user interfaces and corresponding external computing devices. The heat map may show different quantities of illnesses or different rates of illness detection in different colors. The heat map may enable an entity to review quickly the geographic area to identify relational information (for example, information for portions of the geographic area relative to one another) and specific information (for example, detailed information for individual portions of the geographic area).

In some embodiments, the user interface and the external computing device may be integrated with a system (for example, the system that generates the heat map) used to track and/or determine need for vaccines or other medications. The system may receive the test results, symptoms, and/or scores from a number of user interfaces and corresponding external computing devices. The system may track that information to ensure that a particular geographic region is supplied with appropriate vaccines or medications to handle the identified quantity of illnesses. If the system identifies that a difference in identified illnesses and an expected level of supplies exceeds a determined threshold, then the system may automatically request vaccine and/or medication suppliers to increase production to meet an expected demand based on the illnesses tracked by the system. For example, the system determines that test results, symptoms, and/or scores received from a city in California indicate that 50,000 people out of a population of 500,000 are suffering from influenza A/B. The city is expected to have vaccine and medication supplies for 10,000 people to treat and prevent the spread of the influenza A/B virus (for example, only 10,000 units of medication and/or vaccines). The system may determine that the difference of 40,000 people exceeds the threshold amount and may automatically request that influenza A/B vaccine and medication manufacturers and/or suppliers increase production and provide an increased supply to the city. Such automatic detection of supply need and request for additional supplies may improve response times in times of outbreaks and help prevent and/or reduce the spread of communicable diseases.

Similarly, such aggregate tracking of test results, symptoms, and/or scores may allow the system to provide recommendations. Such recommendations may include increased education, advertisement, and so forth. For example, if the system determines an increase in numbers of people infected with a communicable disease that presents itself as or shares symptoms with another disease, then the system may recommend increased education of the different diseases and advertisements to inform people of the potential confusion and to help them seek treatment. For example, certain sexually transmitted diseases may exhibit cold- or flu-like symptoms. For example, hepatitis and/or gonorrhea may have similar symptoms to the common cold or influenza. Thus, some people experiencing the cold-like or flu-like symptoms may not get tested for any infection, assuming they just have the cold or flu. Thus, the system may determine that an unusually large number of people in a town have test results, symptoms, and scores that indicate infection with hepatitis during a period when a large number of patients are reporting cold or flu infections. The system may then determine that education regarding safer sex practices and differences between the diseases should be provided to the town. The system may also recommend increased advertisement about the spike in infections to encourage the safer practices and lead to increased detection and treatment for the appropriate illness.

In some embodiments, the user interface may also generate an indicator to indicate whether the patient is becoming sicker or healthier. For example, if the user performs multiple tests for the patient, then the user interface may determine that different combinations of symptoms suffered by the patient or different quantities of the target agent in the test sample indicate whether the patient is sicker than a previous test or healthier than a previous test. In some embodiments, the indicator may comprise an arrow or representation of a face, or similar indicator.

Overview of Example Devices

Some embodiments of the methods, systems and compositions provided herein include devices comprising an excitation electrode and a sensor electrode. In some embodiments, the excitation electrode and the sensor electrode measure electrical properties of a sample. In some embodiments, the electrical properties comprise complex admittance, impedance, conductivity, resistivity, resistance, and/or a dielectric constant.

In some embodiments, the electrical properties are measured on a sample having electrical properties that do not change during the measurement. In some embodiments, the electrical properties are measured on a sample having dynamic electrical properties. In some such embodiments, the dynamic electrical properties are measured in real-time.

In some embodiments, an excitation signal is applied to the excitation electrode. The excitation signal can include direct current or voltage, and/or alternating current or voltage. In some embodiments, the excitation signal is capacitively coupled to/through a sample. In some embodiments, the excitation electrode and/or the sensor electrode is passivated to prevent direct contact between the sample and the electrode.

In some embodiments, parameters is optimized for the electric properties of a sample. In some such embodiments, parameters can include the applied voltage, applied frequency, and/or electrode configuration with respect to the sample volume size and/or geometry.

In some embodiments, the voltage and the frequency of the excitation voltage may be fixed or varied during the measurement. For example, measurement may involve sweeping voltages and frequencies during detection, or selecting a specific voltage and frequency which may be optimized for each sample. In some embodiments, the excitation voltage induces a current on the signal electrode that is can vary with the admittance of the device and/or sample characteristics.

In some embodiments, the detection parameters is optimized by modeling the admittance, device and sample by the lumped-parameter equivalent circuit consisting of electrode-sample coupling impedances, sample impedance, and inter-electrode parasitic impedance. Parameters of the lumped-parameter equivalent circuit is determined by measuring the admittance of the electrode-sample system at one or many excitation frequencies for a device. In some embodiments, the complex (number having both real and imaginary components) admittance of the electrode-sample system is measured using both magnitude- and phase-sensitive detection techniques. In some embodiments, the detection parameters are optimized by determining the frequencies corresponding to the transitions between the frequency regions by measuring the admittance across a wide range of frequencies. In some embodiments, the detection parameters are optimized by determining the frequencies corresponding to the transitions between the frequency regions by computing from the values given lumped-parameter model.

In some embodiments, the admittance of a capacitively-coupled electrode-sample system comprises three frequency regions: a low frequency region dominated by the electrode-sample coupling impedance, a mid-frequency region dominated by the sample impedance, and a high frequency region dominated by parasitic inter-electrode impedance. The admittance in the electrode-sample coupling region is capacitive in nature and is characterized by a magnitude that increases linearly with frequency, whose phase is ninety degrees. The admittance in the sample region is conductive in nature and is characterized by an admittance that does not vary significantly with respect to frequency, whose phase is approximately zero degrees. The admittance inter-electrode region is capacitive in nature and is characterized by a magnitude that increases linearly with frequency and a phase of ninety degrees.

In some embodiments, an induced current at the pick-up electrode is related to the excitation voltage and complex admittance by the relation:

current=(complex admittance)×(voltage)

In some embodiments, the device measures both the excitation voltage magnitude and induced current magnitude to determine the magnitude of the complex admittance. In some embodiments, the device is calibrated to known excitation voltages and measure the magnitude of the induced current. In order to determine the phase of complex admittance, the device may measure the relative phase difference between the excitation voltage and the induced current.

In some embodiments, the magnitude and phase is measured directly.

In some embodiments, the magnitude and phase is measured indirectly e.g., by using both synchronous and asynchronous detection. The synchronous detector gives the in-phase component of the induced current. The asynchronous detector gives the quadrature component of the induced current. Both components can be combined to determine the complex admittance.

In some embodiments, the electrodes are not passivated.

In some embodiments, the excitation and/or detection electrodes are passivated. The excitation and/or detection electrodes may be passivated to prevent e.g., undesirable adhesion, fouling, adsorption or other detrimental physical interactions between the electrode with the sample or components therein. In some embodiments, the passivation layer comprises a dielectric material. In some embodiments, passivation enables efficient capacitive coupling from the electrodes to the sample. The efficiency of the coupling is determined by measuring the characteristics of the electrode/sample system, for example, which may include: the dielectric properties of the passivation layer, the thickness of the passivation layer, the area of the passivation/sample interface, the passivation surface roughness, the electric double layer at the sample/passivation interface, temperature, applied voltage and applied frequency, the electrical properties of the sample, the electric and/or chemical properties of the electrode materials.

In some embodiments, the electrode configuration and fabrication is optimized to mitigate undesirable parasitic coupling between electrodes. This may be accomplished through electric field shielding, the use of a varying dielectric constant electrode substrate, layout optimization, and/or grounding layers.

Implementing Systems and Terminology

Implementations disclosed herein provide systems, methods and apparatus for detection of the presence and/or quantity of a target analyte. One skilled in the art will recognize that these embodiments may be implemented in hardware or a combination of hardware and software and/or firmware.

The signal processing and reader device control functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. An assay cartridge for containing a sample comprising a target agent for detection by a reader device, the assay cartridge comprising:
    a cartridge body configured to be received by the reader device, the cartridge body including:
        a test well containing an excitation electrode and a sensing electrode, wherein the test well is configured to contain at least a portion of the sample comprising the target agent undergoing an amplification process;
        a capillary tube receiving well configured to receive a capillary tube containing the sample; and
        a plunger receiving well; and
        a fluid path fluidically coupling the capillary tube receiving well to the test well; and
    a cap comprising:
        a retaining well having an interior diameter larger than an exterior diameter of the capillary tube;
        a retaining structure disposed within the retaining well and configured to retain the capillary tube at a position spaced from a side interior wall and a rear interior wall of the retaining well to form at least one air channel fluidically coupled to an inner end of the capillary tube; and
        a plunger disposed about a portion of the retaining well, wherein
        the cap is configured to hold the capillary tube containing the sample, and the cap is further configured to mechanically couple to the cartridge body, wherein mechanically coupling the cap to the cartridge body causes compression of a trapped volume of a fluid to drive at least a portion of the sample through the fluid path into the test well,
    wherein the capillary tube receiving well is configured to sealingly receive an outer end of the capillary tube to fluidically couple an inner lumen of the capillary tube to the fluid path when the cap is mechanically coupled to the cartridge body,
    wherein the plunger receiving well is configured to sealingly receive the plunger when the cap is mechanically coupled to the cartridge body, and
    wherein, as the cap is mechanically coupled to the cartridge body, the plunger compresses a volume of air within the plunger receiving well, such that the air flows through the air channel and forces the sample to travel into the fluid path of the cartridge body.

2. The assay cartridge of claim 1, wherein the cartridge body further comprise a hollow plunger comprising an interior space fluidically coupled to the fluid path of the cartridge body, wherein the cap comprises a plunger receiving well configured to sealingly receive the hollow plunger, and wherein, as the cap is mechanically coupled to the cartridge body, the plunger compresses a volume of air within the plunger receiving well, such that the air flows through the hollow plunger and forces the sample to travel into the fluid path of the cartridge body.

3. The assay cartridge of claim 2, wherein the cartridge body comprises at least a second test well containing an excitation electrode and a sensing electrode, and a second fluid path fluidically coupling the capillary tube receiving well to the second test well, wherein the second test well is configured to contain at least a portion of the sample comprising the target agent undergoing an amplification process.

* * * * *